(12) United States Patent
Mori et al.

(10) Patent No.: US 12,404,268 B2
(45) Date of Patent: *Sep. 2, 2025

(54) 2-HETEROARYL AMINOQUINAZOLINONE DERIVATIVE

(71) Applicant: Sumitomo Pharma Co., Ltd., Osaka (JP)

(72) Inventors: Kazuto Mori, Osaka (JP); Hiroyuki Kitano, Osaka (JP); Tomoyuki Furuta, Osaka (JP); Hajime Seki, Osaka (JP); Yohei Kobayashi, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 976 days.

This patent is subject to a terminal disclaimer.

(21) Appl. No.: 17/433,193

(22) PCT Filed: Apr. 23, 2021

(86) PCT No.: PCT/JP2021/016498
§ 371 (c)(1),
(2) Date: Aug. 23, 2021

(87) PCT Pub. No.: WO2021/215537
PCT Pub. Date: Oct. 28, 2021

(65) Prior Publication Data
US 2022/0340553 A1    Oct. 27, 2022

(30) Foreign Application Priority Data

Apr. 24, 2020 (JP) ................................ 2020-077487

(51) Int. Cl.
| | | |
|---|---|---|
| C07D 413/12 | (2006.01) | |
| A61K 31/506 | (2006.01) | |
| A61K 45/06 | (2006.01) | |
| A61P 25/08 | (2006.01) | |
| A61P 25/28 | (2006.01) | |
| C07D 401/12 | (2006.01) | |
| C07D 401/14 | (2006.01) | |
| C07D 403/12 | (2006.01) | |
| C07D 471/04 | (2006.01) | |

(52) U.S. Cl.
CPC .......... *C07D 413/12* (2013.01); *A61K 31/506* (2013.01); *A61K 45/06* (2013.01); *A61P 25/08* (2018.01); *A61P 25/28* (2018.01); *C07D 401/12* (2013.01); *C07D 401/14* (2013.01); *C07D 403/12* (2013.01); *C07D 471/04* (2013.01)

(58) Field of Classification Search
CPC .. C07D 413/12; C07D 401/12; C07D 401/14; C07D 403/12; C07D 471/04; A61K 31/506; A61K 45/06; A61P 25/08; A61P 25/28
See application file for complete search history.

(56) References Cited

U.S. PATENT DOCUMENTS

| | | | | |
|---|---|---|---|---|
| 11,401,261 | B2* | 8/2022 | Mori | .................... C07D 405/14 |
| 2007/0072832 | A1* | 3/2007 | Zhang | .................. C07D 405/12 |
| | | | | 549/403 |

FOREIGN PATENT DOCUMENTS

| | | |
|---|---|---|
| WO | WO 2018/098491 A1 | 5/2018 |
| WO | WO 2021/039968 A1 | 3/2021 |

OTHER PUBLICATIONS

Sulthana, M. T., et al. "Anti-HIV, Antitubercular and Antibacterial Activities of Novel 3-(Substituted Quinazolinylamino)-2-Phenyl Quinazolin-4(3H)Ones." Asian Journal of Chemistry, vol. 32, No. 2, 2020, pp. 281-286. asianpubs.org, https://doi.org/10.14233/ajchem.2020.22280. (Year: 2019).*

Morales-Mulia, M., et al. "Anxiolytic Effects of Ethanol Are Partially Related to a Reduced Expression of Adenylyl Cyclase 5 but Not to μ-Opioid Receptor Activation in Rat Nucleus Accumbens." Behavioural Brain Research, vol. 235, No. 2, Dec. 2012, pp. 189-194. (Year: 2012).*

Saravanan, Govindaraj, et al. Drug Development Research, vol. 80, No. 3, May 2019, pp. 368-385. DOI.org (Crossref), https://doi.org/10.1002/ddr.21511. (Year: 2019).*

Office Action issued on Dec. 24, 2021 in U.S. Appl. No. 17/410,338.
International Search Report issued Jul. 13, 2021 in PCT/JP2021/016498 filed Apr. 23, 2021, 4 pages.

Kandeel, M., "Syntheses of 4'-Nitrophenyl-2-Aminobenzthiazol-6-yl Sulfides and 4'-Nitrophenyl-2-Aminobenzthiazol-6-yl Sulfones Containing Dithiocarbamate", Phosphorus, Sulfur, and Silicon, vol. 48, 1990, pp. 149-155.

(Continued)

*Primary Examiner* — Clinton A Brooks
*Assistant Examiner* — Kyle Nottingham
(74) *Attorney, Agent, or Firm* — Oblon, McClelland, Maier & Neustadt, L.L.P.

(57) ABSTRACT

Provided is a 2-heteroaryl aminoquinazolinone derivative, which is a compound represented by formula (1):

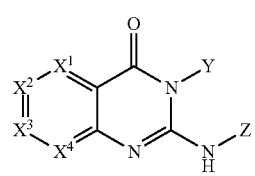

(1)

or a pharmaceutically acceptable salt thereof wherein $X^1$ represents $CR^1$ or N, $X^2$ represents $CR^2$ or N, $X^3$ represents $CR^3$ or N, $X^4$ represents $CR^4$ or N, Y represents optionally substituted $C_{1-6}$ alkyl, an optionally substituted $C_{3-10}$ alicyclic group, an optionally substituted 4- to 10-membered nitrogen-containing non-aryl heterocycle, optionally substituted $C_{6-10}$ aryl, or optionally substituted 5- to 10-membered heteroaryl, Z represents optionally substituted 6- to 10-membered heteroaryl, and $R^1$, $R^2$, $R^3$, and $R^4$ each independently represent a hydrogen atom, halogen, cyano, optionally substituted $C_{1-6}$ alkyl, optionally substituted $C_{1-6}$ alkoxy, or the like.

27 Claims, 2 Drawing Sheets

(56) References Cited

OTHER PUBLICATIONS

Gawad, N., et al., "Synthesis and antitumor activity of some 2,3-disubstituted quinazolin-4(3H)-ones and 4,6-disubstituted-1,2,3,4-tetrahydroquinazolin-2H-ones", European Journal of Medicinal Chemistry, vol. 45, 2010, pp. 6058-6067.

Kumar, S., et al., "Design, Synthesis and Anticonvulsant Evaluation of N-[(Substituted 1H-pyrazol-3-yl)amino]-2-(4-methylphenyl)quinazolin-4(3H)-one Derivatives", Asian Journal of Chemistry, vol. 29, No. 6, 2017, pp. 1375-1379.

El-Azab, A., et al., "Novel 4(3H)-quinazolinone analogs: synthesis and anticonvulsant activity", Medicinal Chemistry Research, vol. 22, 2013, pp. 2815-2827.

Gawad, N., et al., "Design, synthesis, and anticonvulsant activity of novel quinazolinone analogues", Medicinal Chemistry Research, vol. 20, 2011, pp. 1280-1286.

Pacico, N., et al., "New In Vitro Phenotypic Assay for Epilepsy: Fluorescent Measurements of Synchronized Neuronal Calcium Oscillations", PLOS One, vol. 9, No. 1, 2014, 9 total pages.

Scheffer, I., et al., "ILAE classification of the epilepsies: Position paper of the ILAE Commission for Classification and Terminology", Epilepsia, vol. 54, No. 4, 2017, pp. 512-521.

Aaberg, K., et al., Comorbidity and Childhood Epilepsy: A Nationwide Registry Study, Pediatrics, vol. 138, No. 3, 2016, pp. 1-10, 12 total pages.

Gaitatzis, A., et al., "The Epidemiology of the Comorbidity of Epilepsy in the General Population", Epilepsia, vol. 45, No. 12, 2004, pp. 1613-1622.

Selten, M., et al., "Inhibitory control of the excitatory/inhibitory balance in psychiatric disorders [version1; referees: 2 approved]", F1000Research, 2018, pp. 1-16.

Palop, J., et al., "Network abnormalitites and interneuron dysfunction in Alzheimer diseases", Nature Reviews, vol. 17, 2016, pp. 777-792.

Charvin, D., et al., "Therapeutic strategies for Parkinson disease: beyond dopaminergic drugs", Nature Reviews, vol. 17, 2018, pp. 804-822.

Extended European Search Report issued Apr. 25, 2024, in corresponding European Patent Application No. 21793331.6, 15 pages.

Sulthana et al., "Anti-HIV, Antitubercular and Antibacterial Activities of Novel 3-(Substituted Quinazolinylamino)-2-phenyl quinazolin-4(3H)ones", Asian J. Chem., Jan. 15, 2020, 32, 281-286, XP093151753.

Database Registry, Database accession No. 2199676-12-3: Pyrido[2,3-d]pyrimidin-4(3H)-one, 3-methyl-2-[[2-[(1-methyl-4-piperidinyl)methoxy]-3-pyridinyl]amino]-, Mar. 27, 2018, XP093151764.

D3 Database Registry, Database accession No. 2198334-25-5: Pyrido[3,4-d]pyrimidin-4(3H)-one, 3-methyl-2-[[2-[(1-methyl-4-piperidinyl)methoxy]-3-pyridinyl]amino]-, Mar. 25, 2018, XP093151767.

D4 Database Registry, Database accession No. 727391-19-7: 4(3H)-Quinazolinone, 2-[(4,6-dimethyl-2-pyrimidinyl)amino]-3-(3-methylbutyl)-, Aug. 16, 2004, XP093151772.

RN No. 2330681-38-2, et al., CAS STNext®, 2019, 27 pages.

\* cited by examiner

2-HETEROARYL AMINOQUINAZOLINONE DERIVATIVE

CROSS REFERENCE TO RELATED APPLICATIONS

This application is a national stage application of PCT/JP2021/016498, filed Apr. 23, 2021, which claims the benefits of priority to Japanese patent application 2020-077487, filed Apr. 24, 2020. The entire contents of both applications are incorporated by reference.

TECHNICAL FIELD

The present disclosure relates to a 2-heteroaryl aminoquinazolinone derivative that is useful as a medicament having an effect of suppressing neural circuit hyperexcitation, a pharmaceutically acceptable salt thereof, and a pharmaceutical composition comprising the same as an active ingredient.

BACKGROUND ART

It is known that abnormal excitation of the neural circuit of the brain is associated with various central nervous system diseases. For example, epilepsy is a chronic disease with repeated paroxysmal motor, conscious, or sensory abnormalities and behavioral abnormalities from hyperexcitation of the neural circuit. For the nervous system to function properly, excitation signals and inhibition signals need to be finely adjusted. Meanwhile, it is understood that hyperexcitation results from the breakdown in balance between excitation signals and inhibition signals in epilepsy. The causes of disease are wide ranging, roughly classified into genetic etiology where a known genetic abnormality is the direct cause, structural etiology where an abnormality in the brain structure is the cause, and the like (Non Patent Literature 1). For example, Dravet syndrome in which about 80% of patients have a pathogenic mutation in the SCN1A gene is a representative example of genetic etiology, and mesial temporal lobe epilepsy with hippocampal sclerosis is a representative example of structure etiology. Both types of epilepsy are diagnosed through a medical interview or brainwave examination. Hyperexcitation of the neural circuit is captured as an abnormal brainwave known as a spike or spike-and-wave.

Epileptic seizures are primary treated through medicament therapy. An antiepileptic medicament primarily inhibits excitation signals or enhances inhibition signals to suppress hyperexcitation of the neural circuit. Although many antiepileptic medicaments have been approved and commercially sold, one in three cases of epilepsy is refractory epilepsy exhibiting resistance to existing medicament therapy. Further, existing antiepileptic medicaments have a relatively narrow effective concentration (therapeutic range), so that an undesirable side effect (e.g., ataxia, sedation, dizziness, etc.) tends to manifest at a dose required to attain antiseizure activity. In addition, epilepsy patients are at high risk of complication such as a developmental disorder, mental disorder, or cognitive disorder (Non Patent Literatures 2 and 3). Existing medicaments do not have a therapeutic effect on such neurological/mental symptom complication.

An abnormality in the balance between excitation signals and inhibition signals in the neural circuit is understood to be in the background of the pathology of not only epilepsy, but also diseases associated with developmental disorders (autism spectrum disorder, Rett syndrome, Angelman syndrome, fragile X syndrome, attention deficit hyperactivity disorder, etc.), diseases associated with mental disorders (schizophrenia, bipolar disorder, depression, anxiety, obsessive-compulsive disorder, etc.), diseases associated with cognitive disorders (Alzheimer's disease, other dementia, Parkinson's disease, etc.), and various central nervous system diseases (Non Patent Literatures 4, 5, and 6). Thus, an agent that modulates hyperexcitation is expected to have an effect of improving the pathological condition in these diseases.

CITATION LIST

Non Patent Literature

[NPL 1] Scheffer, I E. et al. Epilepsia, (2017), 58(4), 512-521.
[NPL 2] Aaberg, K M. et al. Pediatrics, (2016), 138(3), e2016921.
[NPL 3] Gaitatzis, A. et al. Epilepsia, (2004), 45(12), 1613-1622.
[NPL 4] Selten, M. et al. F1000Research, (2018), 7.
[NPL 5] Palop, J J. et al. Nature Review Neuroscience, (2016), 17(12), 777-792.
[NPL 6] Charvin, D. et al. Nature Review Drug Discovery, (2018), 17(11), 804-822.

SUMMARY OF INVENTION

Solution to Problem

As a result of diligent study, the inventors have found that the compound represented by the following formula (1) exhibits a potent effect of suppressing neural circuit hyperexcitation to complete the present disclosure. The present disclosure provides a 2-heteroaryl aminoquinazolinone derivative represented by the following formula (1) (hereinafter, also referred to as the "compound of the present disclosure").

Specifically, the present disclosure is the following.

Item 1

A compound represented by formula (1):

[Chemical Formula 14]

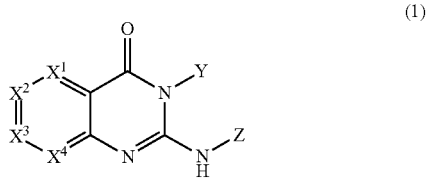

or a pharmaceutically acceptable salt thereof,
wherein
$X^1$ represents $CR^1$ or N,
$X^2$ represents $CR^2$ or N,
$X^3$ represents $CR^3$ or N,
$X^4$ represents $CR^4$ or N,
wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^2$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$, Y represents optionally substituted $C_{1-6}$ alkyl, an optionally substituted $C_{3-10}$ alicyclic group, an optionally substituted 4- to 10-membered non-aryl heterocycle, optionally substituted $C_{6-10}$ aryl, or optionally substituted 5- to 10-membered heteroaryl, Z represents optionally substituted 5- to 10-membered heteroaryl, $R^1$, $R^2$, $R^3$, and $R^4$ each independently represent a hydrogen atom, halogen, cyano, $C_{1-6}$ alkylsulfonyl, —$SO_2$—$NR^5R^6$, —$NR^7R^8$, —$NR^9$—C(=O)$R^{10}$, —$NR^{11}$—$SO_2$—$R^{12}$, —C(=O)$NR^{13}R^{14}$, —C(=O)$OR^{15}$, optionally substituted $C_{1-6}$ alkyl, or optionally substituted $C_{1-6}$ alkoxy, $R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, alkoxy, and a 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocyclic group (wherein the ring is optionally substituted with 1 to 5 of the same or different substituents selected from the group consisting of halogen, hydroxy, $C_{1-6}$ alkyl, and $C_{1-6}$ alkoxy), provided that the compound is not:

a compound represented by formula (W-1):

[Chemical Formula 15]

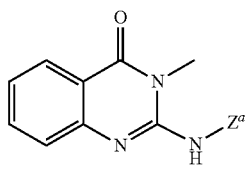

(W-1)

wherein

V is optionally substituted 5- to 10-membered heteroaryl;

a compound represented by formula (W-2):

[Chemical Formula 16]

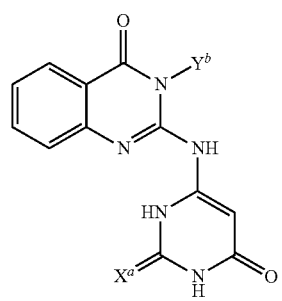

(W-2)

wherein $X^a$ is O or S, and $Y^b$ is ethyl, unsubstituted phenyl, 4-chlorophenyl, or 4-methoxyphenyl;

a compound represented by formula (W-3):

[Chemical Formula 17]

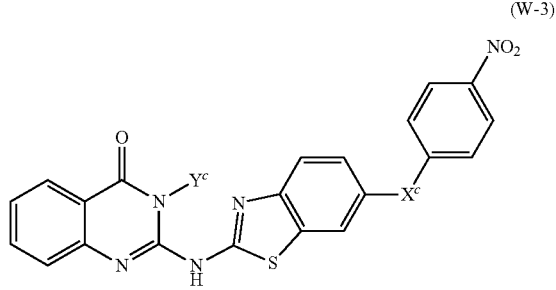

(W-3)

wherein $X^c$ is —S— or —$SO_2$—, and $Y^c$ is unsubstituted phenyl, 4-chlorophenyl, or 4-methoxyphenyl;

a compound represented by formula (W-4):

[Chemical Formula 18]

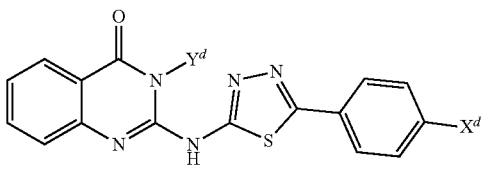

(W-4)

wherein $X^d$ is methoxy, chloro, or dimethylamino, and $Y^d$ is ethyl, unsubstituted phenyl, 4-chlorophenyl, or 4-methoxyphenyl;

2-{(4,6-dimethylpyrimidin-2-yl)amino}-3-isopentylquinazolin-4(3H)-one;

3-(pyridin-2-yl)-2-(pyridin-2-ylamino)quinazolin-4(3H)-one;

3-methyl-2-{[2-((1-methylpiperidin-4-yl)methoxy)pyridin-3-yl]amino}pyrido[3,4-d]pyrimidin-4(3H)-one; or 3-methyl-2-{[2-((1-methylpiperidin-4-yl)methoxy)pyridin-3-yl]amino}pyrido[2,3-d]pyrimidin-4(3H)-one.

Item 2

The compound or the pharmaceutically acceptable salt thereof according to item 1, wherein $X^1$ is $CR^1$.

Item 3

The compound or the pharmaceutically acceptable salt thereof according to item 1 or 2, wherein $X^2$ is $CR^2$.

Item 4

The compound or the pharmaceutically acceptable salt thereof according to any one of items 1 to 3, wherein $X^3$ is $CR^3$.

Item 5

The compound or the pharmaceutically acceptable salt thereof according to any one of items 1 to 4, wherein $X^4$ is $CR^4$.

Item 6

The compound or the pharmaceutically acceptable salt thereof according to any one of items 1 to 5, wherein $R^1$, $R^2$, $R^3$, and $R^4$ are each independently a hydrogen atom, halogen, cyano, $C_{1-6}$ alkoxy, or $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

Item 7

The compound or the pharmaceutically acceptable salt thereof according to any one of items 1 to 5, wherein $R^1$, $R^3$, and $R^4$ are all hydrogen atoms, and $R^2$ is a hydrogen atom, halogen, cyano, $C_{1-6}$ alkyl (wherein the alkyl is optionally substituted with 1 to 3 fluorine or a methoxy group), or $C_{1-6}$ alkoxy.

Item 8

The compound or the pharmaceutically acceptable salt thereof according to any one of items 1 to 5, wherein $R^1$, $R^3$, and $R^4$ are all hydrogen atoms, and $R^2$ is a hydrogen atom, fluorine, chloro, cyano, or $C_{1-6}$ alkyl (wherein the alkyl is optionally substituted with 1 to 3 fluorine or a methoxy group).

Item 9

The compound or the pharmaceutically acceptable salt thereof according to any one of items 1 to 5, wherein $R^1$, $R^3$, and $R^4$ are all hydrogen atoms, and $R^2$ is fluorine or cyano.

Item 10

The compound or the pharmaceutically acceptable salt thereof according to any one of items 1 to 9, wherein Y is
(1) $C_{1-6}$ alkyl optionally substituted with 1 to 3 of the same or different substituents selected from the group consisting of halogen, hydroxy, amino, dimethylamino, a $C_{3-6}$ alicyclic group, a 4- to 10-membered nitrogen-containing non-aryl heterocyclic group, $C_{1-5}$ alkoxy, $C_{6-10}$ aryl (wherein the alicyclic group, the nitrogen-containing non-aryl heterocyclic group, the alkoxy, and the aryl group are each independently optionally substituted with 1 to 3 of the same or different substituents selected from the group consisting of halogen, cyano, a C alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy),
(2) a $C_{3-10}$ alicyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, a 4- to 10-membered nitrogen-containing non-aryl heterocyclic group, $C_{1-6}$ alkoxy, aryl (wherein the alicyclic group, the nitrogen-containing non-aryl heterocyclic group, the alkoxy, and the aryl group are each independently optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a C alicyclic group, $C_{1-6}$, alkyl optionally substituted with 1 to 5 fluorine, and $C_{1-6}$ alkoxy),
(3) a 4- to 10-membered non-aryl heterocyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, $C_{1-6}$ alkoxy, and $C_{6-10}$ aryl (wherein the alicyclic group, the alkoxy, and the aryl group are each independently optionally substituted with 1 to 3 of the same or different substituents selected from the group consisting of halogen, cyano, a alicyclic group, $C_{1-6}$ alkyl optionally substituted with 1 to 5 fluorine, and $C_{1-6}$ alkoxy),
(4) $C_{6-10}$ aryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy), or
(5) 5- to 10-membered heteroaryl optionally substituted with 1 to 3 of the same or different substituents selected from the group consisting of halogen, cyano, dimethylamino, alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

Item 11

The compound or the pharmaceutically acceptable salt thereof according to any one of items 1 to 9, wherein Y is
(1) $C_{1-3}$ alkyl optionally substituted with 1 to 3 of the same or different substituents selected from the group consisting of fluorine, a $C_{3-6}$ alicyclic group, a 5- or 6-membered nitrogen-containing non-aryl heterocyclic group, phenyl (wherein the alicyclic group, the nitrogen-containing non-aryl heterocycle, and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
(2) a $C_{3-6}$ alicyclic group optionally substituted with 1 to 3 of the same or different substituents selected from the group consisting of fluorine, amino, dimethylamino, $C_{1-3}$ alkyl optionally substituted with 1 to 3 fluorine, a 5- to 6-membered nitrogen-containing non-aryl heterocyclic group, phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy), (3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine, (4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or (5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine.

Item 11a

The compound or the pharmaceutically acceptable salt thereof according to any one of items 1 to 9, wherein Y is (1) $C_{1-3}$ alkyl optionally substituted with 1 to 3 of the same or different substituents selected from the group consisting of fluorine, a $C_{3-6}$ alicyclic group, a 5- or 6-membered nitrogen-containing non-aryl heterocyclic group, phenyl (wherein the alicyclic group, the nitrogen-containing non-aryl heterocycle, and the phenyl group are each independently optionally substituted with 1 to 3 of the same or different substituents selected from the group consisting of fluorine, cyano, alkyl optionally substituted with 1 to 3 fluorine, and methoxy), and 5-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy), (2) a $C_{5-6}$ alicyclic group or phenylcyclopropyl wherein the $C_{5-6}$ alicyclic group or phenylcyclopropyl is optionally substituted with 1 to 3 of the same or different substituents selected from the group consisting of fluorine, amino, dimethylamino, $C_{2-3}$ alkyl optionally substituted with to 3 fluorine, a 5- to 6-membered nitrogen-containing non-aryl heterocyclic group, phenyl (wherein the phenyl group is optionally substituted with 1 to 3 of the same or different substituents selected from the group consisting of fluorine, cyano, alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy), (3) a 4- to 6-membered nitrogen-containing non-aryl heterocyclic group, phenyloxetanyl, or tetrahydropyranyl wherein the 4- to 6-membered nitrogen-containing non-aryl heterocyclic group, phenyloxetanyl, or tetrahydropyranyl is optionally substituted with 1 to 3 of the same or different substituents selected from the group consisting of fluorine, amino, dimethylamino, $C_{2-3}$ alkyl optionally substituted with 1 to 3 fluorine, and phenyl (wherein the phenyl group is optionally substituted with 1 to 3 of the same or different substituents selected from the group consisting of fluorine, cyano, $C_{2-3}$ alkyl optionally substituted with 1 to 3 fluorine, and methoxy), (4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or (5) 6-membered heteroaryl optionally substituted with 1 to 3 of the same or different substituents selected from the group consisting of halogen, cyano, alkoxy, and $C_{1-3}$ alkyl optionally substituted with 1 to 3 fluorine.

Item 12

The compound or the pharmaceutically acceptable salt thereof according to any one of items 1 to 9, wherein Y is (1) $C_{1-3}$ alkyl optionally substituted with 1 to 3 fluorine, (2) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine, (3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine, (4) phenyl optionally substituted with 1 to 3 of the same or different substituents selected from the group consisting of halogen, cyano, dimethylamino, $C_{1-3}$ alkoxy, and $C_{1-5}$ alkyl optionally substituted with 1 to 3 fluorine, or (5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine.

Item 13

The compound or the pharmaceutically acceptable salt thereof according to any one of items 1 to 9, wherein Y is (1) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine, (2) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine, (3) phenyl optionally substituted with 1 to 3 of the same or different substituents selected from the group consisting of halogen, cyano, methoxy, and $C_{1-3}$ alkyl optionally substituted with 1 to 3 fluorine, or (4) 5- or 6-membered heteroaryl optionally substituted with 1 to 3 of the same or different substituents selected from the group consisting of halogen, cyano, methoxy, and $C_{1-3}$ alkyl optionally substituted with 1 to 3 fluorine.

Item 14

The compound or the pharmaceutically acceptable salt thereof according to any one of items 1 to 9, wherein Y is
(1) phenyl optionally substituted with 1 to 2 of the same or different substituents selected from the group consisting of fluorine, cyano, methoxy, and methyl, or
(2) 5- or 6-membered heteroaryl optionally substituted with 1 to 2 of the same or different substituents selected from the group consisting of fluorine, cyano, methoxy, and methyl.

Item 14a

The compound or the pharmaceutically acceptable salt thereof according to any one of items 1 to 9, wherein Y is
(1) phenyl optionally substituted with 1 to 2 of the same or different substituents selected from the group consisting of fluorine, cyano, methoxy, and methyl, or
(2) 6-membered heteroaryl optionally substituted with 1 to 2 of the same or different substituents selected from the group consisting of fluorine, cyano, methoxy, and methyl.

Item 15

The compound or the pharmaceutically acceptable salt thereof according to any one of items 1 to 14, 11a, and 14a, wherein Z is 5- to 10-membered heteroaryl optionally substituted with 1 to 3 of the same or different substituents selected from the group consisting of halogen, cyano, dimethylamino, $C_{1-6}$ alkoxy, and alkyl (wherein the alkoxy and the alkyl are each independently optionally substituted with 1 to 3 of the same or different substituents selected from the group consisting of halogen, hydroxy, and $C_{1-3}$ alkoxy).

Item 15a

The compound or the pharmaceutically acceptable salt thereof according to any one of items 1 to 14, 11a, and 14a, wherein Z is 6- to 10-membered heteroaryl optionally substituted with 1 to 3 of the same or different substituents selected from the group consisting of halogen, cyano, $C_{2-6}$ alkoxy, and $C_{1-5}$ alkyl (wherein the alkoxy and the alkyl are each independently optionally substituted with 1 to 3 of the same or different substituents selected from the group consisting of halogen, hydroxy, and $C_{1-6}$ alkoxy).

Item 15b

The compound or the pharmaceutically acceptable salt thereof according to any one of items 1 to 14, 11a, and 14a, wherein Z is 6- to 10-membered heteroaryl, thienyl, pyrrolyl, thiazolyl, isothiazolyl, isoxazolyl, or thiadiazolyl wherein the 6- to 10-membered heteroaryl, thienyl, pyrrolyl, thiazolyl, isothiazolyl, isoxazolyl, or thiadiazolyl is optionally substituted with 1 to 3 of the same or different substituents selected from the group consisting of fluorine, cyano, $C_{2-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-5}$ alkoxy).

Item 16

The compound or the pharmaceutically acceptable salt thereof according to any one of items 1 to 14, 11a, and 14a, wherein Z is 6- to 10-membered heteroaryl optionally substituted with 1 to 3 of the same or different substituents selected from the group consisting of fluorine, chloro, cyano, $C_{1-5}$ alkoxy, and $C_{1-3}$ alkyl optionally substituted with 1 to 3 fluorine.

Item 17

The compound or the pharmaceutically acceptable salt thereof according to any one of items 1 to 14, 11a, and 14a, wherein Z is pyridyl, pyrimidinyl, indazolyl, or imidazopyridyl wherein the pyridyl, pyrimidinyl, indazolyl, or imidazopyridyl is optionally substituted with 1 to 3 of the same or different substituents selected from the group consisting of fluorine, chloro, cyano, methoxy, and alkyl optionally substituted with 1 to 3 fluorine.

Item 18

The compound or the pharmaceutically acceptable salt thereof according to any one of items 1 to 14, 11a, and 14a, wherein Z is pyridyl optionally substituted with 1 to 3 of the same or different substituents selected from the group consisting of fluorine, chloro, cyano, and $C_{1-3}$ alkyl optionally substituted with 1 to 3 fluorine.

Item 19

The compound or the pharmaceutically acceptable salt thereof according to item 1, wherein
$X^1$ is $CR^1$ or N,
$X^2$ is $CR^2$ or N,
$X^3$ is $CR^3$ or N,
$X^4$ is $CR^4$ or N,
wherein (1) if $X^1$ is N, $X^2$ is $CR^2$, $X^3$ is $CR^1$, and $X^4$ is $CR^4$, (2) if $X^2$ is N, $X^1$ is $CR^1$, $X^1$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
$R^1$, $R^2$, $R^3$, and $R^4$ are each independently
(1) a hydrogen atom,
(2) halogen,
(3) cyano,
(4) $C_{1-6}$ alkoxy, or
(5) $C_{1-6}$ alkyl (wherein the alkyl is optionally substituted with 1 to 3 of the same or different substituents selected from the group consisting of halogen, hydroxy, and $C_{1-6}$ alkoxy),
Y is
(1) $C_{1-6}$ alkyl optionally substituted with 1 to 3 of the same or different substituents selected from the group consisting of halogen, hydroxy, amino, dimethylamino, a $C_{3-6}$ alicyclic group, a 4- to 10-membered nitrogen-containing non-aryl heterocyclic group, $C_{1-6}$ alkoxy, $C_{6-10}$ aryl (wherein the alicyclic group, the nitrogen-containing non-aryl heterocycle, the alkoxy, and the aryl group are each independently optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy),
(2) a $C_{3-10}$ alicyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, a 4- to 10-membered nitrogen-containing non-aryl heterocyclic group, $C_{1-6}$ alkoxy, $C_{6-10}$ aryl (wherein the alicyclic group, the nitrogen-containing non-aryl heterocycle, the alkoxy, and the aryl group are each independently optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy),
(3) a 4- to 10-membered nitrogen-containing non-aryl heterocyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, and $C_{1-6}$ alkoxy,
(4) $C_{6-10}$ aryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy), or
(5) 5- to 10-membered heteroaryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy), and
Z is 6- to 10-membered heteroaryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

Item 20

The compound or the pharmaceutically acceptable salt thereof according to item 1, wherein
$X^1$ is $CR^1$,
$K^2$ is $CR^2$,
$K^3$ is $CR^3$,
$K^4$ is $CR^4$,
$R^1$, $R^3$, and $R^4$ are all hydrogen atoms,
$R^2$ is
(1) a hydrogen atom,
(2) fluorine,
(3) chloro,
(4) cyano
(5) $C_{1-6}$ alkoxy, or
(6) $C_{1-3}$ alkyl (wherein the alkyl is optionally substituted with 1 to 3 of the same or different substituents selected from the group consisting of halogen, hydroxy, and $C_{1-6}$ alkoxy),
Y is
(1) $C_{1-3}$ alkyl optionally substituted with 1 to 3 of the same or different substituents selected from the group consisting of fluorine, a alicyclic group, a 5- or 6-membered nitrogen-containing non-aryl heterocyclic group, phenyl (wherein the alicyclic group, the nitrogen-containing non-aryl heterocyclic group, and the phenyl group are each independently optionally substituted with 1 to 3 of the same or different substituents selected from the group consisting of fluorine, cyano, alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, alkyl optionally substituted with 1 to 3 fluorine, and methoxy),
(2) a $C_{3-6}$ alicyclic group optionally substituted with 1 to 3 of the same or different substituents selected from the group consisting of fluorine, amino, dimethylamino, $C_{1-3}$ alkyl optionally substituted with 1 to 3 fluorine, a 5- to 6-membered nitrogen-containing non-aryl heterocyclic group, phenyl (wherein the nitrogen-containing non-aryl heterocyclic group and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
(3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
(4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or
(5) 5- or 6-membered heteroaryl optionally substituted with 1 to 3 of the same or different substituents selected from the group consisting of halogen, cyano, dimethylamino, $C_{1-3}$ alkoxy, and alkyl optionally substituted with 1 to 3 fluorine, and
Z is 6- to 10-membered heteroaryl, which is optionally substituted with 1 to 3 of the same or different substituents selected from the group consisting of fluorine, chloro, cyano, $C_{1-6}$ alkoxy, and $C_{1-3}$ alkyl optionally substituted with 1 to 3 fluorine or 1 $C_{1-6}$ alkoxy, and comprises 1 to 2 atoms independently selected from the group consisting of a nitrogen atom and an oxygen atom.

Item 21

The compound or the pharmaceutically acceptable salt thereof according to item 1, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) alkyl optionally substituted with 1 to 3 fluorine,
(2) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine,
(3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
(4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or
(5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and
Z is 6- to 10-membered heteroaryl, which is optionally substituted with 1 to 3 of the same or different substituents selected from the group consisting of fluorine, chloro, cyano, $C_{1-6}$ alkoxy, and $C_{1-3}$ alkyl optionally substituted with 1 to 3 fluorine and comprises 1 to 2 atoms independently selected from the group consisting of a nitrogen atom and an oxygen atom.

Item 22

The compound or the pharmaceutically acceptable salt thereof according to item 1, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine,
(2) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
(3) phenyl optionally substituted with 1 to 3 of the same or different substituents selected from the group consisting of halogen, cyano, methoxy, and $C_{1-3}$ alkyl optionally substituted with 1 to 3 fluorine, or
(4) 5- or 6-membered heteroaryl optionally substituted with 1 to 3 of the same or different substituents selected from the group consisting of halogen, cyano, methoxy, and $C_{1-3}$ alkyl optionally substituted with 1 to 3 fluorine, and
Z is pyridyl, pyrimidinyl, indazolyl, or imidazopyridyl wherein the pyridyl, pyrimidinyl, indazolyl, or imidazopyridyl is optionally substituted with 1 to 3 of the same or different substituents selected from the group consisting of fluorine, chloro, cyano, methoxy, and $C_{1-3}$ alkyl optionally substituted with 1 to 3 fluorine.

Item 23

The compound or the pharmaceutically acceptable salt thereof according to item 1, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) phenyl optionally substituted with 1 to 2 of the same or different substituents selected from the group consisting of fluorine, cyano, methoxy, and methyl, or
(2) 5- or 6-membered heteroaryl optionally substituted with 1 to 2 of the same or different substituents selected from the group consisting of fluorine, cyano, methoxy, and methyl, and
Z is pyridyl optionally substituted with 1 to 3 of the same or different substituents selected from the group consisting of fluorine, chloro, cyano, and alkyl optionally substituted with 1 to 3 fluorine.

Item 24

The compound or the pharmaceutically acceptable salt thereof according to item 1, wherein
$X^1$ is $CR^1$,
$X^z$ is $CR^1$,
$X^3$ is $CR^1$,
$X^4$ is $CR^4$,
$R^1$, $R^3$, and $R^4$ are all hydrogen atoms,
$R^2$ is fluorine or cyano,
Y is
(1) $C_{1-3}$ alkyl optionally substituted with 1 to 3 fluorine,
(2) a $C_{5-6}$ alicyclic group or phenylcyclopropyl wherein the $C_{5-6}$ alicyclic group or phenylcyclopropyl is optionally substituted with 1 to 3 of the same or different substituents selected from the group consisting of fluorine, amino, dimethylamino, and $C_{2-3}$ alkyl optionally substituted with 1 to 3 fluorine,
(3) a 4- to 6-membered nitrogen-containing non-aryl heterocyclic group, phenyloxetanyl, or tetrahydropyranyl wherein the 4- to 6-membered nitrogen-containing non-aryl heterocyclic group, phenyloxetanyl, or tetrahydropyranyl is optionally substituted with 1 to 3 of the same or different substituents selected from the group consisting of fluorine, amino, dimethylamino, $C_{2-3}$ alkyl optionally substituted with 1 to 3 fluorine, and phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy), (4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or
(5) 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and Z is 6- to 10-membered heteroaryl optionally substituted with 1 to 3 of the same or different substituents selected from the group consisting of fluorine, chloro, cyano, $C_{2-6}$ alkoxy, and $C_{1-3}$ alkyl optionally substituted with 1 to 3 fluorine.

Item 25

The compound or the pharmaceutically acceptable salt thereof according to item 1, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) $C_{1-3}$ alkyl optionally substituted with 1 to 3 fluorine,
(2) a $C_{5-6}$ alicyclic group or phenylcyclopropyl wherein the $C_{5-6}$ alicyclic group or phenylcyclopropyl is optionally substituted with 1 to 3 of the same or different substituents selected from the group consisting of fluorine, amino, dimethylamino, and $C_{2-3}$ alkyl optionally substituted with 1 to 3 fluorine,
(3) a 4- to 6-membered nitrogen-containing non-aryl heterocyclic group, phenyloxetanyl, or tetrahydropyranyl wherein the 4- to 6-membered nitrogen-containing non-aryl heterocyclic group, phenyloxetanyl, or tetrahydropyranyl is optionally substituted with 1 to 3 of the same or different substituents selected from the group consisting of fluorine, amino, dimethylamino, $C_{2-3}$ alkyl optionally substituted with 1 to 3 fluorine, and phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy),
(4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or
(5) 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and Z is 6- to 10-membered heteroaryl, thienyl, pyrrolyl, thiazolyl, isothiazolyl, isoxazolyl, or thiadiazolyl wherein the 6- to 10-membered heteroaryl, thienyl, pyrrolyl, thiazolyl, isothiazolyl, isoxazolyl, or thiadiazolyl is optionally substituted with 1 to 3 of the same or different substituents selected from the group consisting of fluorine, cyano, $C_{2-6}$ alkoxy, and $C_{1-3}$ alkyl optionally substituted with 1 to 3 fluorine.

Item 26

The compound or the pharmaceutically acceptable salt thereof according to item 1, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) a $C_{5-6}$ alicyclic group optionally substituted with 1 to 3 of the same or different substituents selected from the group consisting of fluorine, amino, dimethylamino, and $C_{2-3}$ alkyl optionally substituted with 1 to 3 fluorine,
(2) a 5- or 6-membered nitrogen-containing non-aryl heterocyclic group optionally substituted with 1 to 3 of the same or different substituents selected from the group consisting of fluorine, amino, dimethylamino, and $C_{2-3}$ alkyl optionally substituted with 1 to 3 fluorine,
(3) phenyl optionally substituted with 1 to 3 of the same or different substituents selected from the group consisting of halogen, cyano, methoxy, and $C_{1-3}$ alkyl optionally substituted with 1 to 3 fluorine, or
(4) 6-membered heteroaryl optionally substituted with 1 to 3 of the same or different substituents selected from the group consisting of halogen, cyano, methoxy, and $C_{1-3}$ alkyl optionally substituted with 1 to 3 fluorine, and Z is pyridyl, pyrimidinyl, indazolyl, or imidazopyridyl wherein the pyridyl, pyrimidinyl, indazolyl, or imidazopyridyl is optionally substituted with 1 to 3 of the same or different substituents selected from the group consisting of fluorine, chloro, cyano, and $C_{1-3}$ alkyl optionally substituted with 1 to 3 fluorine.

Item 27

The compound or the pharmaceutically acceptable salt thereof according to item 1, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) phenyl optionally substituted with 1 to 2 of the same or different substituents selected from the group consisting of fluorine, cyano, methoxy, and methyl, or
(2) 6-membered heteroaryl optionally substituted with 1 to 2 of the same or different substituents selected from the group consisting of fluorine, cyano, methoxy, and methyl, and Z is pyridyl optionally substituted with 1 to 3 of the same or different substituents selected from the group consisting of fluorine, chloro, cyano, and $C_{1-3}$ alkyl optionally substituted with 1 to 3 fluorine.

Item 24

The compound or the pharmaceutically acceptable salt thereof according to items 1 to 23, 11a, 14a, 15a, or 15b, selected from the following compounds:
4-oxo-3-phenyl-2-(pyridin-3-ylamino)-3,4-dihydroquinazoline-6-carbonitrile (Example 3),
6-fluoro-2-((5-fluoropyridin-3-yl)amino)-3-(o-tolyl)quinazolin-4(3H)-one (Example 4), 6-chloro-2-((2-methoxypyridin-3-yl)amino)-3-phenylquinazolin-4(3H)-one (Example 10),
6-fluoro-3-phenyl-2-(pyridin-3-ylamino)quinazolin-4(3H)-one (Example 12),
3-phenyl-2-(pyridin-3-ylamino)quinazolin-4(3H)-one (Example 14),
6-chloro-3-(2-chlorophenyl)-2-(pyridin-3-ylamino)quinazolin-4(3H)-one (Example 15),
6-chloro-3-phenyl-2-(pyridin-3-ylamino)quinazolin-4(3H)-one (Example 31),
6,8-difluoro-3-phenyl-2-(pyridin-3-ylamino)quinazolin-4(3H)-one (Example 32),
6-fluoro-3-(pyridin-3-yl)-2-(pyridin-3-ylamino)quinazolin-4(3H)-one (Example 35),
6-chloro-3-phenyl-2-(pyrazin-2-ylamino)quinazolin-4(3H)-one (Example 38),
6-fluoro-3-phenyl-2-(pyrazin-2-ylamino)quinazolin-4(3H)-one (Example 39),
6-fluoro-2-((5-fluoropyridin-3-yl)amino)-3-phenylquinazolin-4(3H)-one (Example 40),
5-((6-chloro-4-oxo-3-phenyl-3,4-dihydroquinazolin-2-yl)amino)nicotinonitrile (Example 41),
6-methyl-3-phenyl-2-(pyridin-3-ylamino)quinazolin-4(3H)-one (Example 42),
2-((5-chloropyridin-3-yl)amino)-6-fluoro-3-phenylquinazolin-4(3H)-one (Example 45),
6-chloro-3-(2-fluorophenyl)-2-(pyridin-3-ylamino)quinazolin-4(3H)-one (Example 51),
2-((1-methyl-1H-indazol-6-yl)amino)-3-phenylquinazolin-4(3H)-one (Example 54),
2-(imidazo[1,5-a]pyridin-8-ylamino)-3-phenylquinazolin-4(3H)-one (Example 69),
3-(4-methoxy-2-methylphenyl)-4-oxo-2-(pyridin-3-ylamino)-3,4-dihydroquinazoline-6-carbonitrile (Example 102),
3-(5-fluoro-2-methylphenyl)-4-oxo-2-(pyridin-3-ylamino)-3,4-dihydroquinazoline-6-carbonitrile (Example 104),
6-fluoro-2-(pyridin-3-ylamino)-3-(p-tolyl)quinazolin-4(3H)-one (Example 105),
6-fluoro-2-(pyridin-3-ylamino)-3-(o-tolyl)quinazolin-4(3H)-one (Example 107),
6-fluoro-3-(2-fluorophenyl)-2-(pyridin-3-ylamino)quinazolin-4(3H)-one (Example 108),
4-oxo-2-(pyridin-3-ylamino)-3-(o-tolyl)-3,4-dihydroquinazoline-6-carbonitrile (Example 109),
6-fluoro-3-(2-fluorophenyl)-2-((5-fluoropyridin-3-yl)amino)quinazolin-4(3H)-one (Example 111),
2-((5-fluoropyridin-3-yl)amino)-4-oxo-3-phenyl-3,4-dihydroquinazoline-6-carbonitrile (Example 112),
3-(2-fluorophenyl)-2-((5-fluoropyridin-3-yl)amino)-4-oxo-3,4-dihydroquinazoline-6-carbonitrile (Example 113),
2-((5-fluoropyridin-3-yl)amino)-4-oxo-3-(o-tolyl)-3,4-dihydroquinazoline-6-carbonitrile (Example 114),
6-fluoro-2-((4-fluoropyridin-2-yl)amino)-3-phenylquinazolin-4(3H)-one (Example 127),
6-fluoro-2-((5-methylpyridin-2-yl)amino)-3-phenylquinazolin-4(3H)-one (Example 137),
6-fluoro-2-((2-fluoropyridin-4-yl)amino)-3-phenylquinazolin-4(3H)-one (Example 141),
6-fluoro-3-(2-methoxyphenyl)-2-(pyridin-3-ylamino)quinazolin-4(3H)-one (Example 142), and
3-(2-chlorophenyl)-6-fluoro-2-(pyridin-3-ylamino)quinazolin-4(3H)-one (Example 145).

Item 25

A medicament comprising the compound or the pharmaceutically acceptable salt thereof according to any one of items 1 to 24, 11a, 14a, 15a, and 15b as an active ingredient.

Item 26

The medicament according to item 25, which is a therapeutic medicament or a prophylactic medicament for epilepsy or a developmental disorder.

Item 27

A therapeutic medicament or prophylactic medicament for a disorder or disease associated with an abnormal nerve excitation comprising the compound or the pharmaceutically acceptable salt thereof according to any one of items 1 to 26, 11a, 14a, 15a, and 15b as an active ingredient.

Item 28

The therapeutic medicament or prophylactic medicament according to item 27, wherein the disorder or disease associated with an abnormal nerve excitation is a disease related to epilepsy or a developmental disorder.

Item 29

A pharmaceutical composition comprising the compound or the pharmaceutically acceptable salt thereof according to any one of items 1 to 24, 11a, 14a, 15a, and 15b.

Item 30

The pharmaceutical composition according to item 29 for the treatment or prophylaxis of a disorder or disease associated with an abnormal nerve excitation.

Item 31

The pharmaceutical composition according to item 29 or 30, which is a therapeutic medicament or a prophylactic medicament for epilepsy or a developmental disorder.

Item 32

A method for treating or preventing a disorder or disease associated with an abnormal nerve excitation, comprising administering a therapeutically or prophylactically effective amount of the compound or the pharmaceutically acceptable salt thereof according to any one of items 1 to 24, 11a, 14a, 15a, and 15b to a patient in need thereof.

Item 33

Use of the compound or the pharmaceutically acceptable salt thereof according to any one of items 1 to 24, 11a, 14a, 15a, and 15b for the manufacture of a therapeutic medicament or prophylactic medicament for a disorder or disease associated with an abnormal nerve excitation.

Item 34

The compound or the pharmaceutically acceptable salt thereof according to any one of items 1 to 24, 11a, 14a, 15a, and 15b for use in the treatment or prophylaxis of a disorder or disease associated with an abnormal nerve excitation.

Item 35

A pharmaceutical composition comprised of the compound or the pharmaceutically acceptable salt thereof according to any one of items 1 to 24, 11a, 14a, 15a, and 15b in combination with at least one agent selected from agents classified as an antiepileptic medicament, an antidepressant, an anxiolytic, or an antipsychotic medicament.

Item 36

A pharmaceutical composition comprising the compound or the pharmaceutically acceptable salt thereof according to any one of items 1 to 24, 11a, 14a, 15a, and 15b for the treatment or prophylaxis of a disorder or disease associated with an abnormal nerve excitation concomitantly used with at least one agent selected from agents classified as an antiepileptic medicament, an antidepressant, an anxiolytic, or an antipsychotic medicament.

Item 37

A medicament, which is a therapeutic medicament or prophylactic medicament for a disorder or disease associated with an abnormal nerve excitation, comprising, as an active ingredient, a compound represented by

[Chemical Formula 19]

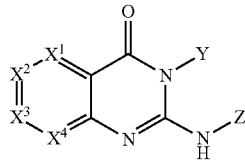

(1)

or a pharmaceutically acceptable salt thereof
wherein
- $X^1$ represents $CR^1$ or N,
- $X^1$ represents $CR^2$ or N,
- $X^1$ represents $CR^3$ or N,
- $X^4$ represents $CR^4$ or N,
- wherein (1) if $X^1$ is N, $X^2$ is $CR^2$, $X^3$ is $CR^1$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
- Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
- Z represents optionally substituted 5- to 10-membered heteroaryl,
- $R^1$, $R^2$, $R^3$, and $R^4$ each independently represent a hydrogen atom, halogen, cyano, $C_{1-6}$ alkylsulfonyl, —$SO_2$—$NR^5R^6$, —$NR^7R^8$, —$NR^9$—$C(=O)R^{10}$, —$NR^{11}$—$SO_2$—$R^{12}$, —$C(=O)NR^{13}R^{14}$, —$C(=O)OR^{15}$, optionally substituted $C_{1-6}$ alkyl, or optionally substituted $C_{1-6}$ alkoxy, and
- $R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and a 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, $C_{1-6}$ alkyl, and $C_{1-6}$ alkoxy).

Item 38

A therapeutic medicament or prophylactic medicament for a disorder or disease associated with an abnormal nerve excitation, comprising, as an active ingredient, a compound represented by

[Chemical Formula 20]

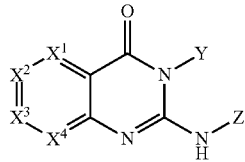

(1)

or a pharmaceutically acceptable salt thereof
wherein
- $X^1$ represents $CR^1$ or N,
- $X^2$ represents $CR^2$ or N,
- $X^3$ represents $CR^3$ or N,
- $K^4$ represents $CR^4$ or N,
- wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
- Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
- Z represents optionally substituted 5- to 10-membered heteroaryl,
- $R^1$, $R^2$, $R^3$, and $R^4$ each independently represent a hydrogen atom, halogen, cyano, $C_{1-6}$ alkylsulfonyl, —$SO_2$—$NR^5R^6$, —$NR^7R^8$, —$NR^9$—$C(=O)R^{10}$, —$NR^{11}$—$SO_2$—$C(=O)NR^{13}R^{14}$, —$C(=O)OR^{15}$, optionally substituted $C_{1-6}$ alkyl, or optionally substituted $C_{1-6}$ alkoxy, and
- $R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and a 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, $C_{1-6}$ alkyl, and alkoxy).

Item 39

A pharmaceutical composition, which is a therapeutic medicament or prophylactic medicament for a disorder or disease associated with an abnormal nerve excitation, comprising a compound represented by

[Chemical Formula 21]

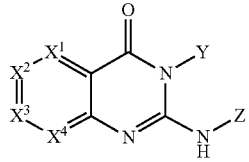

(1)

or a pharmaceutically acceptable salt thereof
wherein
$X^1$ represents $CR^1$ or N,
$X^2$ represents $CR^2$ or N,
$X^3$ represents $CR^3$ or N,
$X^4$ represents $CR^4$ or N,
wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^1$, and $X^4$ is $CR^4$, and (4) if $X^4$ is N, $X^1$ is $CR^1$, $X^2$ is $CR^2$, and $X^3$ is $CR^3$,
Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
Z represents optionally substituted 5- to 10-membered heteroaryl,
$R^1$, $R^2$, $R^3$, and $R^4$ each independently represent a hydrogen atom, halogen, cyano, $C_{1-6}$ alkylsulfonyl, $-SO_2-NR^5R^6$, $-NR^7R^8$, $-NR^9-C(=O)R^{10}$, $-NR^{11}-SO_2-R^{12}$, $-C(=O)NR^{13}R^{14}$, $-C(=O)OR^{15}$, optionally substituted $C_{1-6}$ alkyl, or optionally substituted $C_{1-6}$ alkoxy, and
$R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and a 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, $C_{1-6}$ alkyl, and $C_{1-6}$ alkoxy).

Item 40

A method for treating or preventing a disorder or disease associated with an abnormal nerve excitation, comprising administering, to a patient in need thereof, a therapeutically or prophylactically effective amount of a compound represented by

[Chemical Formula 22]

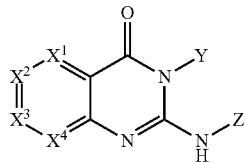

(1)

or a pharmaceutically acceptable salt thereof
wherein
$X^1$ represents $CR^1$ or N,
$X^2$ represents $CR^2$ or N,
$X^3$ represents $CR^3$ or N,
$X^4$ represents $CR^4$ or N,
wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
Z represents optionally substituted 5- to 10-membered heteroaryl,
$R^1$, $R^2$, $R^3$, and $R^4$ each independently represent a hydrogen atom, halogen, cyano, $C_{1-6}$ alkylsulfonyl, $-SO_2-NR^5R^6$, $-NR^7R^8$, $-NR^9-C(=O)R^{10}$, $-NR^{11}SO_2-R^{12}$, $-C(=O)NR^{13}R^{14}$, $-C(=O)OR^{15}$, optionally substituted $C_{1-6}$ alkyl, or optionally substituted $C_{1-6}$ alkoxy, and
$R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and a 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, $C_{1-6}$ alkyl, and alkoxy).

Item 41

Use of a compound represented by

[Chemical Formula 23]

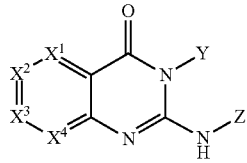

(1)

or a pharmaceutically acceptable salt thereof
wherein
  $X^1$ represents $CR^1$ or N,
  $X^2$ represents $CR^2$ or N,
  $X^3$ represents $CR^3$ or N,
  $X^4$ represents $CR^4$ or N,
    wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
  Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
  Z represents optionally substituted 5- to 10-membered heteroaryl,
  $R^1$, $R^2$, $R^3$, and $R^4$ each independently represent a hydrogen atom, halogen, cyano, $C_{1-6}$ alkylsulfonyl, —$SO_2$—$NR^5R^6$, —$NR^7R^8$, —$NR^9$—C(=O)$R^{10}$, —$NR^{11}$—$SO_2$—$R^{12}$, —C(=O)$NR^{13}R^{14}$, —C(=O)$OR^{15}$, optionally substituted $C_{1-6}$ alkyl, or optionally substituted $C_{1-6}$ alkoxy, and
  $R^5$, $R^6$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, $C_{1-6}$ alkyl, and $C_{1-6}$ alkoxy), for the manufacture of a therapeutic medicament or prophylactic medicament for a disorder or disease associated with an abnormal nerve excitation.

Item 42

A compound represented by

[Chemical Formula 24]

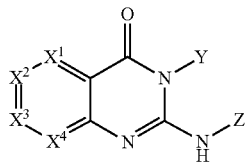

(1)

or a pharmaceutically acceptable salt thereof
wherein
  $X^1$ represents $CR^1$ or N,
  $X^2$ represents $CR^2$ or N,
  $X^3$ represents $CR^3$ or N,
  $X^4$ represents $CR^4$ or N,
    wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
  Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
  Z represents optionally substituted 5- to 10-membered heteroaryl,
  $R^1$, $R^2$, $R^3$, and $R^4$ each independently represent a hydrogen atom, halogen, cyano, $C_{1-6}$ alkylsulfonyl, —$SO_2$—$NR^5R^6$, —$NR^7R^8$, —$NR^9$—C(=O)$R^{10}$, —$NR^{11}$—$SO_2$—$R^{12}$, —C(=O)$NR^{13}R^{14}$, —C(=O)$OR^{15}$, optionally substituted $C_{1-6}$ alkyl, or optionally substituted $C_{1-6}$ alkoxy, and
  $R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, $C_{1-}$ alkyl, and $C_{1-6}$ alkoxy), for use in the treatment or prophylaxis of a disorder or disease associated with an abnormal nerve excitation.

Item 43

A medicament comprised of a compound represented by

[Chemical Formula 25]

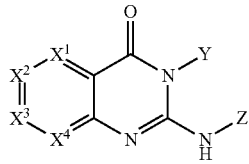
(1)

or a pharmaceutically acceptable salt thereof
wherein
$X^1$ represents $CR^1$ or N,
$X^2$ represents $CR^2$ or N,
$X^3$ represents $CR^3$ or N,
$X^4$ represents $CR^4$ or N,
wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
Z represents optionally substituted 5- to 10-membered heteroaryl,
$R^1$, $R^2$, $R^3$, and $R^4$ each independently represent a hydrogen atom, halogen, cyano, $C_{1-6}$ alkylsulfonyl, $-SO_2-NR^5R^6$, $-NR^7R^8$, $-NR^9-C(=O)R^{10}-NR^{11}-SO_2-R^{12}$, $-C(=O)NR^{13}R^{14}$, $-C(=O)OR^{15}$, optionally substituted $C_{1-6}$ alkyl, or optionally substituted $C_{1-6}$ alkoxy, and
$R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and a 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, alkyl, and $C_{1-6}$ alkoxy), in combination with at least one agent selected from agents classified as an antiepileptic medicament, an antidepressant, an anxiolytic, or an antipsychotic medicament.

Item 44

A pharmaceutical composition comprising a compound represented by

[Chemical Formula 26]

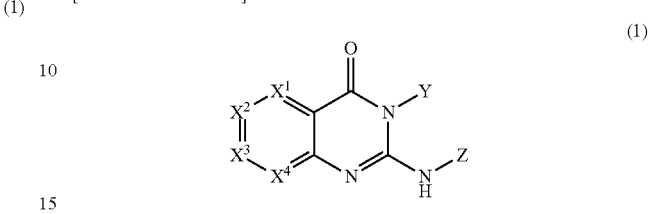
(1)

or a pharmaceutically acceptable salt thereof
wherein
$X^1$ represents $CR^1$ or N,
$X^2$ represents $CR^2$ or N,
$X^3$ represents $CR^3$ or N,
$X^4$ represents $CR^4$ or N,
wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
Y represents optionally substituted $C_{1-6}$ alkyl, optionally substituted $C_{3-10}$ cycloalkyl, an optionally substituted 4- to 10-membered non-aryl heterocyclic group, optionally substituted $C_{6-10}$ aryl, or optionally substituted 5- to 10-membered heteroaryl,
Z represents optionally substituted 5- to 10-membered heteroaryl,
$R^1$, $R^2$, $R^3$, and $R^4$ each independently represent a hydrogen atom, halogen, cyano, $C_{1-6}$ alkylsulfonyl, $-SO_2-NR^5R^6$, $-NR^7R^8$, $-NR^9-C(=O)R^{10}$, $-NR^{11}-SO_2-R^{12}$, $-C(=O)NR^{13}R^{14}$, $-C(=O)OR^{15}$, optionally substituted $C_{1-6}$ alkyl, or optionally substituted $C_{1-6}$ alkoxy, and
$R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-6}$ alicyclic group, $C_{1-6}$ alkoxy, and a 4- to 6-membered non-aryl heterocyclic group), wherein $R^5$ and $R^6$, $R^7$ and $R^8$, and $R^{13}$, and $R^{14}$, together with the nitrogen atom to which they are attached, may form a 4- to 10-membered nitrogen-containing non-aryl heterocycle (wherein the ring is optionally substituted with 1 to 5 of the same or different substituents selected from the group consisting of halogen, hydroxy, $C_{1-6}$ alkyl, and $C_{1-6}$ alkoxy), for the treatment or prophylaxis of a disorder or disease associated with an abnormal nerve excitation by concomitantly using at least one agent selected from agents classified as an antiepileptic medicament, an antidepressant, an anxiolytic, or an antipsychotic medicament.

The present disclosure is intended so that one or more of the features described above can be provided not only as the explicitly disclosed combinations, but also as other combinations thereof. Additional embodiments and advantages of the present disclosure are recognized by those skilled in the art by reading and understanding the following detailed description as needed.

Advantageous Effects of Invention

The compound of the present disclosure has activity to suppress hyperexcitation of the neural circuit understood to be in the background of various epileptic conditions and exhibits a potent antiseizure activity in epilepsy models using human cells and multiple animal seizure models. Thus, the compound is useful as an antiepileptic medicament exhibiting a broad range of therapeutic spectra (therapeutic medicament and/or prophylactic medicament for epileptic seizures (generalized seizures including tonic, clonic, absence, myoclonic, and atonic seizures, focal seizure, epileptic spasms, and unknown seizures), status epilepticus, epilepsy syndromes (Dravet syndrome, Ohtahara syndrome, West syndrome, Lennox-Gastaut syndrome, autosomal dominant nocturnal frontal lobe epilepsy, mesial temporal lobe epilepsy with hippocampal sclerosis, Rasmussen syndrome, etc.), epilepsy attributed to structural/metabolic etiology (cortical dysplasia, neurocutaneous syndrome (tuberous sclerosis complex, Sturge-Weber syndrome, etc.), etc.), etc., developmental disorder, mental disorder, or cognitive disorder manifested as a complication thereof, and the like). The compound is also expected to have an effect of improving the pathological condition for a disorder or disease with a background in the imbalance between excitation signals and inhibition signals in the neural circuit (developmental disorders (autism spectrum disorder, Rett syndrome, Angelman syndrome, fragile X syndrome, attention deficit hyperactivity disorder, etc.), mental disorders (schizophrenia, bipolar disorder, depression, anxiety, obsessive-compulsive disorder, etc.), cognitive disorders (Alzheimer's disease, other dementia, Parkinson's disease, etc.)).

DESCRIPTION OF EMBODIMENTS

Figure 1:
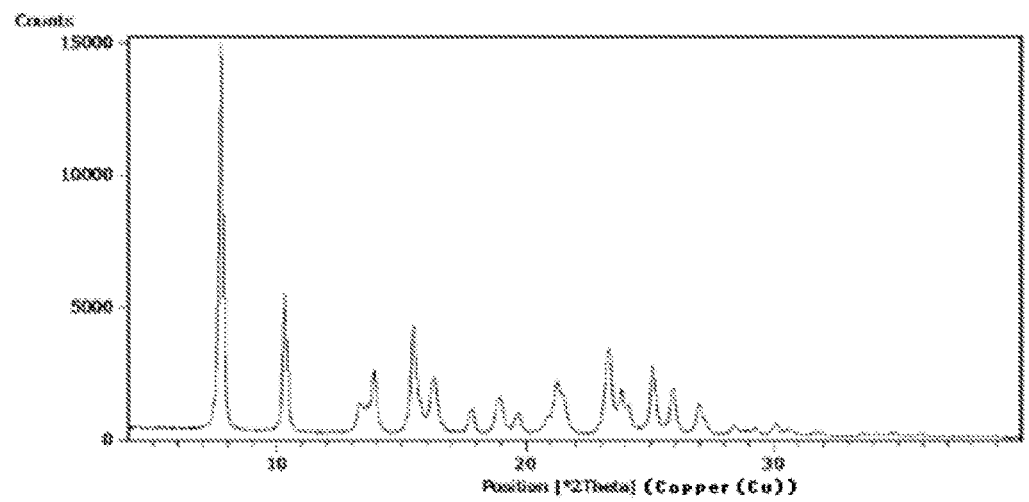
FIG. 1 shows an X-ray powder diffraction pattern of a type I crystal of the compound of Example 3. The horizontal axis indicates the diffraction angle 2θ(°), and the vertical axis indicates the count (the same applies to FIGS. 2 to 5).

The present disclosure is described hereinafter in more detail. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

If the present specification has descriptions with and without "group" with regard to a group such as "phenyl" and "phenyl group", they are interpreted to indicate the same group.

The number of substituents in a group defined as "optionally substituted" or "substituted" is not particularly limited, as long as a substitution is possible. Moreover, unless indicated otherwise, the description for each group is also applicable when the group is a part of, or a substituent of, another group.

A substituent in "optionally substituted" is selected from substituent group α that consists of the following, which is optionally substituted with 1 to 5 of the same or different substituents. While not particularly limited by the type of substituent, if an atom to which the substituent attaches is an oxygen atom, a nitrogen atom, or a sulfur atom, the substituent is limited to the following substituents that attach to a carbon atom.

Substituent Group α Includes
1) a halogen atom
2) a hydroxyl group
3) a carboxyl group
4) a cyano group
5) a $C_{1-6}$ alkyl group
6) a $C_{2-6}$ alkenyl group
7) a $C_{2-6}$ alkynyl group
8) a $C_{1-6}$ alkoxy group
9) a $C_{1-6}$ alkylthio group
10) a $C_{1-6}$ alkylcarbonyl group
11) a $C_{1-6}$ alkylsulfonyl group
(wherein each substituent from 5) to 11) is optionally substituted with 1 to 5 of the same or different substituents selected from substituent group β)
12) a $C_{3-10}$ alicyclic group
13) a $C_{3-10}$ alicyclic oxy group
14) a $C_{6-10}$ aryloxy group
15) a 5- or 6-membered heteroaryloxy group
16) a 4- to 10-membered non-aryl heterocyclyl oxy group
17) a $C_{6-10}$ alicyclic thio group
18) a $C_{6-10}$ arylthio group
19) a 5- or 6-membered heteroarylthio group
20) a 4- to 10-membered non-aryl heterocyclyl thio group
21) $C_{6-10}$ aryl
22) 5- or 6-membered heteroaryl
23) a 4- to 10-membered non-aryl heterocyclic group
24) a $C_{3-10}$ alicyclic carbonyl group
25) a $C_{6-10}$ arylcarbonyl group
26) a 5- or 6-membered heteroarylcarbonyl group
27) a 4- to 10-membered non-aryl heterocyclyl carbonyl group
28) a $C_{3-10}$ alicyclic sulfonyl group
29) a $C_{6-10}$ arylsulfonyl group
30) a 5- or 6-membered heteroarylsulfonyl group
31) a 4- to 10-membered non-aryl heterocyclyl sulfonyl group
(wherein each substituent from 12) to 31) is optionally substituted with 1 to 5 of substituent group β or 1) a $C_{1-6}$ alkyl group) and
32) —$NR^{16}R^{17}$, Substituent Group β is a Group Consisting of
1) a halogen atom,
2) a hydroxyl group,
3) a carboxyl group,
4) a cyano group, 5) a $C_{3-10}$ alicyclic group,
6) a $C_{1-6}$ alkoxy group,
7) a $C_{3-10}$ alicyclic oxy group,
8) a $C_{1-6}$ alkylthio group,
9) a 5- or 6-membered heteroarylthio group,
10) $C_{6-10}$ aryl,
11) 5- or 6-membered heteroaryl,
12) a 4- to 10-membered non-aryl heterocyclic group,
13) a $C_{1-6}$ alkylcarbonyl group,
14) a $C_{3-10}$ alicyclic carbonyl group,
15) a $C_{6-10}$ arylcarbonyl group,
16) a 5- or 6-membered heteroarylcarbonyl group,
17) a 4- to 10-membered non-aryl heterocyclyl carbonyl group, and
18) —$NR^{18}R^{19}$,
(wherein each substituent from 5) to 17) in substituent group is optionally substituted with 1 to 5 substituents selected from the group consisting of a halogen atom, a hydroxyl group, a cyano group, a carboxyl group, and —$NR^{20}R^{21}$),
$R^{16}$, $R^{17}$, $R^{18}$, and $R^{19}$ are the same or different, each independently a hydrogen atom or a $C_{1-6}$ alkyl group (wherein the alkyl group is optionally substituted with 1 to 3 of the same or different substituents selected from a hydroxyl group, a cyano group, a $C_{1-6}$ alkoxy group, and —$NR^{20}R^{21}$), and
$R^{20}$ and $R^{21}$ are the same or different, each independently a hydrogen atom or a $C_{1-6}$ alkyl group.

Preferred examples of substituents in "optionally substituted" include the following substituents.

Preferred substituent group α includes
1) a halogen atom
2) a hydroxyl group
3) a carboxyl group
4) a cyano group
5) a $C_{1-6}$ alkyl group
6) a $C_{1-6}$ alkoxy group
7) a $C_{1-6}$ alkylthio group
8) a $C_{1-6}$ alkylcarbonyl group
(wherein each substituent from 5) to 8) is optionally substituted with 1 to 5 of the same or different substituents selected from substituent group β)
9) a $C_{3-10}$ alicyclic group
10) a $C_{3-10}$ alicyclic oxy group
11) a $C_{6-10}$ aryloxy group
12) a 5- or 6-membered heteroaryloxy group
13) a 4- to 10-membered non-aryl heterocyclyl oxy group
14) a $C_{3-10}$ alicyclic thio group
15) a $C_{6-10}$ arylthio group
16) a 5- or 6-membered heteroarylthio group
17) a 4- to 10-membered non-aryl heterocyclyl thio group
18) $C_{6-10}$ aryl
19) 5- or 6-membered heteroaryl
20) a 4- to 10-membered non-aryl heterocyclic group
21) a $C_{3-10}$ alicyclic carbonyl group
22) a $C_{6-10}$ arylcarbonyl group
23) a 5- or 6-membered heteroarylcarbonyl group
24) a 4- to 10-membered non-aryl heterocyclyl carbonyl group
(wherein each substituent from 9) to 24) is optionally substituted with 1 to 5 of substituent group β or 1) a $C_{1-6}$ alkyl group) and
25) —$NR^{18}R^{17}$, Preferred substituent group β is a group consisting of
1) a halogen atom
2) a hydroxyl group
3) a cyano group
4) a $C_{3-10}$ alicyclic group
5) a $C_{1-6}$ alkoxy group
6) a $C_{1-6}$ alkylthio group
7) a 5- or 6-membered heteroarylthio group
8) 5- or 6-membered heteroaryl
9) a 4- to 10-membered non-aryl heterocyclic group
10) a $C_{1-6}$ alkylcarbonyl group
11) a $C_{3-10}$ alicyclic carbonyl group
12) a $C_{6-10}$ arylcarbonyl group
13) a 5- or 6-membered heteroarylcarbonyl group
14) a 4- to 10-membered non-aryl heterocyclyl carbonyl group and
15) —$NR^{18}R^{19}$
(wherein each substituent from 4) to 14) in substituent group is optionally substituted with 1 to 5 substituents selected from the group consisting of a halogen atom, a hydroxyl group, a cyano group, a carboxyl group, and —$NR^{20}R^{21}$,
$R^{16}$, $R^{17}$, $R^{18}$, and $R^{19}$ are the same or different, each independently a hydrogen atom or a $C_{1-6}$ alkyl group (wherein the alkyl group is optionally substituted with 1 to 3 of the same or different substituents selected from a hydroxyl group, a cyano group, a $C_{1-6}$ alkoxy group, and —$NR^{20}R^{21}$), and
$R^{20}$ and $R^{21}$ are the same or different, each independently a hydrogen atom or a $C_{1-6}$ alkyl group.

More preferred examples of substituents in "optionally substituted" include the following substituents.

More preferred substituent group α includes
1) a halogen atom
2) a hydroxyl group
3) a cyano group
4) a $C_{1-6}$ alkyl group
5) a $C_{1-6}$ alkoxy group
6) a $C_{1-6}$ alkylthio group
7) a $C_{1-6}$ alkylcarbonyl group
(wherein each substituent from 4) to 7) is optionally substituted with 1 to 5 of the same or different substituents selected from substituent group β)
8) a 5- or 6-membered heteroaryloxy group
9) a 4- to 10-membered non-aryl heterocyclyl oxy group
10) a 5- or 6-membered heteroarylthio group
11) a 4- to 10-membered non-aryl heterocyclyl thio group
12) $C_{6-10}$ aryl
13) 5- or 6-membered heteroaryl
14) a 4- to 10-membered non-aryl heterocyclic group
(wherein each substituent from 4) to 14) is optionally substituted with 1 to 5 of substituent group β or 1) a $C_{1-6}$ alkyl group) and
15) —$NR^{16}R^{17}$, Substituent group β is more preferably
1) a halogen atom,
2) a hydroxyl group,
3) a cyano group, and
4) —$NR^{18}R^{19}$,
$R^{16}$, $R^{17}$, $R^{18}$, and $R^{19}$ are the same or different, each independently a hydrogen atom or a $C_{1-6}$ alkyl group (wherein the alkyl group is optionally substituted with 1 to 3 of the same or different substituents selected from a hydroxyl group, a cyano group, a $C_{1-6}$ alkoxy group, and —$NR^{20}R^{21}$), and
$R^{20}$ and $R^{21}$ are the same or different, each independently a hydrogen atom or a $C_{1-6}$ alkyl group.

"$C_{1-6}$" means that the number of carbon atoms is 1 to 6. The same applies to other numbers. For example, "$C_{1-4}$" means that the number of carbon atoms is 1 to 4.

"Heteroatom" refers to an oxygen atom, a nitrogen atom, a sulfur atom, or the like.

"Halogen atom" refers to any atom other than a carbon atom and a hydrogen atom, meaning a fluorine atom, chlorine atom, bromine atom, or iodine atom, and is preferably a fluorine atom or chlorine atom. A "halogen atom" is also referred to as "halogen".

"$C_{1-6}$ alkyl" or "$C_{1-6}$ alkyl group" refers to a linear or branched saturated hydrocarbon group with 1 to 6 carbon atoms. A $C_{1-6}$ alkyl group is preferably a "$C_{1-4}$ alkyl group", and more preferably a "$C_{1-3}$ alkyl group" or "$C_{2-3}$ alkyl group". Specific examples of "$C_{1-3}$ alkyl group" include methyl, ethyl, propyl, 1-methylethyl, and the like. Specific examples of "$C_{2-3}$ alkyl group" include ethyl, propyl, 1-methylethyl, and the like. Specific examples of "$C_{1-4}$ alkyl group" include, in addition to the specific examples specified for the "$C_{1-3}$ alkyl group" described above, butyl, 1,1-dimethylethyl, 1-methylpropyl, 2-methylpropyl, and the like. Specific examples of "$C_{1-6}$ alkyl group" include, in addition to the specific examples specified for the "$C_{1-4}$ alkyl group" described above, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like.

"$C_{2-6}$ alkenyl" or "$C_{2-6}$ alkenyl group" refers to a linear or branched unsaturated hydrocarbon group with 2 to 6 carbon atoms, comprising one or more carbon-carbon double bonds. "$C_{2-6}$ alkenyl group" is preferably a "$C_{2-4}$ alkenyl group". Specific examples of "$C_{2-6}$ alkenyl group" include, but are not limited to, a vinyl group, 1-propylenyl group, 2-propylenyl group, 1-butenyl group, 2-butenyl group, 3-butenyl group, 2-methyl-1-propylenyl group, 2-methyl-2-propylenyl group, and the like.

"$C_{2-6}$ alkynyl" or "$C_{2-6}$ alkynyl group" refers to a linear or branched unsaturated aliphatic hydrocarbon group comprising one or more triple bonds. "$C_{2-6}$ alkynyl group" is preferably a "$C_{2-4}$ alkynyl group". Specific examples thereof include, but are not limited to, an ethynyl group, 1-propynyl group, 2-propynyl group, 1-butynyl group, 1-methyl-2-propynyl group, 3-butynyl group, 1-pentynyl group, 1-hexynyl group, and the like.

"$C_{3-10}$ alicyclic group" refers to a monocyclic or bicyclic monovalent non-aromatic hydrocarbon ring group with 3 to 10 carbon atoms, including those with a partially unsaturated bond, those with a partially crosslinked structure, those that have a partially spiro form, and those having one or more carbonyl structures. "Alicyclic group" encompasses cycloalkyl groups, cycloalkenyl groups, and cycloalkynyl groups. "$C_{3-10}$ alicyclic group" is preferably a "$C_{3-6}$ alicyclic group", and more preferably a "$C_{5-6}$ alicyclic group". Specific examples of "$C_{5-6}$ alicyclic group" include cyclopentyl, cyclohexyl, and the like. Specific examples of "$C_{3-6}$ alicyclic group" include, in addition to the specific examples specified for the "$C_{5-6}$ alicyclic group" described above, cyclopropyl, cyclobutyl, and the like. Specific examples of "$C_{3-10}$ alicyclic group" include, in addition to the specific examples specified for the "$C_{3-6}$ alicyclic group" described above, cycloheptyl, cyclooctyl, cyclononyl, cyclodecyl, adamantyl, and the like.

Specific examples of "$C_{3-10}$ alicyclic group" with a partially crosslinked structure include, but are not limited to, those with a structure shown below and the like.

[Chemical Formula 27]

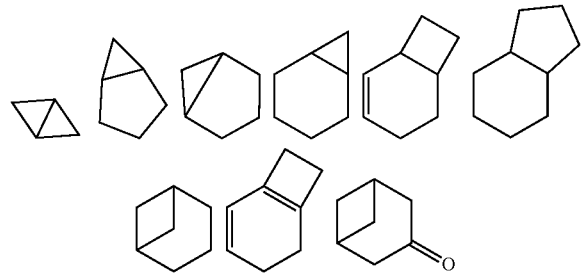

"$C_{3-10}$ alicyclic group" also encompasses compounds fused to an aromatic ring. Specific examples thereof include the groups represented by the following and the like.

[Chemical Formula 28]

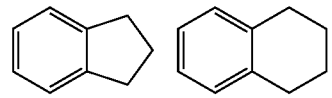

"$C_{6-10}$ aryl" refers to a monocyclic or bicyclic aromatic hydrocarbon group with 6 to 10 carbon atoms. "$C_{6-10}$ aryl" may be fused to the "alicyclic group" or "non-aryl heterocycle" described above at any possible position. Specific examples of "$C_{6-10}$ aryl" include phenyl, 1-naphthyl, 2-naphthyl, and the like. Preferred examples of "$C_{6-10}$ aryl" include phenyl. Specific examples of the fused ring structure include the groups represented by the following and the like.

[Chemical Formula 29]

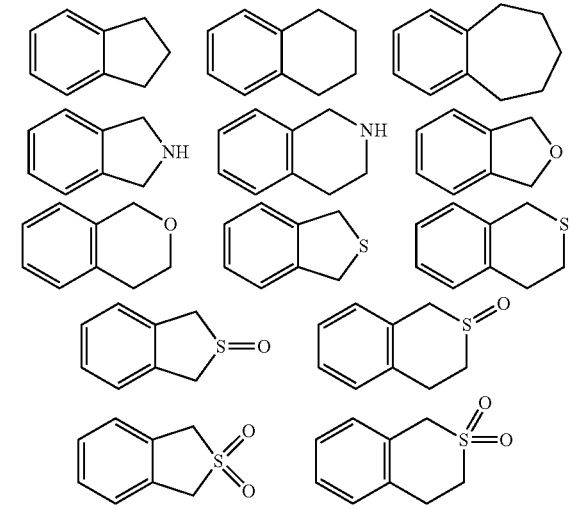

[Chemical Formula 30]

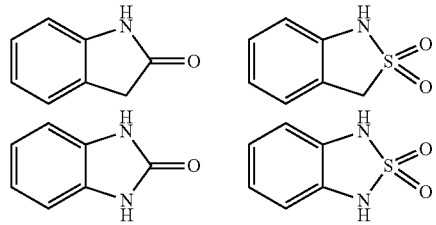

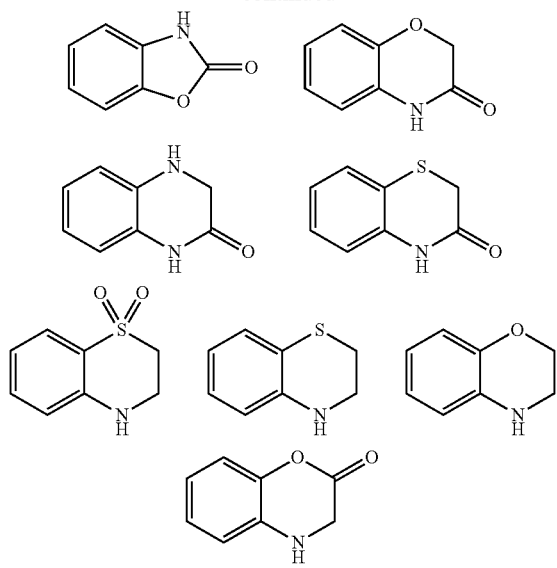

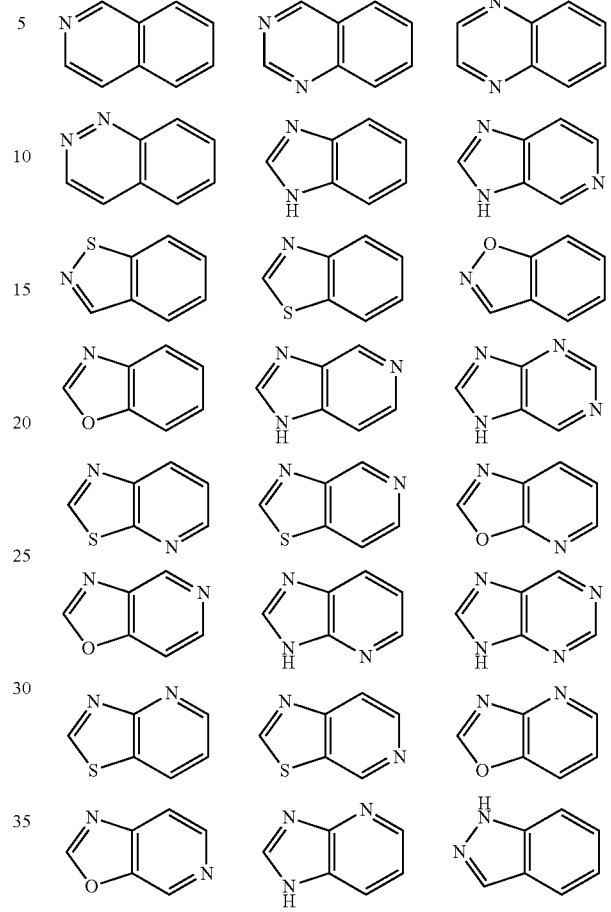

[Chemical Formula 31]

"5- to 10-membered heteroaryl" refers to a monocyclic or bicyclic aromatic heterocyclic group comprised of 5 to 10 atoms, comprising 1 to 4 atoms independently selected from the group consisting of a nitrogen atom, an oxygen atom, and a sulfur atom. "5- to 10-membered heteroaryl" may be fused to the "alicyclic group" or "non-aryl heterocycle" described above at any possible position. "5- to 10-membered heteroaryl" is preferably "5-membered heteroaryl", "6-membered heteroaryl", "5- or 6-membered heteroaryl", "6- to 10-membered heteroaryl", or "9- or 10-membered heteroaryl". Specific examples of "5-membered heteroaryl" include furyl, thienyl, pyrrolyl, pyrazolyl, oxazolyl, thiazolyl, imidazolyl, isoxazolyl, isothiazolyl, and thiadiazolyl. Specific examples of "6-membered heteroaryl" include pyridyl, pyrazinyl, pyrimidinyl, and pyridazinyl. Specific examples of "5- or 6-membered heteroaryl" include furyl, thienyl, pyrrolyl, pyrazolyl, oxazolyl, thiazolyl, imidazolyl, isoxazolyl, isothiazolyl, thiadiazolyl, pyridyl, pyrazinyl, pyrimidinyl, and pyridazinyl. Specific examples of "6- to 10-membered heteroaryl" include pyridyl, pyrazinyl, pyrimidinyl, pyridazinyl, quinoxalyl, triazolopyridyl, and the like. Specific examples of "5- to 10-membered heteroaryl" include the specific examples for the "6- to 10-membered heteroaryl" and "5- or 6-membered heteroaryl" described above.

If Y is "5- to 10-membered heteroaryl", "5- or 6-membered heteroaryl", or "6-membered heteroaryl" in formula 1, Y attaches to a nitrogen atom through a carbon atom on a ring of the heteroaryl group.

"5- to 10-membered heteroaryl" or a Z group which is "5- to 10-membered heteroaryl" in formula 1, such as "pyridyl", "pyrimidinyl", "indazolyl", or "imidazopyridyl", attaches to a nitrogen atom through a carbon atom on a ring of the Z group. In one embodiment, 5- to 10-membered heteroaryl, such as 5- to 10-membered heteroaryl of Z, does not attach to a nitrogen atom to which the heteroaryl attaches at a nitrogen atom on a ring of the heteroaryl group.

Specific examples of "9- or 10-membered heteroaryl" include, but are not limited to, compounds with a structure shown below and the like.

[Chemical Formula 32]

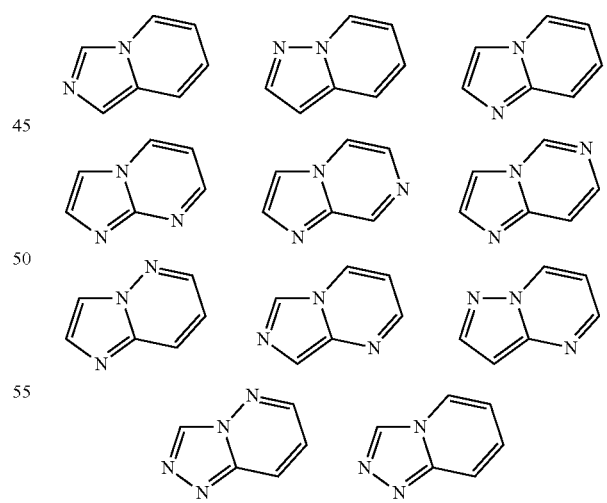

The "5- or 6-membered heteroaryl" or "5- to 10-membered heteroaryl" may form a fused ring structure with a $C_{5-10}$ alicyclic group, or a fused ring structure with a 5- to 10-membered non-aryl heterocycle. Specific examples thereof include the groups represented by the following and the like.

[Chemical Formula 33]

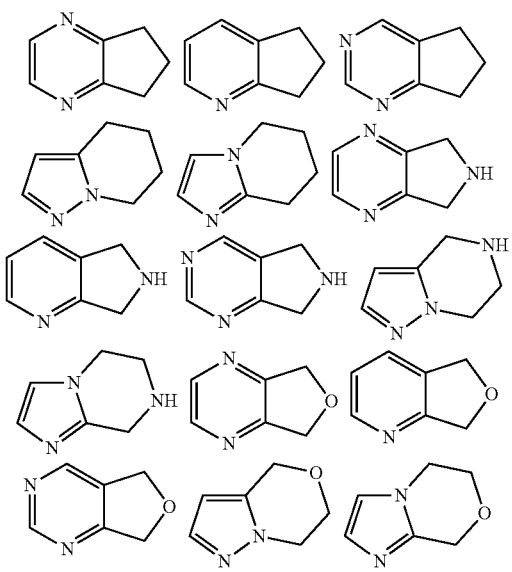

[Chemical Formula 34]

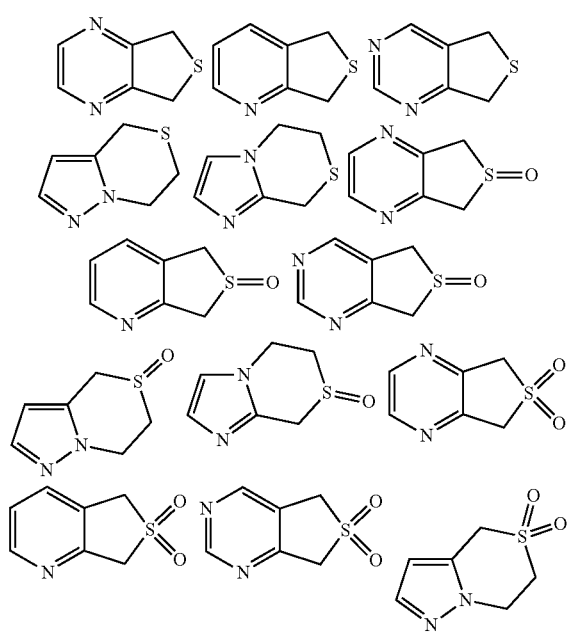

[Chemical Formula 35]

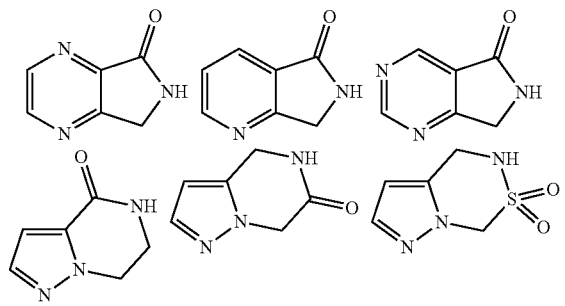

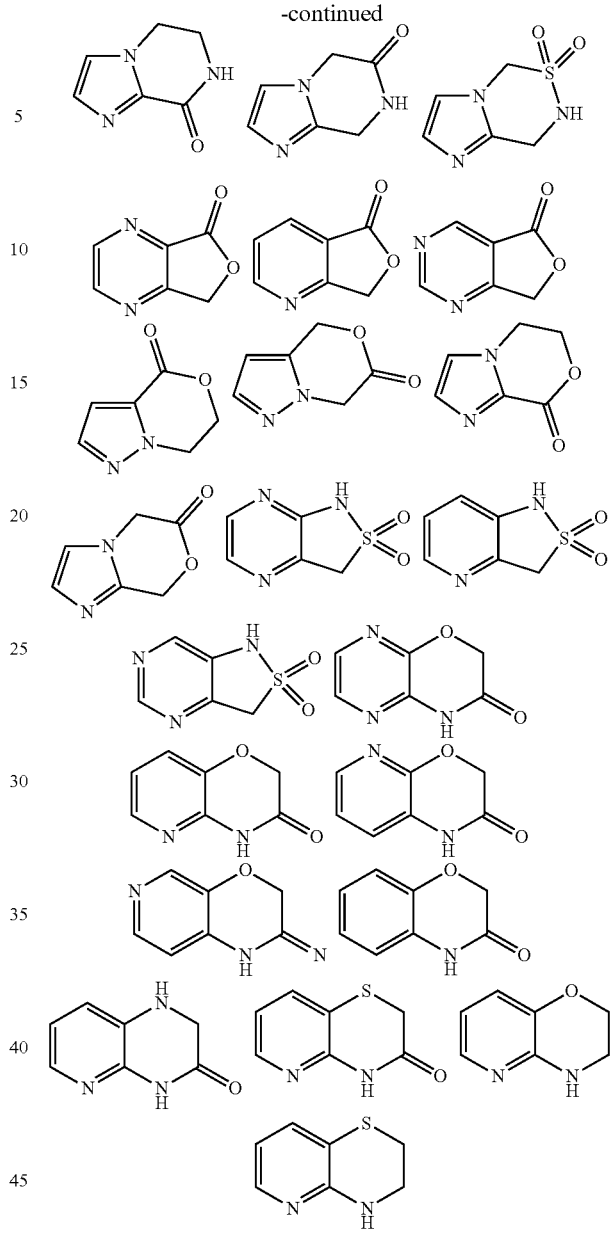

"4- to 10-membered non-aryl heterocyclic group" refers to a monocyclic or bicyclic non-aromatic heterocycle comprised of 4 to 10 atoms, comprising 1 to 2 of the same or different heteroatoms independently selected from the group consisting of a nitrogen atom, an oxygen atom, and a sulfur atom in addition to carbon atoms, including those with a partially unsaturated bond, those with a partially crosslinked structure, and/or those that have a partially spiro form. "4- to 10-membered non-aryl heterocyclic group" is preferably a "4- to 6-membered non-aryl heterocyclic group" or a "4- to 10-membered nitrogen-containing non-aryl heterocyclic group". Specific examples of "4- to 6-membered non-aryl heterocyclic group" include azetidinyl, pyrrolidinyl, piperidyl, piperazinyl, morpholinyl, oxetanyl, tetrahydrofuranyl, tetrahydropyranyl, and the like. In particular, azetidinyl, pyrrolidinyl, piperidyl, morpholinyl, and oxetanyl are preferable. A non-aryl heterocycle may form a fused ring with aryl or heteroaryl. Non-aryl heterocycles also encompass those that are fused with, for example, $C_{6-10}$ aryl or 5- or 6-membered heteroaryl. Further, the non-aryl heterocycle may be comprised by including one or more carbonyl, thiocarbonyl, sulfinyl, or sulfonyl. The non-aryl heterocycles also encompass, for example, lactam, thiolactam, lactone, thiolactone, cyclic imide, cyclic carbamate, cyclic thiocarbamate, and other cyclic groups. In this regard, oxygen atoms of carbonyl, sulfinyl, and sulfonyl and sulfur atoms of thiocarbonyl are not included in the number of 4 to 10 members (size of ring) or in the number of heteroatoms constituting a ring. "4- to 10-membered non-aryl heterocycle" is preferably a "4- to 6-membered non-aryl heterocycle". Specific examples of "4- to 6-membered non-aryl heterocycle" include azetidine, pyrrolidine, piperidine, piperazine, morpholine, homopiperidine, oxetane, tetrahydrofuran, tetrahydropyran, and the like. Specific examples of "4- to 10-membered non-aryl heterocycle" include, in addition to the specific examples specified for the "4- to 6-membered non-aryl heterocycle" described above, compounds with a structure shown below and the like.

[Chemical Formula 36]

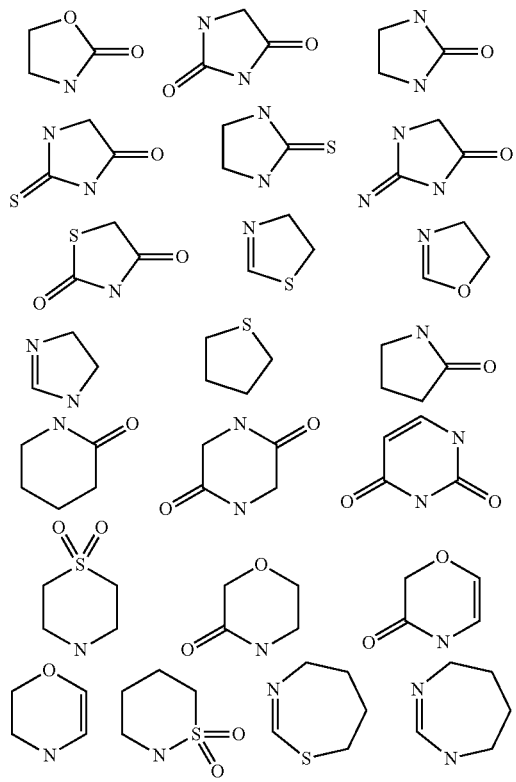

Specific examples of "4- to 10-membered non-aryl heterocycle" with partial crosslinking and/or spiro structure include, but are not limited to, those with a structure shown below and the like.

[Chemical Formula 37]

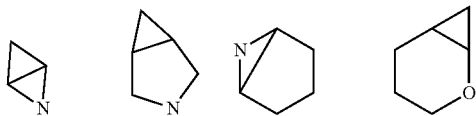

-continued

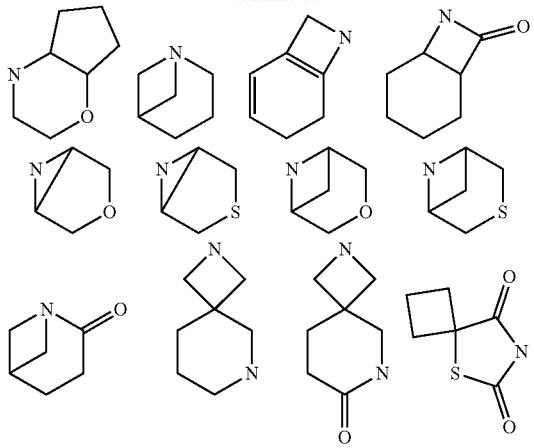

"Oxetanyl" is a saturated 4-membered ring that is a monovalent group comprising one oxygen. Examples thereof include phenyloxetanyl

[Chemical Formula 38]

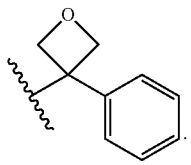

"4- to 10-membered nitrogen-containing non-aryl heterocycle" refers to a monocyclic or bicyclic non-aromatic heterocycle comprised of 4 to 10 atoms, comprising or more of the same or different heteroatoms selected from the group consisting of an oxygen atom, a nitrogen atom, and a sulfur atom, in addition to 1 nitrogen atom, including those with a partially unsaturated bond, those with a partially crosslinked structure, and/or those that have a partially Spiro form. Examples of "4- to 10-membered nitrogen-containing non-aryl heterocycle" is preferably a "4- to 6-membered nitrogen-containing non-aryl heterocycle" or a "5- or 6-membered nitrogen-containing non-aryl heterocycle". Specific examples of "5- or 6-membered nitrogen-containing non-aryl heterocycle" include pyrrolidine, piperidine, piperazine, morpholine, and the like. Specific examples of "4- to 6-membered nitrogen-containing non-aryl heterocycle" include azetidine and the like, in addition to the specific examples specified for the "5- or 6-membered nitrogen-containing non-aryl heterocycle" described above. Specific examples of "4- to 10-membered nitrogen-containing non-aryl heterocycle" include azetidine, azepane, azocane, and the like, in addition to the specific examples specified for the "5- or 6-membered nitrogen-containing non-aryl heterocycle" described above.

Specific examples of "4- to 10-membered nitrogen-containing non-aryl heterocycle" having a partial crosslinking and/or Spiro structure include, but are not limited to, those with a structure shown below and the like.

[Chemical Formula 39]

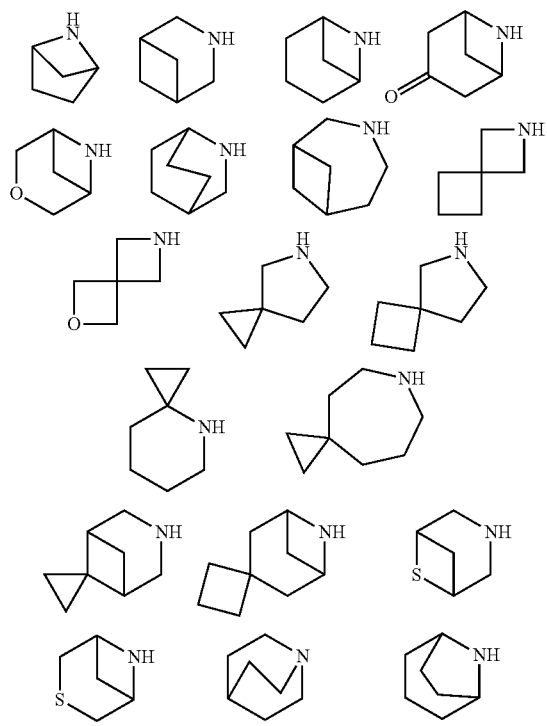

If Y is a "4- to 10-membered nitrogen-containing non-aryl heterocyclic group" or a "5- or 6-membered nitrogen-containing non-aryl heterocyclic group" in formula 1, Y attaches to a nitrogen atom through a carbon atom on a ring of the nitrogen-containing non-aryl heterocyclic group.

Specific examples of "4-membered non-aryl heterocycle" with a partially unsaturated bond include, but are not limited to, those with a structure shown below and the like.

[Chemical Formula 40]

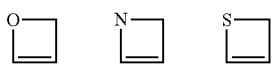

Specific examples of "5-membered non-aryl heterocycle" with a partially unsaturated bond include, but are not limited to, those with a structure shown below and the like.

[Chemical Formula 41]

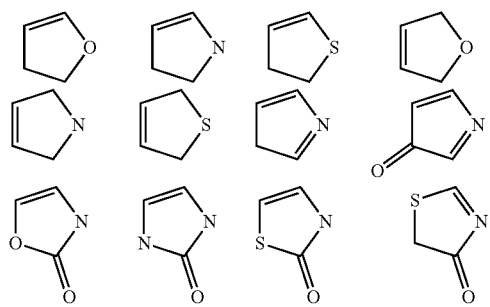

-continued

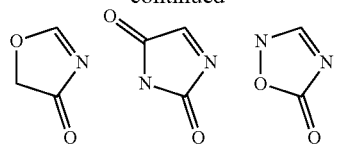

Specific examples of "5-membered non-aryl heterocycle" with a partially crosslinked structure include, but are not limited to, those with a structure shown below and the like.

[Chemical Formula 42]

Specific examples of "5-membered non-aryl heterocycle" comprising carbonyl, thiocarbonyl, or the like include, but are not limited to, those with a structure shown below and the like.

[Chemical Formula 43]

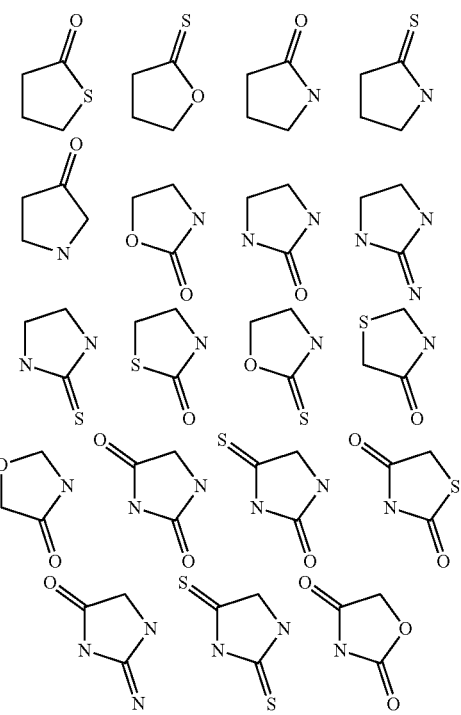

Specific examples of "6-membered non-aryl heterocycle" with a partially unsaturated bond include, but are not limited to, those with a structure shown below and the like.

[Chemical Formula 44]

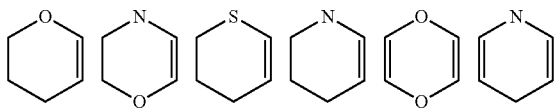

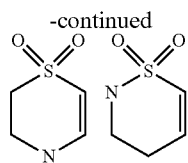

Specific examples of "6-membered non-aryl heterocycle" with a partially crosslinked structure include, but are not limited to, those with a structure shown below and the like.

[Chemical Formula 45]

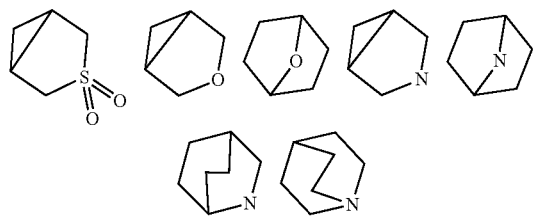

"$C_{1-6}$ alkoxy" or "$C_{1-6}$ alkoxy group" refers to "$C_{1-6}$ alkyloxy", and the "$C_{1-6}$ alkyl" moiety is defined the same as the "$C_{1-6}$ alkyl" described above. "$C_{1-6}$ alkoxy" is preferably "$C_{1-4}$ alkoxy" or "$C_{2-6}$ alkoxy", and more preferably "$C_{1-3}$ alkoxy". Specific examples of "$C_{1-3}$ alkoxy" include methoxy, ethoxy, propoxy, 1-methylethoxy, and the like. Specific examples of "$C_{1-4}$ alkoxy" include, in addition to the specific examples specified for the "$C_{1-3}$ alkoxy" described above, butoxy, 1,1-dimethylethoxy, 1-methylpropoxy, 2-methylpropoxy, and the like. Specific examples of "$C_{2-6}$ alkoxy" include ethoxy, propoxy, 1-methylethoxy, butoxy, 1,1-dimethylethoxy, 1-methylpropoxy, 2-methylpropoxy, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like. Specific examples of "$C_{1-6}$ alkoxy" include, in addition to the specific examples specified for the "$C_{1-4}$ alkoxy" described above, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like.

"$C_{3-6}$ alicyclic oxy" or "$C_{3-6}$ alicyclic oxy group" refers to a ($C_{3-6}$ alicyclic group)-O-group, and the $C_{3-6}$ alicyclic moiety is defined the same as a $C_{3-6}$ alicyclic group. "$C_{3-6}$ alicyclic oxy group" includes "$C_{3-6}$ cycloalkoxy group". "Cycloalkoxy group" refers to "cycloalkyloxy", and the "cycloalkyl" moiety is defined the same as the "cycloalkyl" described above. Specific examples of "$C_{3-6}$ alicyclic oxy group" include a cyclopropoxy group, cyclobutoxy group, cyclopentoxy group, cyclohexoxy group, and the like.

The $C_{6-10}$ aryl moiety of "$C_{6-10}$ aryloxy group" is defined the same as the $C_{6-10}$ aryl described above. "$C_{6-10}$ aryloxy group" is preferably a "$C_6$ or $C_{10}$ aryloxy group". Specific examples of "$C_{6-10}$ aryloxy group" include, but are not limited to, a phenoxy group, 1-naphthyloxy group, 2-naphthyloxy group, and the like.

The 5- or 6-membered heteroaryl moiety of "5- or 6-membered heteroaryloxy group" is defined the same as the "5-membered heteroaryl" or "6-membered heteroaryl" described above. Specific examples of "5- or 6-membered heteroaryloxy group" include, but are not limited to, a pyrazoyloxy group, triazoyloxy group, thiazoyloxy group, thiadiazoyloxy group, pyridyloxy group, pyridazoyloxy group, and the like.

The 4- to 10-membered non-aryl heterocycle moiety of "4- to 10-membered non-aryl heterocyclyl oxy group" is defined the same as the "4- to 10-membered non-aryl heterocycle" described above. "4- to 10-membered non-aryl heterocyclyl oxy group" is preferably a "4- to 6-membered non-aryl heterocyclyl oxy group". Specific examples of "4- to 10-membered non-aryl heterocyclyl oxy group" include, but are not limited to, a tetrahydrofuranyloxy group, tetrahydropyranyloxy group, azetidinyloxy group, pyrrolidinyloxy group, piperidinyloxy group, and the like.

The $C_{1-6}$ alkyl moiety of "$C_{1-6}$ alkylthio group" is defined the same as the $C_{1-6}$ alkyl described above. "$C_{1-6}$ alkylthio group" is preferably a "$C_{1-4}$ alkylthio group", and more preferably a "$C_{1-3}$ alkylthio group". Specific examples of "$C_{1-6}$ alkylthio group" include, but are not limited to, a methylthio group, ethylthio group, propylthio group, butylthio group, isopropylthio group, isobutylthio group, tert-butylthio group, sec-butylthio group, isopentylthio group, neopentylthio group, tert-pentylthio group, 1,2-dimethylpropylthio group, and the like.

"$C_{3-10}$ alicyclic thio" or "$C_{3-10}$ alicyclic thio group" refers to a ($C_{3-10}$ alicyclic group)-S-group, and the $C_{3-10}$ alicyclic moiety is defined the same as the $C_{3-10}$ alicyclic group described above. "$C_{3-10}$ alicyclic thio group" is preferably a "$C_{3-6}$ alicyclic thio group". Specific examples of "$C_{3-6}$ alicyclic thio group" include, but are not limited to, a cyclopropylthio group, cyclobutylthio group, cyclopentylthio group, cyclohexylthio group, and the like.

The $C_{6-10}$ aryl moiety of "$C_{6-10}$ arylthio" or "$C_{6-10}$ arylthio group" is defined the same as the $C_{6-10}$ aryl described above. "$C_{6-10}$ arylthio group" is preferably a "$C_6$ or $C_{10}$ arylthio group". Specific examples of "$C_{6-10}$ arylthio group" include, but are not limited to, a phenylthio group, 1-naphthylthio group, 2-naphthylthio group, and the like.

The 5- or 6-membered heteroaryl moiety of "5- or 6-membered heteroarylthio" or "5- or 6-membered heteroarylthio group" is defined the same as the "5-membered heteroaryl" or "6-membered heteroaryl" described above. Specific examples of "5- or 6-membered heteroarylthio group" include, but are not limited to, a pyrazoylthio group, triazoylthio group, thiazoylthio group, thiadiazoylthio group, pyridylthio group, pyridazoylthio group, and the like.

The 4- to 10-membered non-aryl heterocycle moiety of "4- to 10-membered non-aryl heterocyclyl thio" or "4- to 10-membered non-aryl heterocyclyl thio group" is defined the same as the "4- to 10-membered non-aryl heterocycle" described above. "4- to 10-membered non-aryl heterocyclyl thio group" is preferably a "4- to 6-membered non-aryl heterocyclyl thio group". Specific examples of "4- to 10-membered non-aryl heterocyclyl thio group" include, but are not limited to, a tetrahydropyranylthio group, piperidinylthio group, and the like.

"$C_{1-6}$ alkylcarbonyl" or "$C_{1-6}$ alkylcarbonyl group" refers to a carbonyl group substituted with the "$C_{1-6}$ alkyl group" described above. "$C_{1-6}$ alkylcarbonyl group" is preferably a "$C_{1-4}$ alkylcarbonyl group". Specific examples of "$C_{1-6}$ alkylcarbonyl group" include, but are not limited to, an acetyl group, propionyl group, butyryl group, and the like.

"$C_{3-10}$ to alicyclic carbonyl" or "$C_{3-10}$ alicyclic carbonyl group" refers to a carbonyl group substituted with the "$C_{3-10}$ alicyclic group" described above. "$C_{3-10}$ alicyclic carbonyl group" is preferably a "$C_{3-6}$ alicyclic carbonyl group". Specific examples of "$C_{3-10}$ alicyclic carbonyl group"

include, but are not limited to, a cyclopropylcarbonyl group, cyclopentylcarbonyl group, and the like.

"$C_{6-10}$ arylcarbonyl" or "$C_{6-10}$ arylcarbonyl group" refers to a carbonyl group substituted with the "$C_{6-10}$ aryl" described above. "$C_{6-10}$ arylcarbonyl group" is preferably a "$C_6$ or $C_{10}$ arylcarbonyl group". Specific examples of "$C_{6-10}$ arylcarbonyl group" include, but are not limited to, a benzoyl group, 1-naphthylcarbonyl group, 2-naphthylcarbonyl group, and the like.

"5- or 6-membered heteroarylcarbonyl" or "5- or 6-membered heteroarylcarbonyl group" refers to a carbonyl group substituted with the "5- or 6-membered heteroaryl" described above. Specific examples of "5- or 6-membered heteroarylcarbonyl group" include, but are not limited to, a pyrazoylcarbonyl group, triazoylcarbonyl group, thiazoylcarbonyl group, thiadiazoylcarbonyl group, pyridylcarbonyl group, pyridazoylcarbonyl group, and the like.

"4- to 10-membered non-aryl heterocyclyl carbonyl" or "4- to 10-membered non-aryl heterocyclyl carbonyl group" refers to a carbonyl group substituted with the "4- to 10-membered non-aryl heterocycle" described above. "4- to 10-membered non-aryl heterocyclyl carbonyl group" is preferably a "4- to 6-membered non-aryl heterocyclyl carbonyl group". Specific examples of "4- to 10-membered non-aryl heterocyclyl carbonyl group" include, but are not limited to, an azetidinylcarbonyl group, pyrrolidinylcarbonyl group, piperidinylcarbonyl group, morpholinylcarbonyl group, and the like.

"$C_{1-6}$ alkylsulfonyl" or "$C_{1-6}$ alkylsulfonyl group" refers to a sulfonyl group substituted with the "$C_{1-6}$ alkyl group" described above. "$C_{1-6}$ alkylsulfonyl group" is preferably a "$C_{1-4}$ alkylsulfonyl group". Specific examples of "$C_{1-6}$ alkylsulfonyl group" include, but are not limited to, a methylsulfonyl group, propionylsulfonyl group, butyrylsulfonyl group, and the like.

"$C_{3-10}$ alicyclic sulfonyl" or "$C_{3-10}$ alicyclic sulfonyl group" refers to a sulfonyl group substituted with the "$C_{3-10}$ alicyclic group" described above. "$C_{3-10}$ alicyclic sulfonyl group" is preferably a "$C_{3-6}$ alicyclic sulfonyl group". Specific examples of "$C_{3-10}$ alicyclic sulfonyl group" include, but are not limited to, a cyclopropylsulfonyl group, cyclobutylsulfonyl group, cyclopentylsulfonyl group, cyclohexylsulfonyl group, and the like.

"$C_{6-10}$ arylsulfonyl" or "$C_{6-10}$ arylsulfonyl group" refers to a sulfonyl group substituted with the "$C_{6-10}$ aryl" described above. "$C_{6-10}$ arylsulfonyl group" is preferably a "$C_6$ or $C_{10}$ arylsulfonyl group". Specific examples of "$C_{6-10}$ arylsulfonyl group" include, but are not limited to, a phenylsulfonyl group, 1-naphthylsulfonyl group, 2-naphthylsulfonyl group, and the like.

"5- or 6-membered heteroarylsulfonyl" or "5- or 6-membered heteroarylsulfonyl group" refers to a sulfonyl group substituted with the "5- or 6-membered heteroaryl" described above. Specific examples of "5- or 6-membered heteroarylsulfonyl group" include a pyrazoylsulfonyl group, triazoylsulfonyl group, thiazoylsulfonyl group, thiadiazoylsulfonyl group, pyridylsulfonyl group, pyridazoylsulfonyl group, and the like.

Preferred $X^1$, $X^2$, $X^3$, $X^4$, $R^1$, $R^2$, $R^3$, $R^4$, Y, and Z in the compound of the present disclosure represented by formula (1) are the following, but the technical scope of the present disclosure is not limited to the following scope of the compounds.

Preferred embodiments of $X^1$ include $CR^1$.
Preferred embodiments of $X^2$ includes $CR^2$.
Preferred embodiments of $X^3$ includes $CR^3$.
Preferred embodiments of $X^4$ includes $CR^4$.

Preferred embodiments of $R^1$, $R^2$, $R^3$, and $R^4$ include
(1) a hydrogen atom,
(2) fluorine,
(3) cyano,
(4) $C_{1-6}$ alkoxy, and
(5) $C_{1-6}$ alkyl (wherein the alkyl is optionally substituted with 1 to 3 of the same or different substituents selected from the group consisting of halogen, hydroxy, and alkoxy).

More preferred embodiments of $R^1$, $R^2$, $R^3$, and $R^4$ include
(1) a hydrogen atom,
(2) fluorine, and
(3) cyano.

Still more preferred embodiments of $R^1$, $R^3$, and $R^4$ include a hydrogen atom.

Still more preferred embodiments of $R^2$ include fluorine and cyano.

Preferred embodiments of Y include
(1) $C_{1-6}$ alkyl optionally substituted with 1 to 3 of the same or different substituents selected from the group consisting of halogen, hydroxy, amino, dimethylamino, a $C_{3-6}$ alicyclic group, a 4- to 10-membered nitrogen-containing non-aryl heterocyclic group, $C_{1-6}$ alkoxy, $C_{6-10}$ aryl (wherein the alicyclic group, the nitrogen-containing non-aryl heterocycle, the alkoxy, and the aryl group are each independently optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy),
(2) a $C_{3-10}$ alicyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, a 4- to 10-membered nitrogen-containing non-aryl heterocyclic group, $C_{1-6}$ alkoxy, $C_{6-10}$ aryl (wherein the alicyclic group, the nitrogen-containing non-aryl heterocycle, the alkoxy, and the aryl group are each independently optionally substituted with 1 to 3 of the same or different substituents selected from the group consisting of halogen, cyano, a $C_3$ alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy),
(3) a 4- to 10-membered non-aryl heterocyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, and alkoxy,
(4) $C_{6-10}$ aryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy), and
(5) 5- to 10-membered heteroaryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

Preferred embodiments of Y include
(1) alkyl optionally substituted with 1 to 3 of the same or different substituents selected from the group consisting of fluorine, a $C_{3-6}$ alicyclic group, a 5- or 6-membered nitrogen-containing non-aryl heterocyclic group, phenyl (wherein the alicyclic group, the nitrogen-containing non-aryl heterocycle, and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
(2) a $C_{5-6}$ alicyclic group or phenylcyclopropyl wherein the $C_{5-6}$ alicyclic group or phenylcyclopropyl is optionally substituted with 1 to 3 of the same or different substituents selected from the group consisting of fluorine, amino, dimethylamino, $C_{2-3}$ alkyl optionally substituted with 1 to 3 fluorine, a 5- to 6-membered nitrogen-containing non-aryl heterocyclic group, phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
(3) a 4- to 6-membered nitrogen-containing non-aryl heterocyclic group, phenyloxetanyl, or tetrahydropyranyl wherein the 4- to 6-membered nitrogen-containing non-aryl heterocyclic group, phenyloxetanyl, or tetrahydropyranyl is optionally substituted with 1 to 3 of the same or different substituents selected from the group consisting of fluorine, amino, dimethylamino, alkyl optionally substituted with 1 to 3 fluorine, and phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy),
(4) phenyl optionally substituted with 1 to 3 of the same or different substituents selected from the group consisting of halogen, cyano, dimethylamino, alkoxy, and $C_{1-3}$ alkyl optionally substituted with 1 to 3 fluorine, and
(5) 6-membered heteroaryl optionally substituted with 1 to 3 of the same or different substituents selected from the group consisting of halogen, cyano, alkoxy, and $C_{1-3}$ alkyl optionally substituted with 1 to 3 fluorine.

Preferred embodiments of Y include
(1) alkyl optionally substituted with 1 to 3 of the same or different substituents selected from the group consisting of fluorine, a $C_{3-6}$ alicyclic group, a 5- or 6-membered nitrogen-containing non-aryl heterocyclic group, phenyl (wherein the alicyclic group, the nitrogen-containing non-aryl heterocycle, and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
(2) a $C_{3-6}$ alicyclic group optionally substituted with 1 to 3 of the same or different substituents selected from the group consisting of fluorine, amino, dimethylamino, $C_{1-3}$ alkyl optionally substituted with 1 to 3 fluorine, a 5- to 6-membered nitrogen-containing non-aryl heterocyclic group, phenyl (wherein the nitrogen-containing non-aryl heterocyclic group and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
(3) a 5- or 6-membered nitrogen-containing non-aryl heterocyclic group optionally substituted with 1 to 3 of the same or different substituents selected from the group consisting of fluorine, amino, dimethylamino, and alkyl optionally substituted with 1 to 3 fluorine,
(4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and
(5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine.

More preferred embodiments of Y include
(1) $C_{1-3}$ alkyl optionally substituted with 1 to 3 fluorine,
(2) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine,
(3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
(4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and
(5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine.

Still more preferred embodiments of Y include
(1) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine,
(2) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
(3) phenyl optionally substituted with 1 to 3 of the same or different substituents selected from the group consisting of halogen, cyano, methoxy, and $C_{1-3}$ alkyl optionally substituted with 1 to 3 fluorine, and
(4) 5- or 6-membered heteroaryl optionally substituted with 1 to 3 of the same or different substituents selected from the group consisting of halogen, cyano, methoxy, and $C_{1-3}$ alkyl optionally substituted with 1 to 3 fluorine.

Still more preferred embodiments of Y include
(1) phenyl optionally substituted with 1 to 2 of the same or different substituents selected from the group consisting of fluorine, cyano, methoxy, and methyl, and
(2) 5- or 6-membered heteroaryl optionally substituted with 1 to 2 of the same or different substituents selected from the group consisting of fluorine, cyano, methoxy, and methyl.

The most preferred embodiments of Y include
(1) phenyl optionally substituted with 1 to 2 of the same or different substituents selected from the group consisting of fluorine, cyano, methoxy, and methyl, and
(2) 6-membered heteroaryl optionally substituted with 1 to 2 of the same or different substituents selected from the group consisting of fluorine, cyano, methoxy, and methyl.

Preferred embodiments of Z include 6- to 10-membered heteroaryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

Preferred embodiments of Z include 6- to 10-membered heteroaryl optionally substituted with 1 to 3 of the same or different substituents selected from the group consisting of halogen, cyano, $C_{2-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

Preferred embodiments of Z include 6- to 10-membered heteroaryl, thienyl, pyrrolyl, thiazolyl, isothiazolyl, isoxazolyl, and thiadiazolyl wherein the 6- to 10-membered heteroaryl, thienyl, pyrrolyl, thiazolyl, isothiazolyl, isoxazolyl, and thiadiazolyl are optionally substituted with 1 to 3 of the same or different substituents selected from the group consisting of fluorine, cyano, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

More preferred embodiments of Z include 6- to 10-membered heteroaryl optionally substituted with 1 to 3 of the same or different substituents selected from the group consisting of fluorine, chloro, cyano, $C_{1-6}$ alkoxy, and $C_{1-3}$ alkyl optionally substituted with 1 to 3 fluorine.

Still more preferred embodiments of Z include pyridyl, pyrimidinyl, indazolyl, and imidazopyridyl optionally substituted with 1 to 3 of the same or different substituents selected from the group consisting of fluorine, chloro, cyano, methoxy, and $C_{1-3}$ alkyl optionally substituted with 1 to 3 fluorine.

Still more preferred embodiments of Z include pyridyl, pyrimidinyl, indazolyl, and imidazopyridyl optionally substituted with 1 to 3 of the same or different substituents selected from the group consisting of fluorine, chloro, cyano, and $C_{1-3}$ alkyl optionally substituted with 1 to 3 fluorine.

The most preferred embodiments of Z include pyridyl optionally substituted with 1 to 3 of the same or different substituents selected from the group consisting of fluorine, chloro, cyano, and $C_{1-3}$ alkyl optionally substituted with 1 to 3 fluorine.

An embodiment of the compound represented by formula (1) includes the following (A).

(A)

A compound or a pharmaceutically acceptable salt thereof, wherein
$X^1$ is $CR^1$ or N,
$X^2$ is $CR^2$ or N,
$X^3$ is $CR^3$ or N,
$X^4$ is $CR^4$ or N,
wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if is $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
$R^1$, $R^2$, $R^3$, and $R^4$ are each independently
(1) a hydrogen atom,
(2) halogen,
(3) cyano,
(4) $C_{1-6}$ alkoxy, or
(5) $C_{1-6}$ alkyl (wherein the alkyl is optionally substituted with 1 to 3 of the same or different substituents selected from the group consisting of halogen, hydroxy, and $C_{1-6}$ alkoxy),
Y is
(1) $C_{1-6}$ alkyl optionally substituted with 1 to 3 of the same or different substituents selected from the group consisting of halogen, hydroxy, amino, dimethylamino, a $C_{3-6}$ alicyclic group, a 4- to 10-membered nitrogen-containing non-aryl heterocyclic group, $C_{1-6}$ alkoxy, $C_{6-10}$ aryl (wherein the alicyclic group, the nitrogen-containing non-aryl heterocycle, the alkoxy, and the aryl group are each independently optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a alicyclic group, $C_{1-6}$ alkyl optionally substituted with 1 to 5 fluorine, and $C_{1-6}$ alkoxy),
(2) a $C_{3-10}$ alicyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, a 4- to 10-membered nitrogen-containing non-aryl heterocyclic group, $C_{1-6}$ alkoxy, $C_{6-10}$ aryl (wherein the alicyclic group, the nitrogen-containing non-aryl heterocycle, the alkoxy, and the aryl group are each independently optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy), and 5- to 10-membered heteroaryl (wherein the heteroaryl group is optionally substituted with 1 to 3 of the same or different substituents selected from the group consisting of halogen, cyano, a $C_{3-6}$ alicyclic group, $C_{1-6}$ alkyl optionally substituted with 1 to 5 fluorine, and $C_{1-6}$ alkoxy),
- (3) a 4- to 10-membered nitrogen-containing non-aryl heterocyclic group optionally substituted with 1 to 3 of the same or different substituents selected from the group consisting of halogen, hydroxy, amino, dimethylamino, $C_{1-6}$ alkyl optionally substituted with 1 to 5 fluorine, a $C_{3-6}$ alicyclic group, and $C_{1-6}$ alkoxy,
- (4) $C_{6-10}$ aryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy), or
- (5) 5- to 10-membered heteroaryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy), and Z is 6- to 10-membered heteroaryl optionally substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

An embodiment of the compound represented by formula (1) includes the following (B).

(B)

A compound or a pharmaceutically acceptable salt thereof, wherein $X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is
- (1) a hydrogen atom,
- (2) fluorine,
- (3) chloro,
- (4) cyano
- (5) $C_{1-6}$ alkoxy, or
- (6) $C_{1-6}$ alkyl (wherein the alkyl is optionally substituted with 1 to 3 of the same or different substituents selected from the group consisting of halogen, hydroxy, and $C_{1-6}$ alkoxy), Y is
- (1) $C_{1-3}$ alkyl optionally substituted with 1 to 3 of the same or different substituents selected from the group consisting of fluorine, a $C_{3-6}$ alicyclic group, a 5- or 6-membered nitrogen-containing non-aryl heterocyclic group, phenyl (wherein the alicyclic group, the nitrogen-containing non-aryl heterocyclic group, and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
- (2) a alicyclic group optionally substituted with 1 to 3 of the same or different substituents selected from the group consisting of fluorine, amino, dimethylamino, $C_{1-3}$ alkyl optionally substituted with 1 to 3 fluorine, a 5- to 6-membered nitrogen-containing non-aryl heterocyclic group, phenyl (wherein the nitrogen-containing non-aryl heterocyclic group and the phenyl group are each independently optionally substituted with 1 to 3 of the same or different substituents selected from the group consisting of fluorine, cyano, alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy),
- (3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
- (4) phenyl optionally substituted with 1 to 3 of the same or different substituents selected from the group consisting of halogen, cyano, dimethylamino, $C_{1-3}$ alkoxy, and alkyl optionally substituted with 1 to 3 fluorine, or
- (5) 5- or 6-membered heteroaryl optionally substituted with 1 to 3 of the same or different substituents selected from the group consisting of halogen, cyano, dimethylamino, $C_{1-3}$ alkoxy, and $C_{1-3}$, alkyl optionally substituted with 1 to 3 fluorine, and Z is 6- to 10-membered heteroaryl, which is optionally substituted with 1 to 3 of the same or different substituents selected from the group consisting of fluorine, chloro, cyano, $C_{1-6}$ alkoxy, and $C_{1-3}$ alkyl optionally substituted with 1 to 3 fluorine or 1 $C_{1-6}$ alkoxy, and comprises 1 to 2 atoms independently selected from the group consisting of a nitrogen atom and an oxygen atom.

An embodiment of the compound represented by formula (1) includes the following (C).

(C)

A compound or a pharmaceutically acceptable salt thereof, wherein $X^1$ is $CR^4$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano, Y is
(1) $C_{1-3}$ alkyl optionally substituted with 1 to 3 fluorine,
(2) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine,
(3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
(4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or
(5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and
Z is 6- to 10-membered heteroaryl, which is optionally substituted with 1 to 3 of the same or different substituents selected from the group consisting of fluorine, chloro, cyano, $C_{1-6}$ alkoxy, and $C_{1-3}$ alkyl optionally substituted with 1 to 3 fluorine, and comprises 1 to 2 atoms independently selected from the group consisting of a nitrogen atom and an oxygen atom.

An embodiment of the compound represented by formula (1) includes the following (D).

(D)

A compound or a pharmaceutically acceptable salt thereof, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine,
(2) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
(3) phenyl optionally substituted with 1 to 3 of the same or different substituents selected from the group consisting of halogen, cyano, methoxy, and $C_{1-3}$ alkyl optionally substituted with 1 to 3 fluorine, or
(4) 5- or 6-membered heteroaryl optionally substituted with 1 to 3 of the same or different substituents selected from the group consisting of halogen, cyano, methoxy, and $C_{1-3}$ alkyl optionally substituted with 1 to 3 fluorine, and
Z is pyridyl, pyrimidinyl, indazolyl, or imidazopyridyl wherein the pyridyl, pyrimidinyl, indazolyl, or imidazopyridyl is optionally substituted with 1 to 3 of the same or different substituents selected from the group consisting of fluorine, chloro, cyano, methoxy, and $C_{1-3}$ alkyl optionally substituted with 1 to 3 fluorine.

An embodiment of the compound represented by formula (1) includes the following (E).

(E)

A compound or a pharmaceutically acceptable salt thereof, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) phenyl optionally substituted with 1 to 2 of the same or different substituents selected from the group consisting of fluorine, cyano, methoxy, and methyl, or
(2) 5- or 6-membered heteroaryl optionally substituted with 1 to 2 of the same or different substituents selected from the group consisting of fluorine, cyano, methoxy, and methyl, and
Z is pyridyl optionally substituted with 1 to 3 of the same or different substituents selected from the group consisting of fluorine, chloro, cyano, and $C_{1-3}$ alkyl optionally substituted with 1 to 3 fluorine.

An embodiment of the compound represented by formula (1) includes the following (F).

(F)

A compound or a pharmaceutically acceptable salt thereof, wherein
$X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) $C_{1-3}$ alkyl optionally substituted with 1 to 3 fluorine,
(2) a $C_{5-6}$ alicyclic group or phenylcyclopropyl wherein the $C_{5-6}$ alicyclic group or phenylcyclopropyl is optionally substituted with 1 to 3 of the same or different substituents selected from the group consisting of fluorine, amino, dimethylamino, and $C_{2-3}$ alkyl optionally substituted with 1 to 3 fluorine,
(3) a 4- to 6-membered nitrogen-containing non-aryl heterocyclic group, phenyloxetanyl, or tetrahydropyranyl wherein the 4- to 6-membered nitrogen-containing non-aryl heterocyclic group, phenyloxetanyl, or tetrahydropyranyl is optionally substituted with 1 to 3 of the same or different substituents selected from the group consisting of fluorine, amino, dimethylamino, $C_{2-3}$ alkyl optionally substituted with 1 to 3 fluorine, and phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy),
(4) phenyl optionally substituted with 1 to 3 of the same or different substituents selected from the group consisting of halogen, cyano, dimethylamino, $C_{1-3}$ alkoxy, and $C_{1-3}$, alkyl optionally substituted with 1 to 3 fluorine, or
(5) 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and Z is 6- to 10-membered heteroaryl optionally substituted with 1 to 3 of the same or different substituents selected from the group consisting of fluorine, chloro, cyano, $C_{2-5}$ alkoxy, and $C_{1-3}$ alkyl optionally substituted with 1 to 3 fluorine.

An embodiment of the compound represented by formula (1) includes the following (G).

(G)

A compound or a pharmaceutically acceptable salt thereof, wherein $X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) $C_{1-3}$ alkyl optionally substituted with 1 to 3 fluorine,
(2) a $C_{5-6}$ alicyclic group or phenylcyclopropyl wherein the $C_{5-6}$ alicyclic group or phenylcyclopropyl optionally substituted with 1 to 3 of the same or different substituents selected from the group consisting of fluorine, amino, dimethylamino, and $C_{2-3}$ alkyl optionally substituted with 1 to 3 fluorine,
(3) a 4- to 6-membered nitrogen-containing non-aryl heterocyclic group, phenyloxetanyl, or tetrahydropyranyl wherein the 4- to 6-membered nitrogen-containing non-aryl heterocyclic group, phenyloxetanyl, or tetrahydropyranyl is optionally substituted with 1 to 3 of the same or different substituents selected from the group consisting of fluorine, amino, dimethylamino, $C_{2-3}$ alkyl optionally substituted with 1 to 3 fluorine, and phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy),
(4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or
(5) 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, and Z is 6- to 10-membered heteroaryl, thienyl, pyrrolyl, thiazolyl, isothiazolyl, isoxazolyl, or thiadiazolyl wherein the 6- to 10-membered heteroaryl, thienyl, pyrrolyl, thiazolyl, isothiazolyl, isoxazolyl, or thiadiazolyl is optionally substituted with 1 to 3 of the same or different substituents selected from the group consisting of fluorine, cyano, $C_{2-6}$ alkoxy, and $C_{1-3}$ alkyl optionally substituted with 1 to 3 fluorine.

An embodiment of the compound represented by formula (1) includes the following (H).

(H)

A compound or a pharmaceutically acceptable salt thereof, wherein $X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) a $C_{5-6}$ alicyclic group optionally substituted with 1 to 3 of the same or different substituents selected from the group consisting of fluorine, amino, dimethylamino, and $C_{2-3}$ alkyl optionally substituted with 1 to 3 fluorine,
(2) a 5- or 6-membered nitrogen-containing non-aryl heterocyclic group optionally substituted with 1 to 3 of the same or different substituents selected from the group consisting of fluorine, amino, dimethylamino, and $C_{2-3}$ alkyl optionally substituted with 1 to 3 fluorine,
(3) phenyl optionally substituted with 1 to 3 of the same or different substituents selected from the group consisting of halogen, cyano, methoxy, and $C_{1-3}$ alkyl optionally substituted with 1 to 3 fluorine, or
(4) 6-membered heteroaryl optionally substituted with 1 to 3 of the same or different substituents selected from the group consisting of halogen, cyano, methoxy, and $C_{1-3}$ alkyl optionally substituted with 1 to 3 fluorine, and Z is pyridyl, pyrimidinyl, indazolyl, or imidazopyridyl wherein the pyridyl, pyrimidinyl, indazolyl, or imidazopyridyl is optionally substituted with 1 to 3 of the same or different substituents selected from the group consisting of fluorine, chloro, cyano, and $C_{1-3}$ alkyl optionally substituted with 1 to 3 fluorine.

An embodiment of the compound represented by formula (1) includes the following (I).

(I)

A compound or a pharmaceutically acceptable salt thereof, wherein $X^1$ is $CR^1$,
$X^2$ is $CR^2$,
$X^3$ is $CR^3$,
$X^4$ is $CR^4$,
$R^1$, $R^3$, and $R^4$ are all hydrogen atoms,
$R^2$ is fluorine or cyano,
Y is
(1) phenyl optionally substituted with 1 to 2 of the same or different substituents selected from the group consisting of fluorine, cyano, methoxy, and methyl, or
(2) 6-membered heteroaryl optionally substituted with 1 to 2 of the same or different substituents selected from the group consisting of fluorine, cyano, methoxy, and methyl, and Z is pyridyl optionally substituted with 1 to 3 of the same or different substituents selected from the group consisting of fluorine, chloro, cyano, and $C_{1-3}$ alkyl optionally substituted with 1 to 3 fluorine.

Examples of "pharmaceutically acceptable salt" include acid addition salts and base addition salts. Examples of acid addition salts include inorganic acid salts such as hydrochloric acid salt, hydrobromic acid salt, sulfuric acid salt, hydroiodic acid salt, nitric acid salt, and phosphoric acid salt, and organic acid salts such as citric acid salt, oxalic acid salt, phthalic acid salt, fumaric acid salt, maleic acid salt, succinic acid salt, malic acid salt, acetic acid salt, formic acid salt, propionic acid salt, benzoic acid salt, trifluoroacetic acid salt, methanesulfonic acid salt, benzenesulfonic acid salt, p-toluenesulfonic acid salt, and camphorsulfonic acid salt. Examples of base addition salts include inorganic base salts such as sodium salt, potassium salt, calcium salt, magnesium salt, barium salt, and aluminum salt, organic base salts such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, and N,N-dibenzylethylamine, and the like. Furthermore, examples of "pharmaceutically acceptable salt" include amino acid salts of an acidic amino acid or basic amino acid such as arginine, lysine, ornithine, aspartic acid, and glutamic acid.

Salts that are suitable for a raw material compound and intermediate and salts that are acceptable as a raw material of a pharmaceutical product are conventionally-used non-toxic salts. Such salts can be acid addition salts such as organic acid salts (e.g., acetic acid salt, trifluoroacetic acid salt, maleic acid salt, furamic acid salt, citric acid salt, tartaric acid salt, methanesulfonic acid salt, benzenesulfonic acid salt, formic acid salt, p-toluenesulfonic acid salt, etc.) and inorganic acid salts (e.g., hydrochloric acid salt, hydrobromic acid salt, hydroiodic acid salt, sulfuric acid salt, nitric acid salt, phosphoric acid salt, etc.), salts of amino acid (e.g., arginine, asparatic acid, glutamic acid, etc.), metal salts such as alkali metal salts (e.g., sodium salt, potassium salt, etc.) and alkali earth metal salts (e.g., calcium salt, magnesium salt, etc.), ammonium salts, organic base salts (e.g., trimethylamine salt, triethylamine salt, pyridine salt, picoline salt, dicyclohexylamine salt, N,N'-dibenzylethylenediamine salt, etc.), and the like. Those skilled in the art can also appropriately select other salts.

When it is desirable to obtain a salt of the compound of the present disclosure, the compound of the present disclosure can be directly purified if the compound is obtained in a form of a salt, and if the compound is obtained in a free form, the compound can be dissolved or suspended in a suitable organic solvent, and an acid or base is added to form a salt by a conventional method.

Deuterated compounds prepared by converting any one or more of 1H of a compound represented by formula (1) to 2H (D) are also encompassed by the compound represented by formula (1) in the present disclosure.

The present disclosure encompasses the compound represented by formula (1) and a pharmaceutically acceptable salt thereof. The compound of the present disclosure can also be in a form of a hydrate and/or solvate of various solvents (ethanolate, etc.) Thus, such hydrates and/or solvates are also encompassed by the compound of the present disclosure. Furthermore, the present disclosure also encompasses any tautomer, any existing stereoisomer, and crystalline forms in any form of the compound (1) of the present disclosure, and mixtures thereof.

Some of the compounds (1) of the present disclosure can be enantiomers based on an optically-active center, atropisomers based on axial or planar chirality resulting from restriction of intramolecular rotation, other stereoisomers, tautomers, geometric isomers, and the like. Meanwhile, all possible isomers and mixtures thereof, including the isomers mentioned, are encompassed within the scope of the present disclosure.

In particular, an enantiomer and an atropisomer can be obtained as a racemate and an optically-active form if an optically-active starting material or intermediate is used, respectively. If necessary, a corresponding starting material, intermediate, or final product racemate can be physically or chemically resolved, during an appropriate step of the manufacturing method described below, into their optical enantiomers by a known separation method, such as a method using an optically active column or a fractional crystallization method. Specifically, a diastereomer method, for example, forms two types of diastereomers from a racemate by a reaction using an optically active resolving agent. Since the different diastereomers generally have different physical properties, they can be resolved by a known method such as fractional crystallization.

While manufacturing methods of the compound of the present disclosure are described below, the manufacturing method of the compound of the present disclosure is not limited thereto.

The compound of the present disclosure can be manufactured by, for example, the manufacturing methods described below, but the method is not limited thereto. Such manufacturing methods can be appropriately modified based on the knowledge of those skilled in the art of organic synthetic chemistry. For the compounds used as a raw material, the salts thereof can also be used in the following manufacturing methods, as long as the reaction is not affected.

In the manufacturing methods described below, even if use of a protecting group is not specifically described, a functional group other than those at the reaction point can be protected as needed and deprotected after the completion of a reaction or after a series of reactions to obtain a compound of interest if one of the functional groups other than those at the reaction point is altered under the reaction condition or if it is unsuitable for post-reaction processing. Common protecting groups described in references (T. W. Greene and P. G. M. Nuts, "Protective Group in Organic Synthesis", $3^{rd}$ Ed., John Wiley and Sons, Inc., New York (1999)) or the like can be used as the protecting groups used in these processes. A protecting group can be introduced or removed by a method that is commonly used in organic synthetic chemistry (e.g., method described in the aforementioned reference or the like) or a method in accordance therewith.

The starting material and intermediate in the manufacturing methods described below can be purchased as a commercially available product or are available by synthesis in accordance with a method described in a known document or a known method from a known compound. Salts of the starting material and intermediate can also be used, as long as the reaction is not affected.

The intermediate and compound of interest in the manufacturing methods described below can also be converted into another compound encompassed by the present disclosure by appropriately converting their functional groups. A functional group can be converted by a method that is commonly used in organic synthetic chemistry (e.g., the method described in R. C. Larock, "Comprehensive Organic Transformations", $2^{nd}$ Ed., John Wiley and Sons, Inc., New York (1999) or the like) or a method in accordance therewith.

An inert solvent in the manufacturing methods described below refers to a solvent that does not react with raw materials, reagents, bases, acids, catalysts, ligands, or the like that are used in a reaction (hereinafter, also referred to as "raw materials or the like used in a reaction"). A solvent used in each step can be used as an inert solvent even if the solvent reacts with the raw materials or the like used in the reaction, as long as the reaction of interest proceeds to yield a compound of interest.

The compound of the present disclosure represented by formula (1) can be manufactured by, for example, the following Manufacturing Methods 1 to 4.

Manufacturing Method 1

The compound represented by formula (1), which can be represented by formula [A1], can be manufactured, for example, by the following manufacturing method.

[Chemical Formula 46]

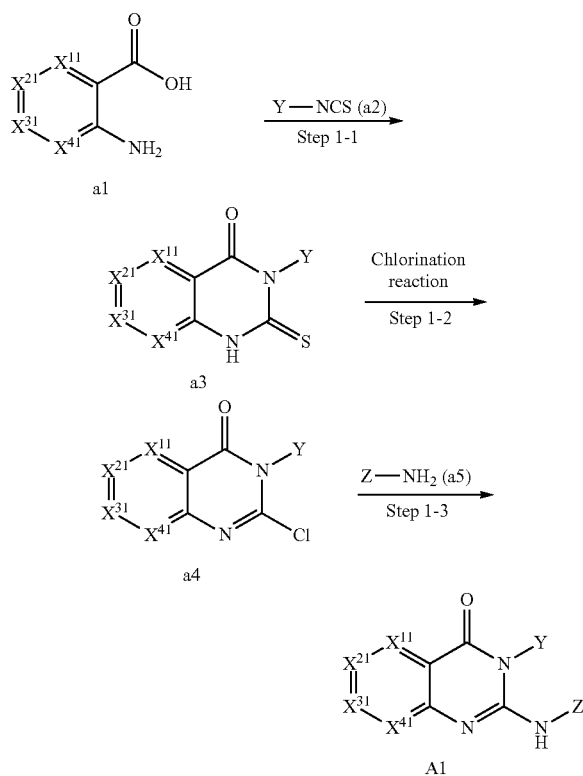

wherein $X^{11}$ is $CR^1$, $X^{21}$ is $CR^2$, $X^{31}$ is $CR^3$, $X^{41}$ is $CR^4$, and $R^1$, $R^2$, $R^3$, $R^4$, Y, and Z are defined the same as item 1.

As compound a1, a commercially available product can be used, or the compound can be manufactured in accordance with a known method, e.g., the method described in Anais da Academia Brasileira de Ciencias 2015, 87(3), 1525-1529 or the like.

As compound a2, a commercially available product can be used, or the compound can be manufactured in accordance with a known method, e.g., the method described in Synthetic Communications (2013), 43(24), 3342-3351, Journal of Organic Chemistry (1986), 51(13), 2613-15 or the like.

[Step 1-1: Cyclization Reaction]

Compound a3 can be manufactured by reacting compound a1 with compound a2 in the presence of a suitable base, without a solvent or in a suitable solvent, at normal pressure or under pressure. The base can be appropriately selected from the bases exemplified below or the like. Preferred examples thereof include triethylamine and N,N-diisopropylethylamine. The solvent can be appropriately selected from solvents exemplified below or the like. Preferred examples thereof include ethanol and isopropanol. The reaction time is generally 5 minutes to 48 hours, and preferably 1 hour to 12 hours. The reaction temperature is generally −78° C. to 150° C., and preferably 25° C. to 150° C.

This reaction can be performed in accordance with the method described in European Journal of Medicinal Chemistry 2016, 112, 106-113, Synthetic Communications 2017, 47(11), 1040-1045 or the like.

[Step 1-2: Chlorination Reaction]

Compound a4 can be manufactured by reacting compound a3 with a suitable chlorination reagent, without a solvent or in a suitable solvent. The solvent can be appropriately selected from the solvents exemplified below or the like. Preferred examples thereof include toluene and chloroform. The chlorination reagent should be appropriately selected in accordance with the type of raw material compound or the like. Examples thereof include phosphoryl chloride, phosphorus pentachloride, thionyl chloride, sulfuryl chloride, and the like. Such chlorination reagents are used alone or as a mixture of two or more chlorination reagents, preferably as a mixture of phosphoryl chloride and phosphorous pentachloride. The reaction time is generally 5 minutes to 48 hours, and preferably 1 hour to 12 hours. The reaction temperature is generally −78° C. to 150° C., and preferably 25° C. to 150° C.

This reaction can be performed in accordance with the method described in Journal of Medicinal Chemistry 2014, 57(5), 2091-2106, Bioorganic & Medicinal Chemistry 2010, 18(8), 2836-2848 or the like.

[Step 1-3: Substitution Reaction]

Compound A1 can be manufactured by reacting compound a4 with compound a5, without a solvent or in a suitable solvent, under normal pressure or under pressure. The solvent is appropriately selected from the solvents exemplified below or the like. Examples thereof include N-methylpyrrolidone, dimethyl sulfoxide, and the like. The reaction time is generally 5 minutes to 48 hours, and preferably 5 minutes to 12 hours. The reaction temperature is generally 0° C. to 250° C., and preferably 25° C. to 200° C. This reaction can be performed in the presence of a base as needed. The base is appropriately selected from the bases exemplified below or the like. Preferred examples thereof include lithium bis(trimethylsilyl)amide and potassium fluoride.

As compound a5, a commercially available product can be used, or the compound can be manufactured in accordance with a known method, e.g., the method described in The Journal of Organic Chemistry 2009, 74 (12), 4542-4546, Organometalics 2017, 36(2), 251-254 or the like.

Manufacturing Method 2

The compound represented by formula (1), which can be represented by formula [A1], can be manufactured, for example, by the following manufacturing method,

[Chemical Formula 47]

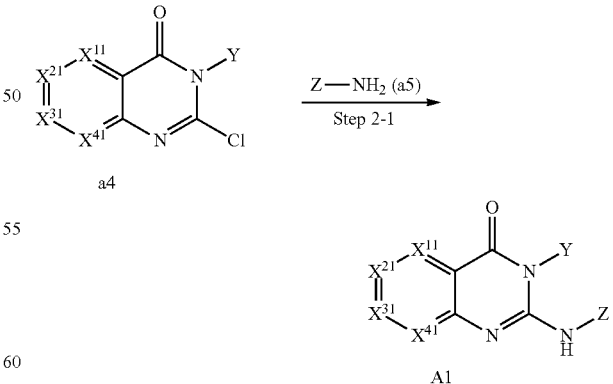

wherein $X^{11}$ is $CR^1$, $X^{21}$ is $CR^2$, $X^{31}$ is $CR^3$, $X^{41}$ is $CR^4$, and $R^1$, $R^2$, $R^3$, $R^4$, and Z are defined the same as item 1.

[Step 2-1: Coupling Reaction]

Compound A1 can be manufactured by coupling compound a4 with compound a5 in a suitable solvent in the presence of a catalyst and a base. Examples of catalysts include transition metals such as palladium, a salt thereof, a complex thereof, and those carried on a carrier such as a polymer. The base can be appropriately selected from the bases exemplified below or the like. Preferred examples thereof include cesium carbonate, potassium carbonate, and sodium t-butoxide. The solvent is appropriately selected from the solvents exemplified below or the like. Preferred examples thereof include toluene, xylene, dioxane, and N,N-dimethylformamide. The reaction time is generally 5 minutes to 48 hours, and preferably 30 minutes to 24 hours. The reaction temperature is generally 0° C. to 200° C., and preferably 20° C. to 160° C.

This reaction can be performed in accordance with the method described in International Publication No. WO 2016/105564.

Manufacturing Method 3

The compound represented by formula (1), which can be represented by formula [$C_1$], can be manufactured, for example, by the following manufacturing method.

[Chemical Formula 48]

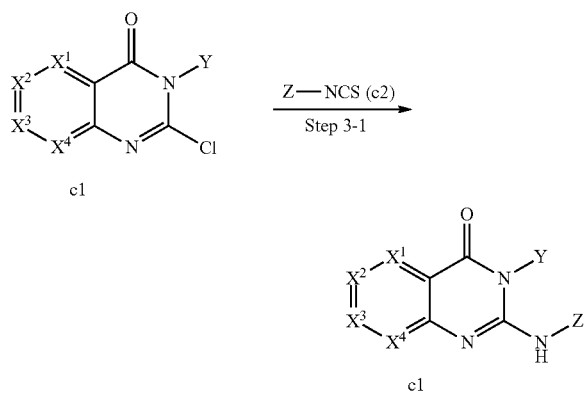

wherein $X^1$, $X^2$, $X^3$, $X^4$, Y and Z are defined the same as item 1.

[Step 3-1: Cyclization Reaction]

Compound $C_1$ can be manufactured by reacting compound c1 with compound c2 in the presence of copper bromide and a base, without a solvent or in a suitable solvent, under normal pressure or under pressure in accordance with the method described in Helvetica Chimica Acta (2016), 99(5), 378-383. The base can be appropriately selected from the bases exemplified below or the like. Preferred examples thereof include triethylamine and N,N-diisopropylethylamine. The solvent is appropriately selected from the solvents exemplified below or the like. Preferred examples thereof include N,N-dimethylformamide. The reaction time is generally 5 minutes to 48 hours, and preferably 1 hour to 48 hours. The reaction temperature is generally 0° C. to 150° C., and preferably 25° C. to 100° C.

As compound c1, a commercially available product can be used, or the compound can be manufactured in accordance with a known method, e.g., the method described in International Publication No. WO 2001/018536, International Publication No. WO 2001/19788, Journal of Medicinal Chemistry 1986, 29(8), 1534-1537, or the like.

As compound c2, a commercially available product can be used, or the compound can be manufactured from compound a5 in accordance with the manufacturing method of compound a2 in Manufacturing Method 1.

Manufacturing Method 4

The compound represented by formula (1), which can be represented by formula [$C_1$], can be manufactured, for example, by the following manufacturing method.

[Chemical Formula 49]

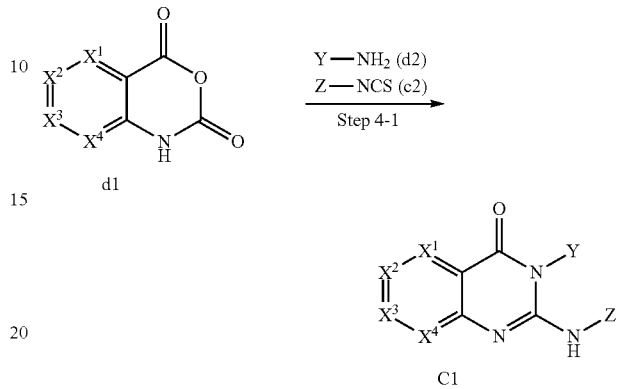

wherein $X^1$, $X^2$, $X^3$, $X^4$, Y, and Z are defined the same as item 1.

[Step 4-1: One-Pot Reaction]

Compound $C_1$ can be manufactured by reacting a solution obtained by reacting compound d1 with compound d2 in a suitable solvent under normal pressure or under pressure, with compound c2 in the presence of copper bromide and a base under normal pressure or under pressure. The base can be appropriately selected from the bases exemplified below or the like. Preferred examples thereof include triethylamine and N,N-diisopropylethylamine. The solvent is appropriately selected from the solvents exemplified below or the like. Preferred examples thereof include N,N-dimethylformamide. The reaction time is generally 5 minutes to 48 hours, and preferably 1 hour to 24 hours for both the reaction with compound d2 and the reaction with compound c2. The reaction temperature is generally 0° C. to 150° C., and preferably 25° C. to 100° C. for both the reaction with compound d2 and the reaction with compound c2.

As compound d1, a commercially available product can be used, or the compound can be manufactured in accordance with a known method, e.g., the method described in Journal of Medicinal Chemistry 2019, 62(3), 1468-1483 or the like.

As compound d2, a commercially available product can be used, or the compound can be manufactured in accordance with the manufacturing method of compound a5 in Manufacturing Method 1.

Manufacturing Method 5

The compound represented by formula (1), which can be represented by formula [A1], can be manufactured, for example, by the following manufacturing method.

[Chemical Formula 50]

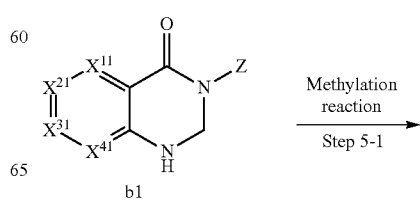

-continued

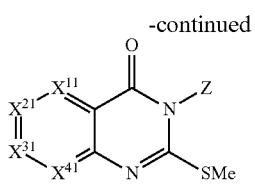

b2

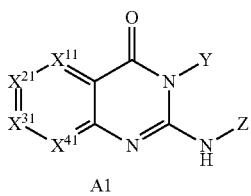

A1 wherein $X^{11}$ is $CR^1$, $X^{21}$ is $CR^2$, $X^{31}$ is $CR^3$, $X^{41}$ is $CR^4$, and $R^1$, $R^2$, $R^3$, $R^4$, Y, and Z are defined the same as item 1.

Compound b1 can be manufactured in accordance with the manufacturing method of compound a3 in Manufacturing Method 1.

[Step 5-1: Methylation Reaction]

Compound b2 can be manufactured by reacting compound b1 with a suitable methylation reagent in the presence of a suitable base, without a solvent or in a suitable solvent. The solvent is appropriately selected from the solvents exemplified below or the like. Preferred examples thereof include N,N-dimethylformamide. The methylation reagent should be appropriately selected in accordance with the type of raw material compound or the like. Examples thereof include iodomethane, dimethyl sulfate, and the like. The base can be appropriately selected from the bases exemplified below or the like. Preferred examples thereof include potassium carbonate. The reaction time is generally 5 minutes to 48 hours, and preferably 30 minutes to 24 hours. The reaction temperature is generally −78° C. to 150° C., and preferably 0° C. to 100° C.

This reaction can be performed in accordance with the method described in ChemMedChem 2009, 4(5), 866-876 or the like.

[Step 5-2: Substitution Reaction]

Compound A1 can be manufactured by reacting compound b2 with compound d2 in the presence of a suitable base, without a solvent or in a suitable solvent, under normal pressure or under pressure. The solvent is appropriately selected from the solvents exemplified below or the like. Examples thereof include tetrahydrofuran and the like. The base can be appropriately selected from the bases exemplified below or the like. Preferred examples thereof include potassium t-butoxide. The reaction time is generally 5 minutes to 48 hours, and preferably 5 hours to 12 hours. The reaction temperature is generally −78° C. to 150° C., and preferably 0° C. to 100° C.

The base used in each step of each of the manufacturing methods described above should be appropriately selected depending on the type of reaction or raw material compound or the like. Examples thereof include alkali bicarbonates such as sodium bicarbonate and potassium bicarbonate, alkali carbonates such as sodium carbonate, potassium carbonate, and cesium carbonate, metal fluorides such as potassium fluoride and cesium fluoride, metal hydrides such as sodium hydride and potassium hydride, alkali metal hydroxides such as sodium hydroxide and potassium hydroxide, alkali metal alkoxides such as sodium methoxide, sodium t-butoxide, and potassium t-butoxide, organic metal bases such as butyllithium, lithium diisopropylamide, and lithium bis(trimethylsilyl)amide, and organic bases such as triethylamine, diisopropylethylamine, pyridine, 4-dimethylaminopyridine (DMAP), 1,8-diazabicyclo[5.4.0]-7-undecene (DBU), and 1,4-diazabicyclo[2.2.2]ontane (DABCO).

The solvent used in each step of each of the manufacturing methods described above should be appropriately selected depending on the type of reaction or raw material compound or the like. Examples thereof include alcohols such as methanol, ethanol, and isopropanol, ketones such as acetone and methyl ketone, halogenated hydrocarbons such as methylene chloride and chloroform, ethers such as tetrahydrofuran (THF) and dioxane, aromatic hydrocarbons such as toluene, benzene, and xylene, aliphatic hydrocarbons such as hexane and heptane, esters such as ethyl acetate and propyl acetate, amides such as N,N-dimethylformamide (DMF) and N-methyl-2-pyrrolidone, sulfoxides such as dimethyl sulfoxide (DMSO), and nitriles such as acetonitrile. These solvents can be used alone or as a mixture of two or more solvents. An organic base can also be used as a solvent depending on the type of reaction.

The compound of the present disclosure represented by formula (1) or an intermediate thereof can be separated or purified by a method that is known to those skilled in the art. Examples thereof include extraction, partition, re-precipitation, column chromatography (e.g., silica gel column chromatography, ion exchange column chromatography, and preparative liquid chromatography), recrystallization, and the like.

Examples of recrystallization solvents that can be used include alcohol solvents such as methanol, ethanol, and 2-propanol, ether solvents such as diethyl ether, ester solvents such as ethyl acetate, aromatic hydrocarbon solvents such as benzene and toluene, ketone solvents such as acetone, halogen solvents such as dichloromethane and chloroform, hydrocarbon solvents such as hexane, aprotic solvents such as dimethylformamide and acetonitrile, water, mixtures thereof, and the like. The methods described in Jikken Kagaku Koza [Experimental Chemistry] (Ed. by The Chemical Society of Japan, Maruzen) Vol. 1 and the like can be used as other purification methods. The molecular structure of the compound of the present disclosure can be readily determined by a spectroscopic method such as nuclear magnetic resonance, infrared spectroscopy, or circular dichroism spectroscopy, or mass spectrometry by referring to the structure derived from each raw material compound.

The intermediate or final product in the manufacturing method described above can lead to another compound encompassed by the present disclosure by appropriately converting the functional group thereof, extending various side chains from especially an amino, hydroxyl group, carbonyl, halogen, or the like, and, in doing so, applying protection and deprotection described below as needed. Conversion of a functional group and extension of a side chain can be performed using a common method that is routinely used (see, for example, Comprehensive Organic Transformations, R. C. Larock, John Wiley & Sons Inc. (1999) or the like).

Examples of protecting groups of amino that can be used include alkylcarbonyl (e.g., acetyl and propionyl), formyl, phenylcarbonyl, alkyloxycarbonyl (e.g., methoxycarbonyl, ethoxycarbonyl, and tert-butoxycarbonyl), phenyloxycarbonyl, arylalkyloxycarbonyl (e.g., benzyloxycarbonyl), trityl, phthaloyl, tocyl, and benzyl.

Examples of protecting groups of carboxyl that can be used include alkyl (e.g., methyl, ethyl, propyl, isopropyl, butyl, and tert-butyl), phenyl, benzyl, trityl, and silyl (e.g., trimethylsilyl and tert-butyldimethylsilyl).

Examples of protecting groups of hydroxy that can be used include methyl, tert-butyl, allyl, substituted methyl (e.g., methoxymethyl and methoxyethoxymethyl), ethoxyethyl, tetrahydropyranyl, tetrahydrofuranyl, trityl, arylalkyl (e.g., benzyl), alkylcarbonyl (e.g., acetyl and propionyl), formyl, benzoyl, arylalkyloxycarbonyl (e.g., benzyloxycarbonyl), and silyl (e.g., trimethylsilyl and tert-butyldimethylsilyl).

Carbonyl can be protected by converting carbonyl into acyclic ketal (dimethyl ketal, diethyl ketal, or the like) or cyclic ketal (1,3-dioxolane, 1,3-dioxane, or the like).

The compound of the present disclosure represented by formula (1) or a pharmaceutically acceptable salt thereof can have asymmetry or a substituent having an asymmetric carbon. Such a compound has an enantiomer. The compound of the present disclosure also encompasses mixtures of each isomer and isolated isomers, which can be manufactured in accordance with a conventional method.

Examples of the manufacturing method include a method using a raw material having an asymmetric point and a method of introducing asymmetry during the process. Enantiomers for example can be obtained by using an optically active raw material, or performing optical resolution or the like at a suitable stage of a manufacturing step. Examples of optical resolution methods include a diastereomer method of forming a salt, when the compound represented by formula (1) or intermediate thereof has a basic functional group, in an inert solvent (e.g., an alcohol solvent such as methanol, ethanol, or 2-propanol; an ether solvent such as diethyl ether; an ester solvent such as ethyl acetate; a hydrocarbon solvent such as toluene; an aprotic solvent such as acetonitrile; or a mixture of two or more thereof) using an optically active acid (e.g., monocarboxylic acid such as mandelic acid, N-benzyloxyalanine, or lactic acid, dicarboxylic acid such as tartaric acid, ortho-diisopropylidene tartaric acid, or malic acid, or sulfonic acid such as camphorsulfonic acid or bromocamphorsulfonic acid).

When the compound of the present disclosure represented by formula (1) or an intermediate thereof has an acidic functional group such as a carboxyl group, optical resolution can be performed by forming a salt using an optically active amine (e.g., organic amines such as 1-phenylethylamine, quinine, quinidine, cinchonidine, cinchonine, or strychnine).

A temperature for the formation of a salt is selected from the range from −50° C. to the boiling point of a solvent, preferably the range from 0° C. to the boiling point, and more preferably the range from room temperature to the boiling point of a solvent. To improve the optical purity, it is desirable to first raise the temperature to a temperature near the boiling point of a solvent. When filtering out a precipitated salt, the temperature can be cooled as needed to improve the yield. The amount of an optically active acid or amine used in the range from about 0.5 to about 2.0 equivalents and preferably approximately 1 equivalent relative to a substrate is suitable. A crystal can be recrystallized in an inert solvent (e.g., an alcohol solvent such as methanol, ethanol, or 2-propanol; an ether solvent such as diethyl ether; an ester solvent such as ethyl acetate; a hydrocarbon solvent such as toluene; an aprotic solvent such as acetonitrile; or a mixture of two or more thereof) as needed to obtain an optically active salt with high purity. An optically resolved salt can also be treated with an acid or a base by a conventional method to obtain its free form as needed.

Raw materials and intermediates in each of the manufacturing methods described above without a specific description of the manufacturing method are commercially available compounds, or compounds that can be synthesized from a commercially available compound by a method known to those skilled in the art or a method in accordance thereto.

The present disclosure provides a pharmaceutical composition comprising the compound of the invention or a pharmaceutically acceptable salt thereof as an active ingredient for the treatment or prophylaxis of a disorder or disease associated with an abnormal nerve excitation. "Disorder or disease associated with an abnormal nerve excitation" refers to a disorder or disease of the central nervous system resulting from the breakdown in the balance between excitation signals and inhibition signals of the neural circuit. Examples thereof include epilepsy, developmental disorders (autism spectrum disorder, Rett syndrome, Angelman syndrome, fragile X syndrome, attention deficit hyperactivity disorder, etc.), mental disorders (schizophrenia, bipolar disorder, depression, anxiety, obsessive-compulsive disorder, etc.), and cognitive disorders (Alzheimer's disease, other dementia, Parkinson's disease, etc.). "Epilepsy" includes epileptic seizures, status epilepticus, epilepsy syndromes (Dravet syndrome, Ohtahara syndrome, West syndrome, Lennox-Gastaut syndrome, autosomal dominant nocturnal frontal lobe epilepsy, mesial temporal lobe epilepsy with hippocampal sclerosis, Rasmussen syndrome, etc.), epilepsy attributed to structural/metabolic etiology (cortical dysplasia, neurocutaneous syndrome (tuberous sclerosis complex, Sturge-Weber syndrome, etc.), etc.), etc., developmental disorder, mental disorder, or cognitive disorder manifested as a complication thereof, and the like. "Epileptic seizure" is a "transient occurrence of signs or symptoms due to abnormal excessive or synchronous neuronal activity in the brain" (Operational Classification of Seizure Types by the International League Against Epilepsy: official statement of the ILAE Commission for Classification and Terminology (Operational Classification of Seizure Types, Fisher, 2017), which includes, for example, generalized seizures including tonic, clonic, absence, myoclonic, and atonic seizures, focal seizure, and unknown seizures. "Disorder or disease associated with an abnormal nerve excitation" is preferably epilepsy or developmental disorder.

The effect of the compound of the present disclosure on epilepsy can be evaluated using, for example, activity to suppress hyperexcitation of cultured neurons or activity to suppress seizure or abnormal brainwave (spike, spike-and-wave, etc.) of an epilepsy animal model as an indicator. The effect on developmental disorder, mental disorder, or cognitive disorder can be evaluated, for example, through the three-chambered test using sociability of animal models as an indicator, repetitive grooming behavior test using repetitive stereotyped behavior as an indicator, marble burying test, spontaneous motor activity test using hyperkinetic behavior as an indicator, forced swim test using depression-like behavior as an indicator, novel object recognition test using cognitive function as an indicator, Y-maze test, or the like described in Buccafusco, Jerry J. "Methods of behavior analysis in neuroscience" Crc Press, 2008, or Silverman, Jill L., et al. "Behavioural phenotyping assays for mouse models of autism." Nature Reviews Neuroscience 11.7 (2010): 490-502.

As used herein, "prevention (prophylaxis)" is an act of administering an active ingredient of the present disclosure to a healthy individual who has not developed a disease in order to, for example, inhibit the onset of the disease. "Treatment (therapy)" is an act of administering an active ingredient of the present disclosure to a person (patient) diagnosed as having developed a disease by a physician.

The route of administration of the compound of the present disclosure can be oral administration, parenteral administration, or rectal administration. The daily dosage thereof varies by the type of compound, administration method, patient's symptom or age, or the like. For oral administration, generally about 0.01 to 1000 mg and still more preferably about 0.1 to 500 mg per 1 kg of body weight of a human or mammal can be administered in one to several doses. For parenteral administration such as intravenous administration, generally about 0.01 mg to 300 mg and still more preferably about 0.01 mg to 100 mg per 1 kg of body weight of a human or mammal can be administered.

The compound of the present disclosure can be administered directly or after being formulated into a suitable dosage form by parenteral or oral administration. Examples of the dosage form include, but are not limited to, a tablet, a capsule, powder, a granule, a liquid agent, a suspension, an injection, a patch, a poultice, and the like. A formulation can be manufactured by a known method using a pharmaceutically acceptable additive. An excipient, disintegrant, binding agent, fluidizer, lubricant, coating agent, solubilizing agent, solubilizing adjuvant, thickener, dispersant, stabilizing agent, sweetener, flavoring agent, and the like can be used as an additive in accordance with the objective. Specific examples thereof include lactose, mannitol, crystalline cellulose, low substituted hydroxypropyl cellulose, corn starch, partially pregelatinized starch, carmellose calcium, croscarmellose sodium, hydroxypropyl cellulose, hydroxypropylmethyl cellulose, polyvinyl alcohol, magnesium stearate, sodium stearyl fumarate, polyethylene glycol, propylene glycol, titanium oxide, talc, and the like.

The compound of the present disclosure can be used concomitantly with at least one other agent classified as an antiepileptic medicament, antidepressant, anxiolytic, or antipsychotic medicament. The combination can be administered for treatment of prophylaxis. Examples of agents calssified as an antiepileptic medicament include phenytoin, carbamazepine, oxcarbazepine, eslicarbazepine acetate, retigabine, lamotrigine, zonisamide, topiramate, sodium valproate, gabapentin, vigabatrin, pregabalin, phenobarbital, clonazepam, clobazam, diazepam, felbamate, rufinamide, ethosuximide, levetiracetam, brivaracetam, perampanel, stiripentol, cannabidiol, fenfluramine, and the like. Preferred examples include carbamazepine, lamotrigine, topiramate, sodium valproate, clonazepam, clobazam, ethosuximide, levetiracetam, stiripentol, cannabidiol, and fenfluramine. Examples of agents classified as an antidepressant include fluoxetine, fluvoxamine, paroxetine, sertraline, citalopram, and the like that are known as SSRI, duloxetine, milnacipran, and the like that are known as SNRI, and imipramine, amitriptyline, clomipramine, amoxapine, and the like that are known as tricyclic antidepressant. Examples of agents classified as an anxiolytic include etizolam, lorazepam, and the like that are known as benzodiazepine anxiolytic, and tandospirone and the like that are known as azapirone anxiolytic. Examples of agents classified as an antipsychotic medicament include haloperidol, spiperone, chlorpromazine, and the like that are known as typical antipsychotic medicament, and risperidone, quetiapine, olanzapine, clozapine, perospirone, aripiprazole, and the like that are known as SDA. An agent that can be used concomitantly with the compound of the present disclosure is abbreviated hereinafter as a concomitantly used agent.

The dosing period of the compound of the invention and a concomitantly used agent is not limited, which can be administered simultaneously to a subject of administration or adminsitered with a time lag. The compound of the invention and a concomitantly used agent can be prepared as a combined agent. The dosage of the concomitantly used agent can be appropriately selected based on the clinically used dose. The compounding ratio of the compound of the invention and a concomitantly used agent can be appropriately selected depending on the subject of admisnitration, route of administration, target disease, symptom, combination, or the like. If the subject of administration is, for example, a human, 0.01 to 100 parts by weight of concomitantly used agent can be used with respect to 1 part by weight of the compound of the invention. An agent such as an antiemetic, a hyptonic agent, or an antiseizure medicament (concomitantly used agent) can be used in combination in order to suppress side effects.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described herein.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

EXAMPLES

While the present disclosure is described more specifically with Reference Examples, Examples, and Test Examples hereinafter, the present disclosure is not limited thereto. The compound names denoted in the following Reference Examples and Examples do not necessarily follow the IUPAC nomenclature.

The following abbreviations may be used in the Reference Examples, Examples, and Tables in the Examples to simplify the descriptions herein. As abbreviations used for a substituent, Ph refers to phenyl. As abbreviations used for a reagent, TFA refers to trifluoroacetic acid, DMF refers to N,N-dimethylformamide, and HATU refers to 1-[bis(dimethylamino)methylene]-1H-1,2,3-triazolo[4,5-b]pyridinium-3-oxide hexafluorophosphate. As symbols used for NMR, s refers to singlet, d refers to doublet, dd refers to double doublet, dt refers to double triplet, td refers to triple doublet, t refers to triplet, q refers to quartet, m refers to multiplet, br refers to broad, brs refers to broad singlet, and J refers to a coupling constant.

High performance liquid chromatography-mass spectrometer; measurement conditions of LCMS are as follows. The observed mass spectrometry value [MS (m/z)] is indicated by $MH^+$, and time of retention is indicated by Rt (min). The measurement conditions used for measurement are described for each of the actual measurement values.

Measurement Condition A
   Detector: ACQUITY® SQ detector (Waters)
   HPLC: ACQUITY UPLC® SYSTEM
   Column: Waters ACQUITY UPLC® BEH C18 (1.7 um, 2.1 mm×30 mm)
   Solvent:
     Solution A; 0.05 formic acid/$H_2O$, solution B; acetonitrile Gradient Condition:
    0.0-1.3 minutes (linear gradient from B 10% to 95%)
    1.3-1.5 minutes (B 10%)
Flow rate: 0.8 ml/minute
UV: 220 nm and 254 nm
Column temperature: 40° C.
Measurement Condition B
Detector: ACQUITY® SQ detector (Waters)
HPLC: ACQUITY UPLC® SYSTEM
Column: Waters ACQUITY UPLC® BEH C18 (1.7 um, 2.1 mm×30 mm)
Solvent:
    Solution A; 0.06% formic acid/H$_2$O, solution B; 0.06% formic acid/acetonitrile
Gradient Condition:
    0.0-1.3 minutes (linear gradient from B 2% to 96%)
    1.3-1.5 minutes (B 96%)
    1.5-2.2 minutes (B 2%)
Flow rate: 0.8 ml/minute
UV: 220 nm and 254 nm
Column temperature: 40° C.
Measurement Condition C
Detector: Shimadzu LCMS-2020
Column: Phenomenex Kinetex (1.7 μm C18, 50 mm×2.10 mm)
Solvent:
    Solution A: 0.05% TFA/H$_2$O, solution B: 0.05% TFA/acetonitrile
Gradient Condition:
    0.0-1.7 minutes (linear gradient from B 1% to 99%)
    1.7-1.9 minutes (B 99%)
    1.9-3.0 minutes (B 1%)
Flow rate: 0.5 ml/minute
UV: 254 nm
Column temperature: 40° C.

Reference Example 1

2-chloro-3-phenylquinazolin-4(3H)-one

[Chemical Formula 51]

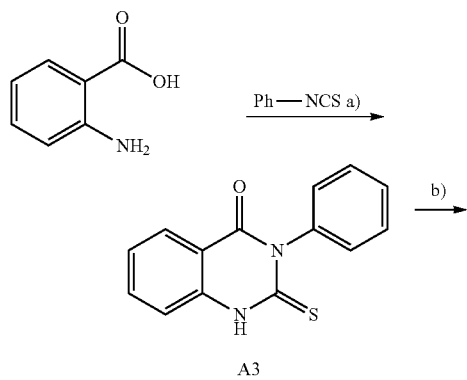

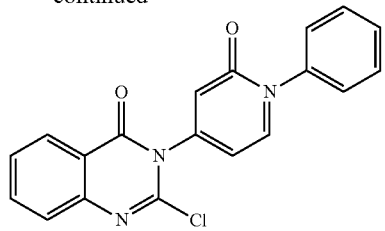

Reference Example 1 a) Manufacture of 3-phenyl-2-thioxo-2,3-dihydro-quinazolin-4(1H)-one (compound A3)

Phenyl isothiocyanate (2.6 ml) was added to an ethanol (70 ml) solution of anthranilic acid (2.0 g) and N,N-diisopropylethylaniine (6.4 ml), and the mixture was stirred for 16 hours while heating under reflux. After cooling the reaction solution to room temperature, the resulting solid was filtered out and washed with ethyl acetate and hexane. The solid was dried under reduced pressure at room temperature to obtain compound A3 (3.2 g).

$^1$H NMR (300 MHz, DMSO-d6) δ: 7.24-7.30 (2H, m), 7.32-7.52 (5H, m.), 7.76-7.82 (1H, m), 7.96 (1H, dd, J=8.0, 1.4 Hz), 13.05 (1H, s).

b) Manufacture of 2-chloro-3-phenylquinazolin-4(3H)-one (Reference Example 1)

A mixture of compound A3 (2.8 g), phosphorus pentachloride (3.7 g), and phosphorus oxychloride (21 ml) was stirred for 16 hours at 130° C. The reaction solution was poured into ice water. The resulting solid was filtered out and washed with water. The crude product was dissolved in ethyl acetate and washed with saturated saline and subsequently with saturated sodium bicarbonate water. The organic layer was dried with anhydrous magnesium sulfate, filtered, and concentrated under reduced pressure to obtain Reference Example 1 (2.0 g).

$^1$H-NMR (300 MHz, CDCl$_3$) δ: 7.30-7.35 m), 7.50-7.64 (4H, m), 7.79-7.92 (2H, m), 8.30 (1H, dd, J=7.9, 1.4 Hz).

Reference Example 2

2-amino-5-cyano-N-phenylbenzamide

[Chemical Formula 52]

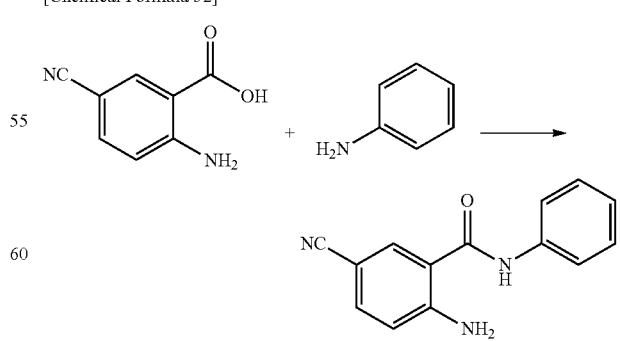

Reference Example 2

Aniline (1.15 g), N,N-diisopropylethylamine (1.75 g), and HATU (4.69 g) were added to a DMF (12 ml) solution of 2-amino-5-cyanobenzoic acid (2.00 g). The mixture was stirred for 20 hours at room temperature. Water was added to the reaction solution, and the eluted solid was filtered out to obtain Reference Example 2 (2.78 g).

LC-MS (measurement condition A), m/z; 238 (M+H)+ ESI, Rt; 0.76.

Reference Example 3

3-fluoro-5-isothiocyanatopyridine

[Chemical Formula 53]

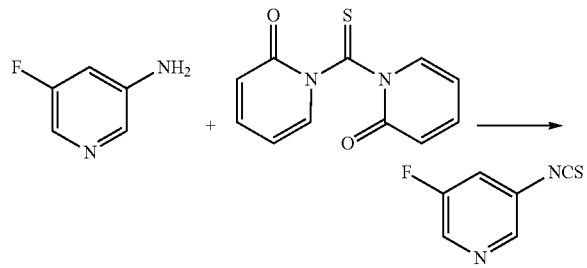

Reference Example 3

1,1'-thiocarbonylbis(pyridin 2(1H)-one) (1.15 g) was J added to a dichloromethane (10 ml) solution of 5-fluoropyridin-3-amine (0.56 g). The mixture was stirred for hour at room temperature. The reaction solution was purified by silica gel column chromatography (eluent; hexane: ethyl acetate) to obtain Reference Example 3 (0.5 g).

$^1$H-NMR (400 MHz, DMSO-d6) δ: 8.60-8.61 (2H, m), 8.03 (1H, d, J=9.6 Hz).

Reference Example 4

6-fluoro-3-(5-fluoropyridin-3-yl)-2-(methylthio) quinazolin-4(3H)-one

[Chemical Formula 54]

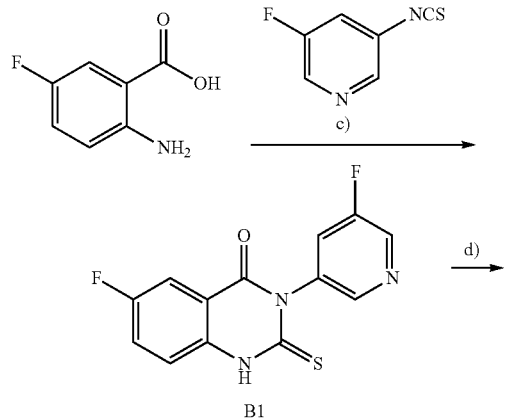

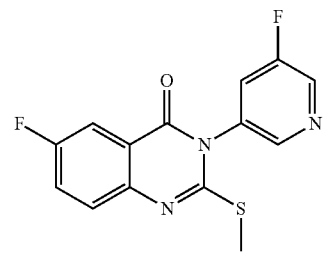

Reference Example 4 c) Manufacture of 6-fluoro-3-(5-fluoropyridin-3-yl)-2-thioxo-2,3-dihydroquinazolin-4(1H)-one (compound B1)

3-fluoro-5-isothiocyanatopyradine (5.8 q) and triethylamine (5.4 ml) were added to a dioxane (80 ml) solution of 2-amino-5-fluorobenzoic acid (4.0 g). The mixture was stirred for 2 hours at 85° C. After cooling the reaction solution to room temperature, the resulting solid was filtered out and washed with toluene. The solid was dried under reduced pressure at room temperature to obtain compound Bi (6.5 g).

$^1$H-NMR (400 MHz, DMSO-d6) δ: 7.51 (1H, dd, J=9.2, 4.3 Hz), 7.69-7.76 (2H, m), 7.87-7.91 (1H, m), 8.43-8.44 (1H, m), 8.65-8.66 (1H, m), 13.29 (1H, s).

b) Manufacture of 6-fluoro-3-(5-fluoropyridin-3-yl)-2-(methylthio)quinazolin-4(3H)-one (Reference Example 4)

Potassium carbonate (2.8 g) was added to a DMF (30 ml) solution of compound B1 (4.3 g). Iodomethane (1.0 ml) was added dropwise at 8 to 15° C. The mixture was stirred for 1.5 hours at the same temperature. After adding water to the reaction solution and stirring for 1 hour at room temperature, the resulting solid was filtered out and washed with water. The solid was dried under reduced pressure at room temperature to obtain Reference Example 4 (4.3 g).

$^1$H-NMR (400 MHz, DMSO-d6) δ: 2.53 (3H, s), 7.70-7.79 (3H, m), 8.16-8.19 (1H, m), 8.64-8.65 (1H, m), 8.82 (1H, d, J=3.1 Hz).

Reference Example 5

2-amino-5-cyano-N-(o-tolyl)benzamide

[Chemical Formula 55]

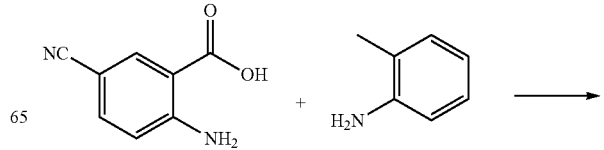

-continued

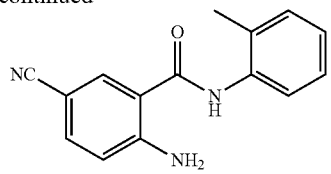

Reference Example 5

This was synthesized by the same method as Reference Example 2.

LC-MS (measurement condition A), m/z; 252 (M+H)+ ESI, Rt; 0.76.

Example 1

2-(benzo[d]oxazol-5-ylamino)-3-phenylquinazolin-4(3H)-one

[Chemical Formula 56]

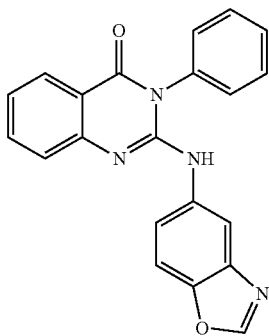

A DMF (2 ml) solution of Reference Example 1 (100 mg), N,N-dimethyl-4-aminopyridine (14 mg), and 1,3-benzoxazol-5-amine (104 mg) was stirred for 24 hours at 130° C. After concentrating the reaction solution, the crude product was purified by high performance liquid chromatography (eluent; water: acetonitrile) to obtain Example 1 (10 mg).

$^1$H-NMR (300 MHz, CDCl$_3$) δ: 6.16 (1H, brs), 7.25-7.33 (2H, m), 7.44-7.59 (4H, m), 7.64-7.74 (4H, m), 8.12 (1H, s), 8.21 (1H, dd, J=7.9, 1.6 Hz), 8.25 (1H, d, J=2.1 Hz).

Example 2

2-((1-methyl-1H-benzo[d]imidazol-6-yl)amino)-3-phenylquinazolin-4(3H)-one

[Chemical Formula 57]

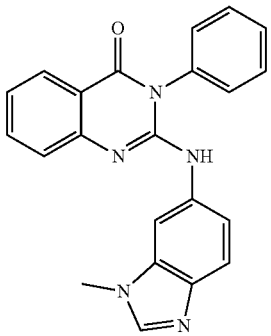

4,5-bis(diphenylphosphino)-9,9-dimethylxanthene (23 mg) and palladium acetate (9 mg) were added to a dioxane/DMF (1.2/0.4 ml) solution of Reference Example 1 (100 mg), 1-methyl-1H-benzimidazol-6-amine (63 mg), and cesium carbonate (250 mg). The mixture was stirred for 40 minutes at 160° C. The reaction solution was filtered through Celite, and the filtrate was concentrated. The resulting crude product was purified by high performance liquid chromatography (eluent; water: acetonitrile) to obtain Example 2 (13.0 mg).

$^1$H-NMR (300 MHz, CDCl$_3$) δ: 3.90 (3H, s), 6.13 (1H, brs), 6.87 (1H, dd, J=9.0, 3.0 Hz), 7.27-7.32 (1H, m), 7.46-7.55 (3H, m), 7.62-7.74 (5H, m), 7.89 (1H, s), 8.20-8.25 (2H, m).

Example 3

4-oxo-3-phenyl-2-(pyridin-3-ylamino)-3,4-dihydroquinazoline-6-carbonitrile

[Chemical Formula 58]

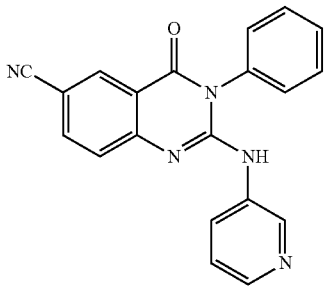

N,N-diisopropylethylamine (4.3 ml), 3-isothiocyanatopyridine (2.26 ml), and copper bromide (2.9 g) were added to a DMF (17 ml) solution of Reference Example 2 (4.0 g). The mixture was stirred for 3 hours at 85° C. Ammonium water was added to the reaction solution. The mixture was filtered through Celite. The filtrate was extracted with chloroform, and then washed with an aqueous saturated ammonium chloride solution, aqueous saturated sodium bicarbonate solution, water, and saturated saline. The organic layer was dried with anhydrous sodium sulfate, filtered, and concentrated under reduced pressure. The resulting crude product was recrystallized from acetonitrile to obtain Example 3 (1.52 g) as a crystal (type I crystal).

$^1$H-NMR (400 MHz, DMSO-d6) δ: 7.33-7.36 (2H, m), 7.51-7.63 (5H, m), 7.85 (1H, brs), 7.95 (1H, dd, J=8.5, 1.8 Hz), 8.19 (1H, brs), 8.29-8.30 (2H, m), 8.59 (1H, brs).

[Type I crystal] The X-ray powder diffraction pattern is shown in FIG. 1.

Major diffraction peaks: 2θ(°)=7.75, 10.32, 13.91, 15.50, 16.35, 21.23, 23.36, 23.87, 25.11, 25.93

Characteristic diffraction peaks: 2θ(°)=7.75, 10.32, 15.50, 23.36

Example 4

6-fluoro-2-((5-fluoropyridin-3-yl)amino)-3-(o-tolyl)quinazolin-4(3H)-one

[Chemical Formula 59]

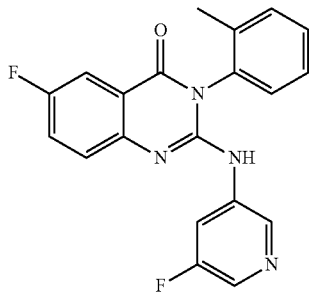

A DMF (1 ml) solution of 6-fluoro-2H-benzo[d][1,3]oxazine-2,4(1H)-dione (181 mg) and o-toluidine (113 mg) was stirred for 6 hours at 85° C., and then N,N-diisopropylethylamine (0.27 ml), Reference Example 3 (200 mg), and copper bromide (186 mg) were added to the reaction solution at room temperature. The mixture was stirred for 2 hours at 85° C. The reaction solution was filtered through Celite. The filtrate was extracted with chloroform, and then washed with an aqueous saturated ammonium chloride solution, water, and saturated saline. The organic layer was dried with anhydrous sodium sulfate, filtered, and concentrated under reduced pressure. The resulting crude product was recrystallized from acetonitrile to obtain Example 4 (83 mg).

$^1$H-NMR (400 MHz, DMSO-d6) δ: 2.10 (3H, s), 7.41-7.48 (5H, m), 7.57-7.68 (2H, m), 8.02 (2H, m), 8.25 (1H, d, J=1.8 Hz), 8.54 (1H, brs).

Example 5 to 232

The compounds shown in Tables 1-1 to 1-35 were obtained by the same method as Examples 1 to 4 by using a corresponding raw material compound.

TABLE 1-1

| Example | Structural formula | $^1$H NMR |
|---|---|---|
| 5 | | $^1$H NMR (400 MHz, DMSO-d6) δ: 7.43 (1H, d, J = 8.8 Hz), 7.54-7.64 (5H, m), 7.71-7.74 (1H, m), 7.93-7.99 (3H, m), 8.19 (1H, s), 8.32 (1H, s), 8.81-8.86 (2H, m). |
| 6 | | $^1$H NMR (400 MHz, DMSO-d6) δ: 7.38 (1H, d, J = 8.8 Hz), 7.51-7.54 (2H, m), 7.58-7.64 (3H, m), 7.69-7.72 (1H, m), 7.91 (1H, d, J = 2.4 Hz), 8.11 (1H, s), 8.87 (1H, s), 8.92 (2H, s). |

TABLE 1-1-continued

| Example | Structural formula | ¹H NMR |
|---|---|---|
| 7 | | ¹H NMR (400 MHz, DMSO-d6) δ: 7.31 (1H, d, J = 8.8 Hz), 7.34-7.37 (1H, m), 7.43 (1H, d, J = 8.8 Hz), 7.47-7.52 (1H, m), 7.53-7.55 (4H, m), 7.79 (1H, dd, J = 2.8, 8.8 Hz), 7.92-7.97 (1H, m), 8.05 (1H, d, J = 2.4 Hz), 8.31-8.33 (1H, m). |
| 8 | | ¹H NMR (400 MHz, DMSO-d6) δ: 2.43 (3H, s), 7.20 (1H, d, J = 8.5 Hz), 7.31 (1H, d, J = 8.5 Hz), 7.50-7.68 (6H, m), 7.74-7.79 (2H, m), 7.88 (1H, d, J = 2.4 Hz), 8.47 (1H, d, J = 2.4 Hz). |
| 9 | | ¹H NMR (400 MHz, DMSO-d6) δ: 7.33-7.70 (9H, m), 7.77 (1H, dd, J = 2.0, 8.4 Hz), 7.94 (1H, d, J = 2.4 Hz), 8.58 (1H, s). |
| 10 | | ¹H NMR (400 MHz, CDCl₃) δ: 3.81 (3H, s), 5.78 (1H, s), 6.95-7.02 (2H, m), 7.16-7.20 (2H, m), 7.28-7.35 (3H, m), 7.43 (1H, dd, J = 3.0, 9.1 Hz), 7.55 (1H, dd, J = 1.8, 7.3 Hz), 7.95 (1H, d, J = 2.4 Hz), 8.26 (1H, dd, J = 1.8, 4.9 Hz). |

TABLE 1-2

| Example | Structural formula | ¹H NMR |
|---|---|---|
| 11 | | ¹H NMR (400 MHz, CDCl₃) δ: 6.29 (1H, s), 7.34-7.40 (4H, m), 7.54-7.64 (4H, m), 8.09 (1H, d, J = 2.4 Hz), 8.45 (1H, d, J = 4.9 Hz), 9.77 (1H, s). |
| 12 | | ¹H NMR (400 MHz, DMSO-d6) δ: 7.31-7.40 (2H, m), 7.49-7.65 (7H, m), 7.76 (1H, s), 7.90-7.92 (1H, m), 8.24-8.26 (1H, m), 8.63 (1H, d, J = 1.8 Hz). |
| 13 | | ¹H NMR (400 MHz, CDCl₃) δ: 3.90 (3H, s), 5.91 (1H, s), 7.29-7.34 (2H, m), 7.43-7.51 (3H, m), 7.59 (1H, d, J = 2.8 Hz), 7.63-7.72 (3H, m), 8.21-8.23 (1H, m), 8.32 (1H, d, J = 5.6 Hz), 8.50 (1H, d, J = 2.4 Hz). |
| 14 | | ¹H NMR (400 MHz, CDCl₃) δ: 5.98 (1H, s), 7.29-7.35 (2H, m), 7.44-7.46 (2H, m), 7.53-7.56 (1H, m), 7.63-7.73 (4H, m), 8.20-8.25 (2H, m), 8.34 (1H, d, J = 6.0 Hz), 8.53 (1H, d, J = 2.4 Hz). |
| 15 | | ¹H NMR (400 MHz, DMSO-d6) δ: 7.45 (1H, d, J = 8.8 Hz), 7.62 (2H, s), 7.71-7.80 (4H, m), 7.95 (1H, d, J = 1.6 Hz), 8.37 (1H, s), 8.50 (1H, d, J = 5.2 Hz), 8.62 (1H, s), 8.95 (1H, s). |

TABLE 1-2-continued

| Example | Structural formula | ¹H NMR |
|---|---|---|
| 16 | (structure) | ¹H NMR (400 MHz, CDCl₃) δ: 5.95 (1H, brs), 6.71 (1H, dd, J = 9.8, 1.8 Hz), 7.40-7.42 (2H, m), 7.52 (1H, d, J = 8.5 Hz), 7.62-7.71 (5H, m), 8.14 (1H, d, J = 2.4 Hz), 8.82 (1H, s), 9.37 (1H, s). |

TABLE 1-3

| Example | Structural formula | ¹H NMR |
|---|---|---|
| 17 | (structure) | ¹H NMR (400 MHz, DMSO-d6) δ: 3.89 (3H, s), 7.19-7.25 (2H, m), 7.31 (1H, dd, J = 8.6, 4.3 Hz), 7.48-7.50 (2H, m), 7.55-7.63 (3H, m), 7.71 (1H, brs), 8.08 (1H, d, J = 7.9 Hz), 8.22 (1H, d, J = 4.3 Hz), 8.79 (1H, brs). |
| 18 | (structure) | ¹H NMR (400 MHz, CDCl₃) δ: 7.09 (1H, t, J = 6.7 Hz), 7.26-7.32 (2H, m), 7.37-7.46 (3H, m), 7.49-7.58 (2H, m), 7.64-7.72 (2H, m), 7.80 (1H, dd, J = 7.9, 3.0 Hz), 9.26 (1H, dd, J = 4.9, 1.8 Hz). |
| 19 | (structure) | ¹H NMR (400 MHz, CDCl₃) δ: 7.37-7.39 (2H, m), 7.44-7.49 (1H, m), 7.64-7.67 (4H, m), 7.84 (1H, dd, J = 7.9, 3.0 Hz), 8.12 (1H, brs), 8.93 (2H, brs). |

TABLE 1-3-continued

| Example | Structural formula | ¹H NMR |
|---|---|---|
| 20 | (6-fluoro-3-phenyl-2-(pyrimidin-4-ylamino)quinazolin-4(3H)-one) | ¹H NMR (400 MHz, CDCl₃) δ: 7.26-7.29 (2H, m), 7.48-7.69 (6H, m), 7.88-7.91 (1H, m), 8.33 (1H, brs), 8.96 (1H, brs). |
| 21 | (6-chloro-2-((2-(methoxymethyl)pyrimidin-4-yl)amino)-3-phenylquinazolin-4(3H)-one) | ¹H NMR (400 MHz, DMSO-d6) δ: 3.38 (3H, brs), 4.45 (2H, brs), 7.46-7.56 (7H, m), 7.86 (1H, dd, J = 8.7, 2.3 Hz), 7.97 (1H, d, J = 2.7 Hz), 8.48 (1H, brs). |
| 22 | (6-chloro-2-((6-methoxypyridin-3-yl)amino)-3-phenylquinazolin-4(3H)-one) | ¹H NMR (400 MHz, CDCl₃) δ: 3.85 (3H, s), 5.69 (1H, brs), 6.67 (1H, d, J = 8.6 Hz), 7.31-7.37 (3H, m), 7.50 (1H, dd, J = 8.6, 2.4 Hz), 7.53-7.63 (3H, m), 7.67 (1H, dd, J = 9.2, 3.1 Hz), 8.04 (1H, d, J = 2.4 Hz), 8.11 (1H, d, J = 2.4 Hz). |
| 23 | (6-chloro-2-((4-methoxypyridin-3-yl)amino)-3-phenylquinazolin-4(3H)-one) | ¹H NMR (400 MHz, CDCl₃) δ: 3.83 (3H, s), 5.90 (1H, brs), 7.02-7.08 (2H, m), 7.23-7.28 (2H, m), 7.38-7.43 (3H, m), 7.52 (1H, dd, J = 8.6, 2.4 Hz), 8.04 (1H, d, J = 2.4 Hz), 8.44 (1H, s), 8.65 (1H, d, J = 5.5 Hz). |

TABLE 1-4
| Example | Structural formula | ¹H NMR |
|---|---|---|
| 24 | 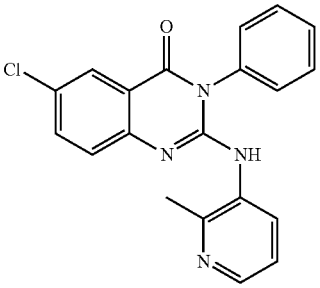 [SMILES: Cc1ncccc1Nc1nc2ccc(Cl)cc2c(=O)n1-c1ccccc1] | ¹H NMR (400 MHz, CDCl₃) δ: 2.07 (3H, s), 5.89 (1H, brs), 7.19 (1H, dd, J = 8.6, 4.9 Hz), 7.41-7.45 (3H, m), 7.57-7.71 (4H, m), 8.13 (1H, d, J = 2.4 Hz), 8.23 (1H, dd, J = 4.9, 1.8 Hz), 8.58 (1H, dd, J = 7.9, 1.2 Hz). |
| 25 | 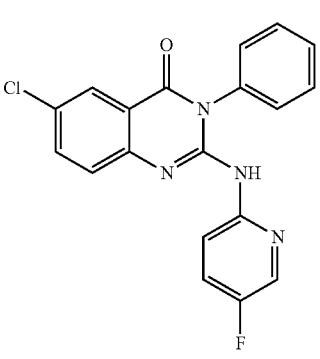 [SMILES: O=c1c2cc(Cl)ccc2nc(Nc2ccc(F)cn2)n1-c1ccccc1] | ¹H NMR (400 MHz, CDCl₃) δ: 7.08-7.12 (2H, m), 7.28-7.34 (2H, m), 7.41-7.47 (3H, m), 7.55-7.59 (2H, m), 7.69-7.73 (1H, m), 8.11 (1H, d, J = 2.4 Hz), 8.58 (1H, d, J = 3.1 Hz). |
| 26 | 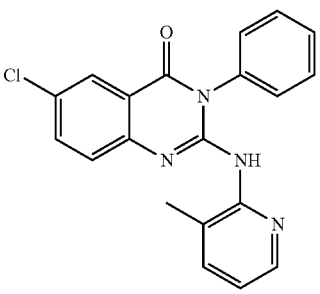 [SMILES: Cc1cccnc1Nc1nc2ccc(Cl)cc2c(=O)n1-c1ccccc1] | ¹H NMR (400 MHz, CDCl₃) δ: 2.18 (3H, s), 6.29 (1H, brs), 7.04 (1H, t, J = 7.3 Hz), 7.23-7.27 (2H, m), 7.37-7.42 (4H, m), 7.53 (1H, dd, J = 9.2, 2.4 Hz), 7.77-7.79 (1H, m), 8.08 (1H, d, J = 2.4 Hz), 8.55 (1H, dd, J = 4.9, 1.8 Hz). |
| 27 | 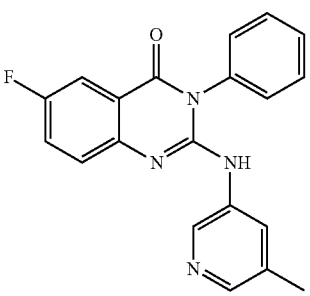 | ¹H NMR (400 MHz, CDCl₃) δ: 2.29 (3H, s), 5.88 (1H, brs), 7.32-7.39 (3H, m), 7.46 (1H, dd, 9.1, 4.9 Hz), 7.54-7.63 (3H, m), 7.75 (1H, dd, J = 8.5, 3.0 Hz), 7.81 (1H, brs), 8.10 (1H, brs), 8.38 (1H, brs). |
| 28 | 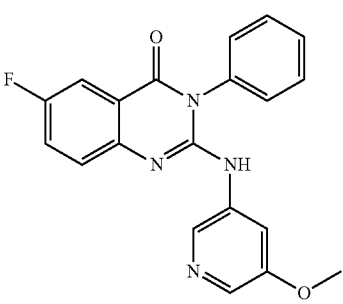 [SMILES: COc1cncc(Nc2nc3ccc(F)cc3c(=O)n2-c2ccccc2)c1] | ¹H NMR (400 MHz, CDCl₃) δ: 3.87 (3H, s), 6.17 (1H, brs), 7.34-7.40 (3H, m), 7.49 (1H, dd, 8.6, 4.9 Hz), 7.58-7.67 (3H, m), 7.77 (1H, dd, J = 8.6, 3.1 Hz), 7.95 (1H, brs), 8.08 (1H, brs), 8.18 (1H, brs). |

TABLE 1-4-continued

| Example | Structural formula | ¹H NMR |
|---|---|---|
| 29 | (6-fluoro-3-phenyl-2-((2-methylpyridin-3-yl)amino)quinazolin-4(3H)-one) | ¹H NMR (400 MHz, CDCl₃) δ: 2.03 (3H, s), 5.83 (1H, s), 7.16-7.19 (1H, m), 7.31-7.48 (4H, m), 7.56-7.66 (3H, m), 7.77 (1H, dd, J = 8.6, 3.1 Hz), 8.17 (1H, d, J = 3.7 Hz), 8.60 (1H, d, J = 7.9 Hz). |

TABLE 1-5

| Example | Structural formula | ¹H NMR |
|---|---|---|
| 30 | (6-fluoro-3-phenyl-2-((6-methylpyridin-3-yl)amino)quinazolin-4(3H)-one) | ¹H NMR (400 MHz, CDCl₃) δ: 2.50 (3H, s), 5.87 (1H, s), 7.11 (1H, d, J = 8.5 Hz), 7.31-7.45 (4H, m), 7.55-7.64 (3H, m), 7.74 (1H, dd, J = 8.5, 3.1 Hz), 7.92 (1H, dd, J = 8.5, 1.8 Hz), 8.44 (1H, d, J = 1.8 Hz). |
| 31 | (6-chloro-3-phenyl-2-(pyridin-3-ylamino)quinazolin-4(3H)-one) | ¹H NMR (400 MHz, DMSO-d6) δ: 7.33-7.36 (2H, m), 7.50-7.56 (2H, m), 7.56-7.63 (3H, m), 7.67 (1H, dd, J = 2.4, 8.4 Hz), 7.87-7.92 (3H, m), 8.28 (1H, d, J = 4.8 Hz), 8.62 (1H, d, J = 2.4 Hz). |
| 32 | (6,8-difluoro-3-phenyl-2-(pyridin-3-ylamino)quinazolin-4(3H)-one) | ¹H NMR (400 MHz, DMSO-d6) δ: 7.39 (1H, brs), 7.52-7.73 (7H, m), 7.94-7.98 (2H, m), 8.33 (1H, brs), 8.76 (1H, brs). |

TABLE 1-5-continued
| Example | Structural formula | ¹H NMR |
|---|---|---|
| 33 | 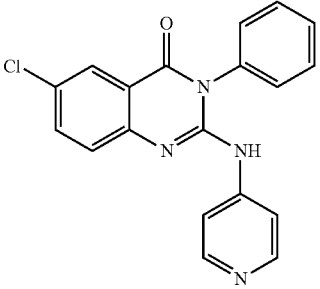 [SMILES: O=c1c2cc(Cl)ccc2nc(Nc2ccncc2)n1-c1ccccc1] | ¹H NMR (400 MHz, CDCl₃) δ: 6.16 (1H, s), 7.41-7.43 (2H, m), 7.52 (2H, d, J = 6.0 Hz), 7.58 (1H, d, J = 8.8 Hz), 7.66-7.73 (4H, m), 8.18 (1H, d, J = 2.8 Hz), 8.49 (2H, d, J = 0.4 Hz) |
| 34 | 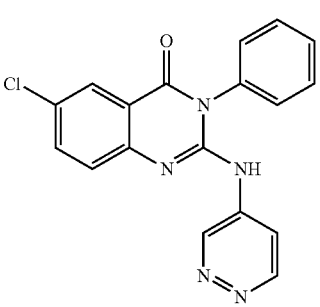 [SMILES: O=c1c2cc(Cl)ccc2nc(Nc2ccnnc2)n1-c1ccccc1] | ¹H NMR (400 MHz, CD3OD) δ: 7.45-7.48 (2H, m), 7.61-7.67 (4H, m), 7.75-7.78 (1H, m), 8.09 (1H, d, J = 2.4 Hz), 8.28 (1H, s), 8.95 (1H, s), 9.35 (1H, s). |
TABLE 1-6
| Example | Structural formula | ¹H NMR, LC-MS |
|---|---|---|
| 35 | 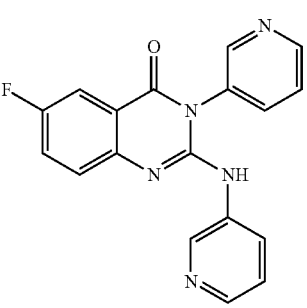 [SMILES: O=c1c2cc(F)ccc2nc(Nc2cccnc2)n1-c1cccnc1] | ¹H NMR (400 MHz, DMSO-d6) δ: 7.34-7.38 (1H, m), 7.41 (1H, dd, J = 9.1, 4.9 Hz), 7.57-7.68 (3H, m), 7.92 (1H, d, J = 8.5 Hz), 8.00-8.03 (1H, m), 8.09 (1H, s), 8.28 (1H, brs), 8.66 (1H, brs), 8.73-8.76 (2H, m). |
| 36 | 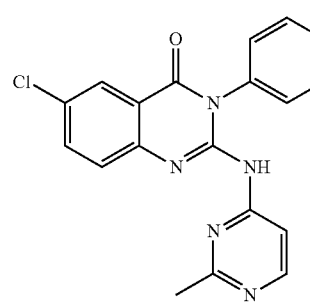 | ¹H NMR (400 MHz, CDCl₃) δ: 2.51 (3H, s), 6.85 (1H, s), 7.39-7.40 (2H, m), 7.57 (1H, d, J = 8.7 Hz), 7.66-7.71 (4H, m), 8.18 (1H, d, J = 2.3 Hz), 8.44 (1H, d, J = 5.5 Hz), 8.56 (1H, d, J = 6.0 Hz). |

TABLE 1-6-continued

| Example | Structural formula | ¹H NMR, LC-MS |
|---|---|---|
| 37 | | ¹H NMR (400 MHz, DMSO-d6) δ: 3.34 (3H, brs), 4.41 (2H, brs), 7.47-7.56 (6H, m), 7.70-7.75 (3H, m), 8.48 (1H, brs). |
| 38 | | ¹H NMR (400 MHz, DMSO-d6) δ: 7.48-7.64 (7H, m), 7.80 (1H, dd, J = 2.4, 8.8 Hz), 7.95 (1H, d, J = 2.4 Hz), 8.25-8.29 (2H, m), 8.50-9.50 (1H, brs). |
| 39 | | LC-MS (measurement condition B), m/z; 334 (M + H)+ ESI, Rt; 0.86 |
| 40 | | ¹H NMR (400 MHz, DMSO-d6) δ: 7.53-7.59 (3H, m), 7.65-7.75 (5H, m), 8.07-8.11 (2H, m), 8.32 (1H, d, J = 2.4 Hz), 8.62 (1H, brs). |

TABLE 1-7

| Example | Structural formula | ¹H NMR, LC-MS |
|---|---|---|
| 41 | | LC-MS (measurement condition B), m/z; 374 (M + H)+ ESI, Rt; 0.91 |
| 42 | | ¹H NMR (400 MHz, CDCl$_3$) δ: 2.46 (3H, s), 5.93 (1H, s), 7.26-7.31 (1H, m), 7.43-7.46 (3H, m), 7.52-7.54 (1H, m), 7.63-7.72 (3H, m), 7.99 (1H, s), 8.22-8.25 (1H, m), 8.32-8.34 (1H, m), 8.51 (1H, d, J = 2.4 Hz). |
| 43 | | ¹H NMR (400 MHz, CDCl$_3$) δ: 6.37 (1H, d, J = 8.0 Hz), 7.02-7.06 (1H, m), 7.18 (1H, d, J = 8.4 Hz), 7.34-7.36 (2H, m), 7.45-7.48 (1H, m), 7.51-7.56 (2H, m), 7.58-7.62 (2H, m), 8.17 (1H, d, J = 2.4 Hz), 8.43-8.44 (1H, m), 14.74 (1H, s). |
| 44 | | ¹H NMR (400 MHz, CDCl$_3$) δ: 1.72 (6H, d, J = 6.7 Hz), 2.95-3.05 (1H, m), 5.86 (1H, s), 7.11 (1H, d, J = 8.6 Hz), 7.33-7.38 (3H, m), 7.52-7.67 (4H, m), 7.89 (1H, dd, J = 8.6, 2.4 Hz), 8.06 (1H, d, J = 1.8 Hz), 8.45 (1H, d, J = 2.4 Hz). |
| 45 | | ¹H NMR (400 MHz, CDCl$_3$) δ: 6.14 (1H, brs), 7.39-7.45 (3H, m), 7.57 (1H, dd, J = 9.1, 4.9 Hz), 7.62-7.70 (3H, m), 7.82 (1H, dd, J = 8.5, 3.0 Hz), 8.26 (1H, brs), 8.41 (2H, brs). |

TABLE 1-7-continued

| Example | Structural formula | ¹H NMR, LC-MS |
|---|---|---|
| 46 | | LC-MS (measurement condition B), m/z; 364 (M + H)+ ESI, Rt; 1.00 |

TABLE 1

| Example | Structural formula | ¹H NMR |
|---|---|---|
| 47 | | ¹H NMR (400 MHz, CDCl$_3$) δ: 1.90 (3H, s), 5.70 (1H, brs), 7.07 (1H, brs), 7.30-7.45 (4H, m), 7.55-7.65 (3H, m), 7.75 (1H, dd, J = 8.6, 3.1 Hz), 8.23 (1H, brs), 9.23 (1H, brs). |
| 48 | | ¹H NMR (400 MHz, CDCl$_3$) δ: 6.21 (1H, brs), 7.40-7.46 (3H, m), 7.49-7.55 (1H, m), 7.63-7.71 (3H, m), 7.81-7.84 (1H, m), 8.56-8.59 (2H, m), 8.69 (1H, d, J = 1.8 Hz). |
| 49 | | ¹H NMR (400 MHz, CDCl$_3$) δ: 1.23 (3H, t, J = 7.3 Hz), 2.77 (2H, q, J = 7.3 Hz), 5.89 (1H, brs), 7.12 (1H, d, J = 8.6 Hz), 7.34-7.39 (3H, m), 7.52-7.65 (4H, m), 7.94 (1H, dd, J = 8.6, 2.4 Hz), 8.06 (1H, d, J = 2.4 Hz), 8.45 (1H, d, J = 2.4 Hz). |

TABLE 1-continued

| Example | Structural formula | ¹H NMR |
|---|---|---|
| 50 | | ¹H NMR (400 MHz, CDCl₃) δ: 1.22 (3H, t, J = 7.3 Hz), 2.74 (2H, q, J = 7.3 Hz), 5.83 (1H, brs), 7.10 (1H, d, J = 8.5 Hz), 7.31-7.44 (4H, m), 7.55-7.63 (3H, m), 7.74 (1H, dd, J = 8.5, 3.0 Hz), 7.90 (1H, dd, J = 8.5, 2.4 Hz), 8.43 (1H, d, J = 2.4 Hz). |
| 51 | | ¹H NMR (400 MHz, DMSO-d6): δ 7.35-7.39 (2H, m), 7.44 (1H, t, J = 7.6 Hz), 7.52 (1H, t, J = 9.6 Hz), 7.63-7.73 (3H, m), 7.91-7.92 (2H, m), 8.31 (1H, d, J = 4.8 Hz), 8.38 (1H, s), 8.64 (1H, d, J = 2.0 Hz). |
| 52 | | ¹H NMR (400 MHz, CDCl₃) δ: 1.21 (3H, t, J = 7.3 Hz), 2.61 (2H, q, J = 7.3 Hz), 5.89 (1H, brs), 7.32-7.36 (3H, m), 7.42-7.46 (1H, m), 7.55-7.64 (3H, m), 7.75 (1H, dd, J = 7.9, 2.4 Hz), 7.85 (1H, brs), 8.12 (1H, brs), 8.37 (1H, brs). |

TABLE 1-9

| Example | Structural formula | ¹H NMR |
|---|---|---|
| 53 | | ¹H NMR (400 MHz, CDCl₃) δ: 7.09-7.13 (1H, m), 7.29-7.33 (2H, m), 7.39-7.45 (3H, m), 7.60 (1H, dd, J = 8.6, 2.4 Hz), 7.69 (1H, d, J = 8.6 Hz), 8.12 (1H, d, J = 2.4 Hz), 8.18 (1H, dd, J = 8.6, 1.8 Hz), 8.97 (1H, brs). |

TABLE 1-9-continued

| Example | Structural formula | ¹H NMR |
|---|---|---|
| 54 | | ¹H NMR (300 MHz, CDCl₃) δ: 4.12 (3H, s), 6.18 (1H, s), 6.69 (1H, dd, J = 8.6, 1.8 Hz), 7.30-7.35 (1H, m), 7.44-7.50 (2H, m), 7.55-7.62 (2H, m), 7.63-7.76 (4H, m), 7.92 (1H, d, J = 1.0 Hz), 8.22-8.25 (1H, m). 8.35 (1H, m). |
| 55 | | ¹H NMR (400 MHz, DMSO-d6) δ: 1.52-1.61 (6H, m), 4.90 (0.5H, s), 5.50 (0.5H, s), 7.08 (0.5H, s), 7.18-7.42 (3H, m), 7.49-7.59 (1H, m), 7.86 (0.5H, s), 7.96 (1H, s), 8.13 (0.5H, s), 8.23-8.33 (1H, m), 8.69-8.82 (1H, m), 9.76 (0.5H, s). |
| 56 | | ¹H NMR (400 MHz, DMSO-d6) δ: 1.53-1.63 (2H, m), 1.77-1.85 (1H, m), 1.92-2.04 (3H, m), 2.21-2.27 (2H, m), 4.96 (0.5H, s), 5.67 (0.5H, s), 7.10 (0.5H, s), 7.23-7.38 (3H, m), 7.52-7.63 (1H, m), 7.89 (0.5H, s), 7.96-7.99 (1H, m), 8.18 (0.5H, s), 8.28 (1H, m), 8.74 (0.5, s), 8.94 (0.5H, s), 9.83 (0.5H, s). |
| 57 | | ¹H NMR (400 MHz, DMSO-d6) δ: 1.11-1.50 (3H, m), 1.58-1.71 (2H, m), 1.75-1.86 (3H, m), 2.53-2.69 (2H, m), 4.40-4.45 (0.5H, m), 5.10-5.15 (0.5H, m), 7.08 (0.5H, t, J = 7.4 Hz), 7.18-7.41 (3H, m), 7.49-7.53 (0.5H, m), 7.57-7.62 (0.5H, m), 7.83-7.96 (1.5H, m), 8.15 (0.5H, s), 8.24-8.30 (1H, m), 8.68 (0.5H, s), 8.82 (0.5H, s), 9.73 (0.5H, s). |
| 58 | | ¹H NMR (400 MHz, DMSO-d6) δ: 1.75-2.11 (6H, m), 2.85-2.93 (2H, m), 4.55 (0.5H, s), 5.30 (0.5H, s), 7.10 (0.5H, m), 7.21-7.41 (3H, m), 7.51-7.62 (1H, m), 7.86-7.94 (1.5H, m), 8.17 (0.5H, s), 8.24-8.31 (1H, m), 8.71 (0.5H, s), 8.90 (0.5H, s), 9.79 (0.5H, s). |

TABLE 1-9-continued

| Example | Structural formula | ¹H NMR |
|---|---|---|
| 59 | | ¹H NMR (400 MHz, DMSO-d6) δ: 1.49-1.65 (6H, m), 4.86-4.93 (0.7H, m), 5.47-5.54 (0.3H, m), 7.27-7.31 (1.3H, m), 7.33-7.41 (1H, m), 7.42-7.52 (1H, m), 7.55-7.65 (1H, m), 7.95-7.98 (0.7H, m), 8.17 (0.3H, d, J = 1.6 Hz), 8.24-8.29 (1H, m), 8.73 (0.7H, d, J = 2.8 Hz), 8.85 (0.7H, s), 9.81 (0.3H, s). |

TABLE 1-10

| Example | Structural formula | ¹H NMR |
|---|---|---|
| 60 | | ¹H NMR (400 MHz, DMSO-d6) δ: 1.60 (2H, s), 1.99 (4H, brs), 2.19-2.26 (2H, m), 4.96 (0.8H, s), 5.65 (0.2H, s), 7.29 (1H, dd, J = 9.0, 4.8 Hz), 7.38 (1H, brs), 7.49 (1H, m), 7.63 (1H, d, J = 6.0 Hz), 7.96 (1H, s), 8.28 (1H, s), 8.72 (0.8H, s), 8.96 (1H, s), 9.88 (0.2H, s). |
| 61 | | ¹H NMR (400 MHz, DMSO-d6) δ: 1.18-1.45 (3H, m), 1.64-1.83 (5H, m), 2.60-2.67 (2H, m), 4.43 (0.7H, s), 5.13 (0.3H, s), 7.23-7.28 (1.3H, m), 7.38-7.60 (3H, m), 7.89 (0.7H, s), 8.15 (0.3H, s), 8.29 (1H, s), 8.67 (0.7H, s), 8.85 (0.7H, s), 9.78 (0.3H, s). |
| 62 | | ¹H NMR (400 MHz, DMSO-d6) δ: 1.80-2.13 (6H, m), 2.88 (2H, m), 4.56 (0.7H, s), 5.27 (0.3H, s), 7.27-7.30 (1.3H, m), 7.39-7.61 (3H, m), 7.92 (0.7H, s), 8.19 (0.3H, s), 8.29 (1H, s), 8.69 (0.7H, s), 8.91 (0.7H, s), 9.85 (0.3H, s). |

TABLE 1-10-continued

| Example | Structural formula | ¹H NMR |
|---|---|---|
| 63 | | ¹H NMR (300 MHz, CDCl₃) δ: 6.64 (1H, s), 7.02 (1H, m), 7.11 (1H, t, J = 8.0 Hz), 7.19 (1H, s), 7.24-7.35 (3H, m), 7.42-7.49 (2H, m), 7.50-7.58 (2H, m), 7.60-7.68 (3H, m), 8.21 (1H, dd, J = 8.0, 1.5 Hz). |
| 64 | | ¹H NMR (300 MHz, CDCl₃) δ: 6.69-6.81 (2H, m), 7.13 (1H, t, J = 7.4 Hz), 7.30-7.38 (3H, m), 7.47-7.61 (3H, m), 7.66-7.75 (2H, m), 8.13 (1H, d, J = 2.3 Hz), 8.20-8.22 (1H, m), 8.70 (1H, d, J = 7.3 Hz). |
| 65 | | ¹H NMR (300 MHz, CDCl₃) δ: 6.56 (1H, s), 6.93-7.11 (2H, m), 7.15-7.19 (1H, m), 7.23-7.33 (2H, m), 7.42-7.49 (2H, m), 7.50-7.57 (2H, m), 7.58-7.67 (3H, m), 8.21 (1H, dd, J = 8.0, 1.5 Hz). |

TABLE 1-11

| Example | Structural formula | ¹H NMR |
|---|---|---|
| 66 | | ¹H NMR (300 MHz, CDCl₃) δ: 6.86 (1H, t, J = 7.2 Hz), 7.30-7.39 (2H, m), 7.48-7.51 (3H, m), 7.64-7.82 (6H, m), 8.26 (1H, dd, J = 8.2, 1.4 Hz), 8.56-8.59 (1H, m). |

TABLE 1-11-continued

| Example | Structural formula | ¹H NMR |
|---------|-------------------|--------|
| 67 | | ¹H NMR (300 MHz, CDCl₃) δ: 6.79-6.84 (2H, m), 7.33-7.51 (5H, m), 7.59-7.76 (5H, m), 8.21 (1H, dd, J = 8.0, 1.5 Hz). |
| 68 | | ¹H NMR (400 MHz, CDCl₃) δ: 5.77 (1H, s), 6.23 (1H, d, J = 9.6 Hz), 7.31-7.39 (2H, m), 7.40-7.49 (3H, m), 7.59-7.79 (5H, m), 8.20 (1H, s), 8.23 (1H, dd, J = 8.0, 1.5 Hz), 9.21 (1H, s). |
| 69 | | ¹H NMR (400 MHz, CD₃OD) δ: 6.91 (1H, t, J = 7.0 Hz), 7.11-7.18 (2H, m), 7.25-7.37 (4H, m), 7.41-7.50 (3H, m), 7.68-7.75 (1H, m), 8.07-8.12 (1H, m), 8.46 (1H, d, J = 7.2 Hz), 8.51 (1H, s). |
| 70 | | ¹H NMR (400 MHz, CDCl₃) δ: 6.23 (1H, s), 6.84-6.90 (1H, m), 7.09-7.18 (1H, m), 7.30-7.39 (3H, m), 7.50-7.60 (3H, m), 7.67-7.75 (1H, m), 7.76-7.87 (3H, m), 8.17-8.24 (1H, m), 8.41 (1H, d, J = 7.1 Hz). |

TABLE 1-11-continued

| Example | Structural formula | ¹H NMR |
|---|---|---|
| 71 | | ¹H NMR (500 MHz, CDCl₃) δ: 1.66-1.76 (1H, m), 1.95-2.07 (3H, m), 2.43 (1H, m), 2.48 (3H, s), 2.88 (1H, dd, J = 7.0, 1.4 Hz), 3.07 (1H, d, J = 14.0 Hz), 3.17 (1H, m), 5.97 (1H, s), 7.20-7.23 (1H, m), 7.33 (1H, dd, J = 8.5, 4.5 Hz), 7.42 (1H, d, J = 8.0 Hz), 7.60-7.64 (1H, m), 8.16 (1H, dd, J = 8.0, 1.3 Hz), 8.31 (1H, dd, J = 4.5, 1.0 Hz), 8.54 (1H, d, J = 8.5 Hz), 8.69 (1H, d, J = 2.3 Hz). |

TABLE 1-12

| Example | Structural formula | ¹H NMR, LC-MS |
|---|---|---|
| 72 | | ¹H NMR (400 MHz, CD₃OD) δ: 2.44 (6H, brs), 2.95 (6H, t, J = 7.4 Hz), 7.07 (1H, brs), 7.21 (1H, brs), 7.33 (1H, dd, J = 8.0 4.8 Hz), 7.48 (2H, dd, J = 8.6, 2.8 Hz), 8.13 (2H, dd, J = 4.8, 1.2 Hz). |
| 73 | | ¹H NMR (500 MHz, CD₃OD) δ: 1.23 (3H, s), 1.62-1.69 (2H, m), 1.74-1.77 (4H, m), 2.87 (2H, m), 4.83 (1H, m) 7.20 (2H, m), 7.44-7.58 (3H, m), 8.03 (1H, d, J = 7.3 Hz), 8.28 (2H, m) |
| 74 | | ¹H NMR (400 MHz, CD₃OD) δ: 1.24 (3H, s), 1.47-1.54 (2H, m), 1.59-1.67 (4H, m), 2.81-2.89 (2H, m), 4.88 (1H, brs), 7.05-7.08 (2H, m), 7.32-7.35 (1H, m), 7.42-7.46 (1H, m), 7.52 (1H, brs), 7.88 (1H, dd, J = 8.0, 1.2 Hz), 8.14 (1H, dd, J = 8.4, 1.2 Hz), 8.24 (1H, s). |

TABLE 1-12-continued

| Example | Structural formula | ¹H NMR, LC-MS |
|---|---|---|
| 75 | | LC-MS (measurement condition A), m/z; 336 (M + H)+ ESI, Rt; 0.29 |
| 76 | | ¹H NMR (500 MHz, DMSO-d6) δ: 1.66 (1H, s), 1.77 (1H, d, J = 7.0 Hz), 2.02-2.26 (8H, m), 2.39-2.46 (1H, m), 3.25 (2H, s), 4.75-4.83 (0.5H, m), 5.51-5.59 (0.5H, m), 7.08 (0.5H, t, J = 7.3 Hz), 7.17-7.24 (1.5H, m), 7.29-7.39 (1.5H, m), 7.50 (0.5H, t, J = 7.7 Hz), 7.59 (0.5H, t, J = 7.0 Hz), 7.86 (0.5H, d, J = 8.5 Hz), 7.89-7.93 (0.5H, m), 7.96 (0.5H, d, J = 8.5 Hz), 8.17 (0.5H, s), 8.23-8.28 (1H, m), 8.71 (0.5H, s), 9.07 (0.5H, s), 9.80 (0.5H, s). |
| 77 | | ¹H NMR (500 MHz, DMSO-d6) δ: 2.10 (1H, m), 2.30 (1H, m), 2.37-2.42 (1H, m), 2.53 (3H, s), 2.61-2.64 (1H, m), 3.26-3.32 (1H, m), 3.39 (1H, t, J = 8.0 Hz), 6.25 (1H, m), 7.22 (1H, t, J = 7.5 Hz), 7.35 (1H, d, J = 8.0 Hz), 7.42 (1H, dd, J = 8.2, 4.5 Hz), 7.65 (1H, t, J = 7.0 Hz), 7.99 (1H, d, J = 8.0 Hz), 8.27 (1H, m), 8.38 (1H, d, J = 8.0 Hz), 8.84 (1H, s), 12.50 (1H, s). |
| 78 | | ¹H NMR (400 MHz, DMSO-d6) δ: 1.59-1.75 (2H, m), 2.04-2.12 (2H, m), 2.23 (3H, s), 2.90-2.92 (4H, m), 4.39 (0.5H, s), 5.13 (0.5H, s), 7.06-7.10 (0.5H, m), 7.22-7.37 (3H, m), 7.50-7.60 (1H, m), 7.86-7.97 (1.5H, m), 8.17 (0.5H, s), 8.25-8.29 (1H, m), 8.69 (0.5H, s), 8.87 (0.5H, s), 9.77 (0.5H, s). |

TABLE 1-13

| Example | Structural formula | ¹H NMR, LC-MS |
|---|---|---|
| 79 | | ¹H NMR (400 MHz, CD₃OD) δ: 1.43-1.70 (2H, m), 1.84-1.93 (2H, m), 2.09-2.25 (2H, m), 3.00 (3H, s), 3.09-3.18 (2H, m), 3.42 (2H, brs), 5.76 (1H, brs), 7.17 (2H, m), 7.39-7.67 (3H, m), 8.02 (1H, d, J = 7.6 Hz), 8.15-8.49 (2H, m). |
| 80 | | ¹H NMR (400 MHz, CD₃OD) δ: 1.66 (2H, brs), 1.84-1.93 (2H, m), 2.18 (2H, brs), 2.55 (3H, s), 2.94 (2H, brs), 3.43 (2H, s), 5.71 (1H, brs), 7.25 (1H, brs), 7.32-7.41 (1H, m), 7.44-7.50 (1H, m), 7.66-7.95 (2H, m), 8.24-8.76 (2H, m). |
| 81 | | ¹H NMR (500 MHz, CDCl₃) δ: 1.74 (1H, m), 1.96-2.08 (3H, m), 2.39 (1H, s), 2.48 (3H, s), 2.87-2.89 (1H, m), 3.06 (1H, d, J = 14.0 Hz), 3.19-3.20 (1H, m), 5.94 (1H, s), 7.30-7.38 (2H, m), 7.41 (1H, dd, J = 8.9, 4.9 Hz), 7.79 (1H, dd, J = 8.7, 2.9 Hz), 8.31 (1H, d, J = 4.1 Hz), 8.47 (1H, d, J = 7.2 Hz), 8.69 (1H, s), 13.16 (1H, s). |
| 82 | | ¹H NMR (500 MHz, CDCl₃) δ: 2.19-2.26 (1H, m), 2.34-2.40 (1H, m), 2.49-2.55 (1H, m), 2.60 (3H, s), 2.68 (1H, dd, J = 9.0, 10.0 Hz), 3.22 (1H, d, J = 11.0 Hz), 3.42 (1H, t, J = 8.9 Hz), 6.42-6.44 (1H, m), 7.32-7.37 (2H, m), 7.41-7.44 (1H, m), 7.80 (1H, dd, J = 8.5, 3.0 Hz), 8.31 (1H, d, J = 3.9 Hz), 8.50-8.53 (1H, m), 8.74 (1H, s), 12.08 (1H, s). |
| 83 | | LC-MS(measurement condition A), m/z; 348 (M + H)+ ESI, Rt; 0.32 |

TABLE 1-14
| Example | Structural formula | ¹H NMR, LC-MS |
|---|---|---|
| 84 | 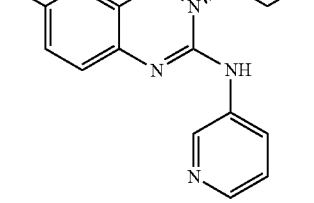 | LC-MS(measurement condition A), m/z; 368 (M + H)+ ESI, Rt; 0.36 |
| 85 | 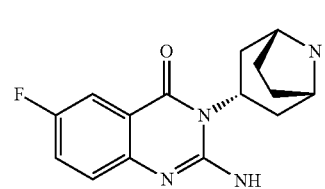 | LC-MS(measurement condition A), m/z; 380 (M + H)+ ESI, Rt; 0.38 |
| 86 | 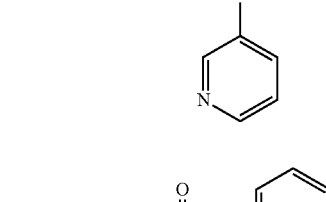 | ¹H NMR (500 MHz, DMSO-d6) δ: 2.40 (3H, s), 7.09 (1H, d, J = 8.0 Hz), 7.17 (1H, s), 7.34 (1H, dd, J = 8.2, 4.7 Hz), 7.49 (2H, d, J = 7.2 Hz), 7.55-7.63 (3H, m), 7.72 (1H, s), 7.86 (1H, d, J = 8.0 Hz), 7.94 (1H, d, J = 8.2 Hz), 8.26 (1H, d, J = 3.8 Hz), 8.65 (1H, d, J = 2.2 Hz). |
| 87 | 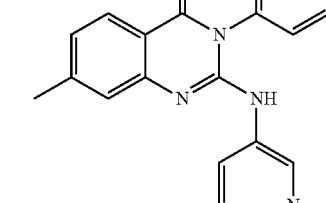 | LC-MS(measurement condition A), m/z; 333 (M + H)+ ESI, Rt; 0.78 |
| 88 | 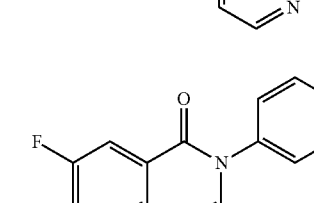 | LC-MS(measurement condition A), m/z; 340 (M + H)+ ESI, Rt; 0.80 |

TABLE 1-14-continued

| Example | Structural formula | 1H NMR, LC-MS |
|---|---|---|
| 89 | | LC-MS(measurement condition A), m/z; 368 (M + H)+ ESI, Rt; 0.40 |
| 90 | | 1H NMR (400 MHz, CD3OD) δ: 2.34 (3H, s), 2.65-2.91 (4H, m), 3.28 (2H, s), 3.45 (2H, s), 4.76-4.80 (1H, m), 7.35-7.47 (3H, m), 7.67 (1H, dd, J = 8.8, 2.8 Hz), 8.07 (1H, brs), 8.27 (1H, d, J = 4.4 Hz), 8.70 (1H, brs). |

TABLE 1-15

| Example | Structural formula | 1H NMR |
|---|---|---|
| 91 | | 1H NMR (500 MHz, DMSO-d6) δ: 6.95-6.99 (1H, m) 7.11 (1H, d, J = 8.2 Hz), 7.34-7.37 (1H, m) 7.51 (2H, d, J = 7.2 Hz), 7.55-7.66 (4H, m), 7.87 (1H, s), 7.91 (1H, d, J = 8.6 Hz), 8.28 (1H, d, J = 4.0 Hz), 8.63 (1H, m). |
| 92 | | 1H NMR (400 MHz, DMSO-d6) δ: 3.79 (3H, s), 6.76 (1H, d, J = 8.2 Hz), 6.85 (1H, d, J = 8.1 Hz), 7.33 (1H, dd, J = 8.2, 4.6 Hz), 7.44 (2H, d, J = 7.4 Hz), 7.53-7.62 (4H, m), 7.67 (1H, s), 7.93 (1H, d, J = 8.3 Hz), 8.25 (1H, d, J = 4.4 Hz), 8.64 (1H, d, J = 2.4 Hz). |

TABLE 1-15-continued

| Example | Structural formula | ¹H NMR |
|---|---|---|
| 93 | | ¹H NMR (300 MHz, CDCl₃) δ: 3.81 (3H, s), 7.08 (1H, d, J = 8.1 Hz), 7.29-7.43 (2H, m), 7.45-7.56 (3H, m), 7.62-7.80 (6H, m), 8.24 (1H, d, J = 7.9 Hz), 8.63 (1H, d, J = 8.0 Hz). |
| 94 | | ¹H NMR (300 MHz, DMSO-d6) δ: 6.39-6.48 (2H, m), 6.49-6.56 (2H, m), 7.41-7.65 (8H, m), 7.76-7.82 (1H, m), 8.09-8.16 (1H, m). |
| 95 | | ¹H NMR (400 MHz, CDCl₃) δ: 4.20 (3H, s), 6.14 (1H, brs), 7.05-7.14 (1H, m), 7.26-7.36 (4H, m), 7.45 (2H, d, J = 8.0 Hz), 7.57-7.76 (4H, m), 7.91 (1H, s), 8.23 (1H, dd, J = 7.9, 1.5 Hz). |
| 96 | | ¹H NMR (500 MHz, CDCl₃) δ: 2.14-2.25 (1H, m), 2.30-2.38 (1H, m), 2.45-2.54 (1H, m), 2.58 (3H, s), 2.66 (1H, dd, J = 11.5, 9.0 Hz), 3.21 (1H, d, J = 11.5 Hz), 3.39 (1H, t, J = 9.0 Hz), 6.43-6.46 (1H, m), 7.20 (1H, t, J = 7.5 Hz), 7.31 (1H, dd, J = 8.5, 4.5 Hz), 7.41 (1H, d, J = 8.0 Hz), 7.58-7.62 (1H, m), 8.15 (1H, dd, J = 8.0, 1.0 Hz), 8.29 (1H, d, J = 4.0 Hz), 8.55 (1H, d, J = 8.5 Hz), 8.71 (1H, s), 12.05 (1H, s). |

TABLE 1-16

| Example | Structural formula | ¹H NMR, LC-MS |
|---|---|---|
| 97 | | ¹H NMR (500 MHz, CDCl₃) δ: 2.17-2.23 (1H, m), 2.31-2.38 (1H, m), 2.46-2.53 (1H, m), 2.57 (3H, s), 2.66 (1H, dd, J = 11.4, 9.4 Hz), 3.20 (1H, d, J = 11.6 Hz), 3.39 (1H, t, J = 8.8 Hz), 6.39-6.45 (1H, m), 7.29-7.41 (3H, m), 7.78 (1H, dd, J = 8.4, 2.8 Hz), 8.30 (1H, s), 8.49 (1H, d, J = 8.4 Hz), 8.72 (1H, s), 12.06 (1H, s) |
| 98 | | ¹H NMR (300 MHz, CDCl₃) δ: 6.24 (1H, m), 6.98 (1H, dd, J = 8.6, 2.1 Hz), 7.30-7.35 (1H, m), 7.39-7.51 (2H, m), 7.59-7.77 (6H, m), 8.10 (1H, s), 8.23 (1H, dd, J = 7.9, 1.5 Hz), 8.47-8.52 (1H, m). |
| 99 | | ¹H NMR (300 MHz, DMSO-d6) δ: 7.00-7.06 (1H, m), 7.15-7.28 (2H, m), 7.41-7.73 (8H, m), 8.09-8.33 (2H, m), 12.69 (1H, s). |
| 100 | | ¹H NMR (400 MHz, CDCl₃) δ: 1.65-1.74 (1H, m), 1.93-2.04 (3H, m), 2.35-2.39 (1H, m), 2.45 (3H, s), 2.82-2.87 (1H, m), 3.05 (1H, d, J = 13.2 Hz), 3.14-3.17 (1H, m), 5.91 (1H, brs), 7.30-7.40 (3H, m), 7.77 (1H, dd, J = 8.8, 2.8 Hz), 8.30 (1H, s), 8.46 (1H, d, J = 8.0 Hz), 8.68 (1H, brs), 13.15 (1H, s). |
| 101 | | ¹H NMR (400 MHz, DMSO-d6) δ: 1.60-1.72 (2H, m), 2.02-2.13 (2H, m), 2.22 (3H, s), 2.88-2.91 (4H, m), 4.40 (0.5H, s), 5.11 (0.5H, s), 7.27-7.38 (2.5H, m), 7.47-7.64 (2H, m), 7.89 (0.5H, d, J = 6.8 Hz), 8.16 (0.5H, s), 8.29 (1H, m), 8.67 (0.5H, s), 8.89 (0.5H, s), 9.81 (0.5H, s). |

TABLE 1-16-continued

| Example | Structural formula | ¹H NMR, LC-MS |
|---|---|---|
| 102 | | LC-MS(measurement condition C), m/z; 384 (M + H)+ ESI, Rt; 1.45 |
| 103 | | ¹H NMR (400 MHz, DMSO-d6) δ: 2.43 (3H, s), 7.36-7.41 (3H, m), 7.58-7.60 (2H, m), 7.86 (1H, d, J = 7.9 Hz), 7.98 (1H, dd, J = 8.5, 1.8 Hz), 8.30-8.33 (2H, m), 8.50 (1H, brs), 8.60 (1H, brs). |

TABLE 1-17

| Example | Structural formula | ¹H NMR, LC-MS |
|---|---|---|
| 104 | | ¹H NMR (400 MHz, DMSO-d6) δ: 2.09 (3H, s), 7.33-7.40 (3H, m), 7.46-7.55 (2H, m), 7.86-7.88 (1H, m), 7.97 (1H, dd, J = 8.5, 2.4 Hz), 8.30-8.38 (3H, m), 8.61 (1H, d, J = 1.8 Hz). |
| 105 | | ¹H NMR (400 MHz, DMSO-d6) δ: 2.42 (3H, s), 7.31-7.42 (6H, m), 7.53-7.58 (1H, m), 7.63 (1H, dd, J = 8.5, 3.1 Hz), 7.75 (1H, s), 7.90-7.93 (1H, m), 8.24-8.26 (1H, m), 8.64 (1H, d, J = 2.4 Hz). |

TABLE 1-17-continued

| Example | Structural formula | ¹H NMR, LC-MS |
|---|---|---|
| 106 | | LC-MS(measurement condition A), m/z; 347 (M + H)+ ESI, Rt; 0.68 |
| 107 | | ¹H NMR (400 MHz, DMSO-d6) δ: 2.11 (3H, s), 7.32-7.48 (6H, m), 7.54-7.59 (1H, m), 7.65 (1H, dd, J = 8.5, 3.1 Hz), 7.83 (1H, s), 7.89-7.91 (1H, m), 8.26-8.28 (1H, m), 8.62 (1H, d, J = 1.8 Hz). |
| 108 | | ¹H NMR (400 MHz, DMSO-d6) δ: 7.33-7.44 (3H, m), 7.50 (1H, t, J = 9.2 Hz), 7.56-7.67 (4H, m), 7.91 (1H, d, J = 7.9 Hz), 8.25-8.28 (2H, m), 8.64 (1H, brs). |
| 109 | | ¹H NMR (400 MHz, DMSO-d6) δ: 2.13 (3H, s), 7.34-7.48 (6H, m), 7.85 (1H, m), 7.95 (1H, dd, J = 8.5, 1.8 Hz), 8.26 (1H, brs), 8.30-8.32 (2H, m), 8.58 (1H, brs). |
| 110 | | ¹H NMR (400 MHz, DMSO-d6) δ: 7.35-7.53 (4H, m), 7.62-7.70 (2H, m), 7.87 (1H, brs), 7.98 (1H, dd, J = 8.5, 1.8 Hz), 8.30-8.33 (2H, m), 8.60-8.64 (2H, m). |

TABLE 1-18

| Example | Structural formula | ¹H NMR, LC-MS |
|---|---|---|
| 111 | | LC-MS (measurement condition C), m/z; 369 (M + H)+ ESI, Rt; 1.71 |
| 112 | | ¹H NMR (400 MHz, DMSO-d6) δ: 7.45-7.62 (6H, m), 7.96 (1H, brs), 8.00 (1H, dd, J = 8.5, 1.8 Hz), 8.31-8.33 (3H, m), 8.54 (1H, brs). |
| 113 | | ¹H NMR (400 MHz, DMSO-d6) δ: 7.43-7.53 (3H, m), 7.66 (2H, m), 7.99 (1H, m), 8.03 (1H, dd, J = 8.5, 2.4 Hz), 8.32-8.36 (2H, m), 8.54 (1H, br s), 8.79 (1H, brs). |
| 114 | | ¹H NMR (400 MHz, DMSO-d6) δ: 2.12 (3H, s), 7.44-7.48 (5H, m), 7.96 (1H, brs), 8.00 (1H, dd, J = 8.5, 1.8 Hz), 8.32-8.40 (3H, m), 8.53 (1H, br s). |
| 115 | | ¹H NMR (400 MHz, DMSO-d6) δ: 7.20-7.25 (1H, m), 7.36 (1H, dd, J = 8.6, 4.7 Hz), 7.52-7.58 (3H, m), 7.59-7.65 (3H, m), 7.79 (1H, d, J = 7.9 Hz), 7.94 (1H, s), 7.99 (1H, d, J = 8.3 Hz), 8.28 (1H, d, J = 4.5 Hz), 8.72 (1H, s). |

TABLE 1-19

| Example | Structural formula | ¹H NMR |
|---|---|---|
| 116 | | ¹H NMR (400 MHz, DMSO-d6) δ: 3.86 (3H, s), 7.18-7.33 (3H, m), 7.50 (2H, d, J = J = 8.0 Hz), 7.54-7.63 (4H, m), 7.70 (1H, s), 8.11 (1H, d, J = 7.6 Hz), 8.23 (1H, d, J = 4.0 Hz), 8.81 (1H, s). |
| 117 | | ¹H NMR (500 MHz, DMSO-d6) δ: 7.02 (1H, dd, J = 10.5, 8.5 Hz), 7.20 (1H, d, J = 8.3 Hz), 7.51 (2H, d, J = 7.3 Hz), 7.56-7.69 (4H, m), 8.01 (1H, d, J = 11.3 Hz), 8.06 (1H, s), 8.28 (1H, s), 8.56 (1H, s). |
| 118 | | ¹H NMR (400 MHz, DMSO-d6) δ: 7.24-7.29 (1H, m), 7.52-7.54 (2H, m), 7.57-7.66 (5H, m), 7.81 (1H, d, J = 7.6 Hz), 8.15-8.21 (1H, m), 8.27 (1H, d, J = 2.6 Hz), 8.63 (1H, m). |
| 119 | | ¹H NMR (400 MHz, CD₃OD) δ: 2.65 (6H, brs), 3.11 (6H, brs), 7.02-7.18 (2H, m), 7.38-7.62 (3H, m), 7.92 (1H, d, J = 6.8 Hz), 8.26-8.40 (2H, m). |
| 120 | | ¹H NMR (400 MHz, CD₃OD) δ: 2.23 (3H, s), 6.94-6.99 (1H, m), 7.24 (1H, d, J = 8.0 Hz), 7.40-7.55 (5H, m), 7.64-7.69 (1H, m), 8.06-8.08 (1H, m), 8.30 (1H, d, J = 4.0 Hz), 8.66 (1H, s). |

TABLE 1-19-continued

| Example | Structural formula | ¹H NMR |
|---|---|---|
| 121 | | ¹H NMR (400 MHz, CD$_3$OD) δ: 2.22 (3H, s), 7.05-7.12 (2H, m), 7.39-7.55 (5H, m), 8.08 (1H, d, J = 8.0 Hz), 8.13-8.16 (1H, m), 8.31 (1H, d, J = 4.1 Hz), 8.64 (1H, s). |

TABLE 1-20

| Example | Structural formula | ¹H NMR, LC-MS |
|---|---|---|
| 122 | | ¹H NMR (400 MHz, CD$_3$OD) δ: 2.21 (3H, s), 7.25-7.30 (1H, m), 7.41-7.57 (6H, m), 7.91 (1H, d, J = 8.4 Hz), 8.20 (1H, d, J = 8.4 Hz), 8.28 (1H, d, J = 4.4 Hz), 8.79 (1H, d, J = 2.0 Hz). |
| 123 | | ¹H NMR (500 MHz, DMSO-d6) δ: 7.35-7.46 (4H, m), 7.53-7.60 (2H, m), 7.63-7.68 (2H, m), 7.92-7.96 (2H, m), 8.29 (1H, d, J = 4.0 Hz), 8.67 (1H, d, J = 1.5 Hz). |
| 124 | | ¹H NMR (500 MHz, DMSO-d6) δ: 7.34-7.47 (4H, m), 7.53-7.62 (4H, m), 7.65 (1H, dd, J = 8.0, 3.0 Hz), 7.90 (1H, s), 7.95 (1H, d, J = 8.0 Hz), 8.57 (1H, m). |

TABLE 1-20-continued

| Example | Structural formula | ¹H NMR, LC-MS |
|---|---|---|
| 125 | | ¹H NMR (400 MHz, DMSO-d6) δ: 2.21 (1H, s), 2.39 (2H, s), 6.44 (0.4H, s), 6.74 (0.4H, d, J = 6.0 Hz), 6.87 (0.6H, s), 6.92 (0.6H, d, J = 4.8 Hz), 7.28 (0.6H, d, J = 7.2 Hz), 7.39-7.50 (1H, m), 7.59-7.73 (6.4H, m), 8.00 (0.6H, d, J = 5.2 Hz), 8.08 (0.4H, d, J = 5.6 Hz), 8.33 (0.6H, s), 15.10 (0.4H, s). |
| 126 | | ¹H NMR (400 MHz, DMSO-d6) δ: 7.00-7.04 (1H, m), 7.28-7.70 (9H, m), 8.16 (1H, dd, J = 4.8, 0.8 Hz), 13.8 (1H, s). |
| 127 | | LC-MS(measurement condition A), m/z; 351 (M + H)+ ESI, Rt; 1.0 |
| 128 | | ¹H NMR (400 MHz, DMSO-d6) δ: 6.65 (0.2H, m), 7.11 (0.8H, s), 7.34-7.83 (9H, m), 8.19 (0.8H, d, J = 2.4 Hz), 8.31 (0.2H, brs), 8.46 (0.8H, dd, J = 9.2, 4.0 Hz), 13.60 (0.2H, brs). |

TABLE 1-21

| Example | Structure | ¹H NMR, LC-MS |
|---|---|---|
| 129 | 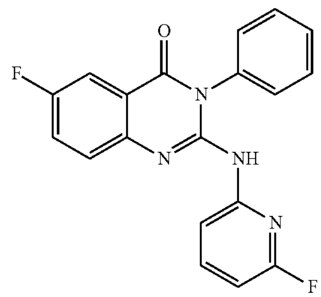 [SMILES: O=c1c2cc(F)ccc2nc(Nc2cncc(F)c2)n1-c1ccccc1] | ¹H NMR (400 MHz, DMSO-d6) δ: 6.81-6.83 (1H, dd, J = 8.4, 2.0 Hz), 7.27 (1H, s), 7.57-7.78 (7H, m), 8.00 (1H, dd, J = 16.4, 8.0 Hz), 8.28 (1H, dd, J = 8.0, 2.0 Hz). |
| 130 | 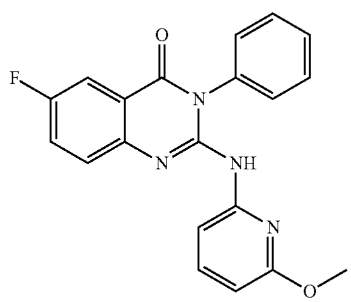 [SMILES: COc1cccc(Nc2nc3ccc(F)cc3c(=O)n2-c2ccccc2)n1] | ¹H NMR (400 MHz, DMSO-d6) δ: 3.63 (3H, s), 6.49 (1H, d, J = 8.0 Hz), 6.75 (1H, s), 7.61-7.77 (8H, m), 8.04 (1H, d, J = 8.0 Hz). |
| 131 | 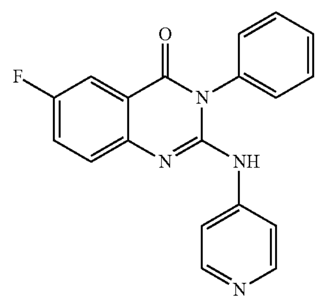 [SMILES: O=c1c2cc(F)ccc2nc(Nc2ccncc2)n1-c1ccccc1] | ¹H NMR (500 MHz, DMSO-d6) δ: 7.45-7.53 (2H, m), 7.54-7.72 (8H, m), 7.91 (1H, br s), 8.37 (2H, brs). |
| 132 | 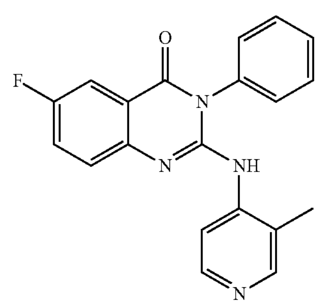 [SMILES: Cc1cnccc1Nc1nc2ccc(F)cc2c(=O)n1-c1ccccc1] | ¹H NMR (500 MHz, DMSO-d6) δ: 1.79 (3H, s), 6.78-6.92 (3H, m), 7.44-7.69 (7H, m), 8.05-8.29 (2H, m). |
| 133 | 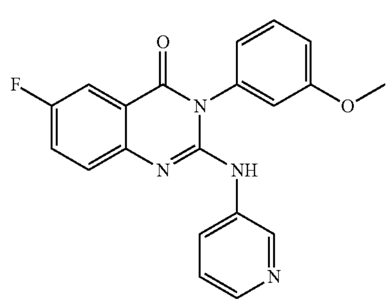 [SMILES: COc1cccc(-n2c(Nc3cccnc3)nc3ccc(F)cc3c2=O)c1] | ¹H NMR (400 MHz, DMSO-d6) δ: 3.82 (3H, s), 7.06-7.07 (1H, m), 7.09-7.16 (2H, m), 7.34-7.41 (2H, m), 7.50-7.60 (2H, m), 7.65 (1H, dd, J = 8.4, 2.8 Hz), 7.81 (1H, s), 7.93-7.95 (1H, m), 8.28 (1H, dd, J = 4.8, 1.6 Hz), 8.67 (1H, d, J = 2.4 Hz). |

TABLE 1-21-continued

| Example | Structure | ¹H NMR, LC-MS |
|---|---|---|
| 134 | 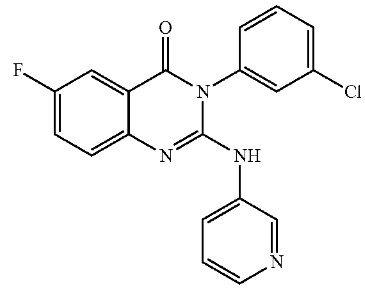 [SMILES: O=c1c2cc(F)ccc2nc(Nc2cccnc2)n1-c1cccc(Cl)c1] | ¹H NMR (400 MHz, DMSO-d6) δ: 7.34-7.41 (2H, m), 7.50-7.67 (5H, m), 7.73 (1H, m), 7.91-7.94 (1H, m), 7.98 (1H, s), 8.29 (1H, dd, J = 4.8, 1.6 Hz), 8.66 (1H, d, J = 2.4 Hz). |
| 135 | 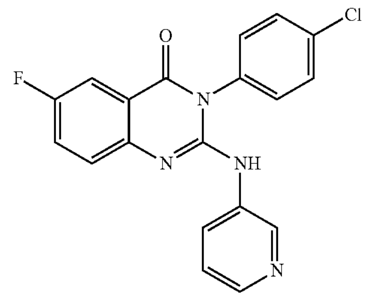 [SMILES: O=c1c2cc(F)ccc2nc(Nc2cccnc2)n1-c1ccc(Cl)cc1] | LC-MS(measurement condition A), m/z; 367 (M + H) + ESI, Rt; 0.72 |

TABLE 1-22

| Example | Structure | ¹H NMR |
|---|---|---|
| 136 | 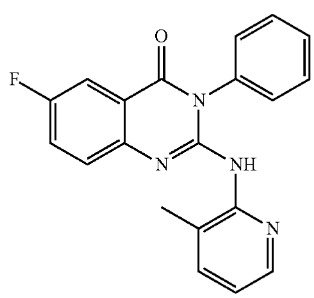 [SMILES: Cc1cccnc1Nc1nc2ccc(F)cc2c(=O)n1-c1ccccc1] | ¹H NMR (400 MHz, DMSO-d6) δ: 1.65 (3H, s), 6.78 (1H, t, J = 2.4 Hz), 7.31 (2H, d, J = 7.6 Hz), 7.38-7.52 (4H, m), 7.62-7.75 (2H, m), 7.67-7.78 (1H, m), 8.04 (1H, d, J = 5.2 Hz), 15.10 (1H, s). |
| 137 | 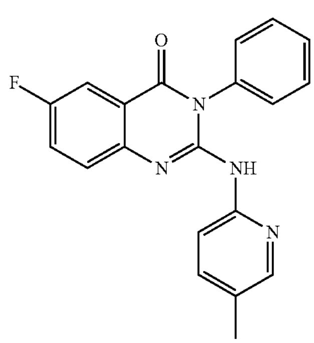 [SMILES: Cc1ccc(Nc2nc3ccc(F)cc3c(=O)n2-c2ccccc2)nc1] | ¹H NMR (400 MHz, DMSO-d6) δ: 4.23 (3H, s), 6.85 (1H, s), 7.55-7.67 (8H, m), 8.00 (1H, s), 8.38 (1H, d, J = 8.0 Hz). |

TABLE 1-22-continued

| Example | Structure | ¹H NMR |
|---|---|---|
| 138 | 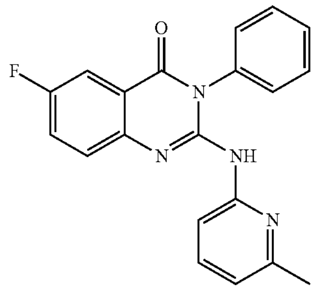 [SMILES: Cc1cccc(Nc2nc3ccc(F)cc3c(=O)n2-c2ccccc2)n1] | ¹H NMR (400 MHz, DMSO-d6) δ: 2.28 (3H, s), 6.83 (1H, s), 6.93 (1H, d, J = 7.6 Hz), 7.60-7.76 (8H, m), 8.32 (1H, d, J = 7.6 Hz). |
| 139 | 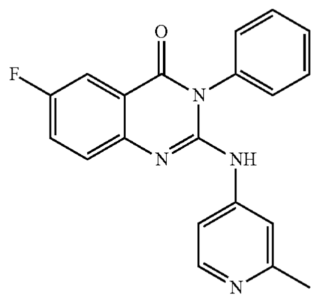 [SMILES: Cc1cc(Nc2nc3ccc(F)cc3c(=O)n2-c2ccccc2)ccn1] | ¹H NMR (400 MHz, DMSO-d6) δ: 2.38 (3H, s), 7.35-7.80 (11H, m), 8.24 (1H, brs). |
| 140 | 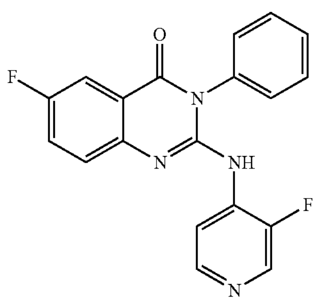 [SMILES: O=c1c2cc(F)ccc2nc(Nc2ccncc2F)n1-c1ccccc1] | ¹H NMR (400 MHz, DMSO-d6) δ: 7.35-7.45 (2H, m), 7.55-7.75 (7H, m), 8.20 (1H, t, J = 6.1 Hz), 8.37 (1H, d, J = 5.1 Hz), 8.45-8.47 (1H, m). |
| 141 | 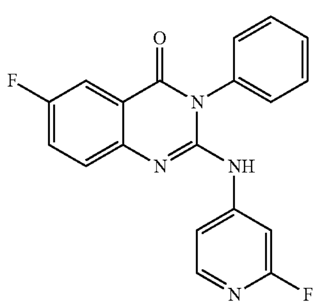 [SMILES: O=c1c2cc(F)ccc2nc(Nc2ccnc(F)c2)n1-c1ccccc1] | ¹H NMR (400 MHz, DMSO-d6) δ: 7.51-7.73 (10H, m), 8.01 (1H, d, J = 5.6 Hz), 8.29 (1H, s). |
| 142 | 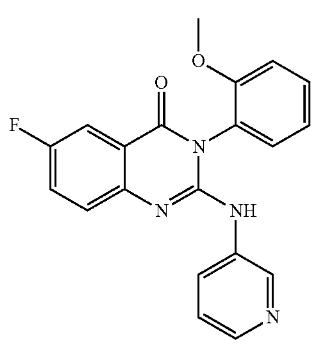 [SMILES: COc1ccccc1-n1c(Nc2cccnc2)nc2ccc(F)cc2c1=O] | ¹H NMR (400 MHz, DMSO-d6) δ: 3.78 (3H, s), 7.17 (1H, t, J = 7.6 Hz), 7.30 (1H, d, J = 8.0 Hz), 7.34-7.47 (3H, m), 7.55-7.65 (3H, m), 7.92 (1H, m), 7.97 (1H, s), 8.28 (1H, dd, J = 4.8, 1.2 Hz), 8.63 (1H, d, J = 2.4 Hz). |

TABLE 1-23
| Example | Structure | ¹H NMR |
|---|---|---|
| 143 | 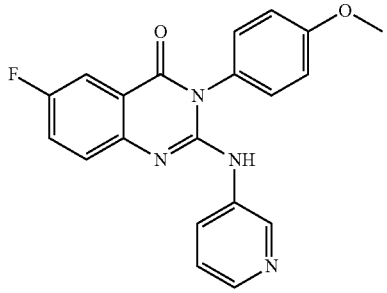 [SMILES: COc1ccc(-n2c(Nc3cccnc3)nc3ccc(F)cc3c2=O)cc1] | ¹H NMR (400 MHz, DMSO-d6) δ: 3.86 (3H, s), 7.15 (2H, d, J = 8.8 Hz), 7.33-7.44 (4H, m), 7.57 (1H, m), 7.64 (1H, dd, J = 8.8, 2.8 Hz), 7.83 (1H, s), 7.92-7.96 (1H, m), 8.27 (1H, dd, J = 4.8, 1.2 Hz), 8.67 (1H, d, J = 2.4 Hz). |
| 144 | 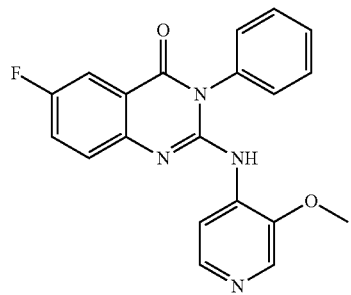 [SMILES: COc1cnccc1Nc1nc2ccc(F)cc2c(=O)n1-c1ccccc1] | ¹H NMR (500 MHz, DMSO-d6) δ: 3.64 (3H, s), 7.05 (1H, s), 7.63 (2H, d, J = 5.6 Hz), 7.68-7.74 (6H, m), 8.19 (1H, s), 8.21 (1H, d, J = 4.0 Hz), 8.68 (1H, d, J = 4.4 Hz). |
| 145 | 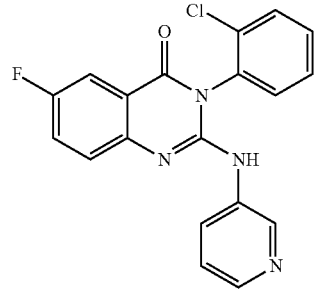 | ¹H NMR (400 MHz, DMSO-d6) δ: 7.34-7.42 (2H, m), 7.58-7.78 (6H, m), 7.88-7.90 (1H, m), 8.13 (1H, s), 8.30 (1H, dd, J = 4.8, 1.2 Hz), 8.63 (1H, d, J = 2.4 Hz). |
| 146 | 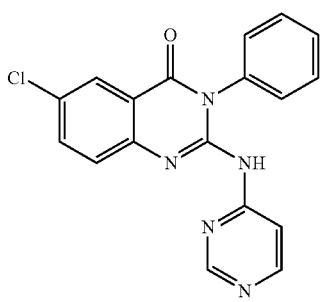 | LC-MS(measurement condition B), m/z; 350 (M + H) + ESI, Rt; 0.88 |
| 147 | 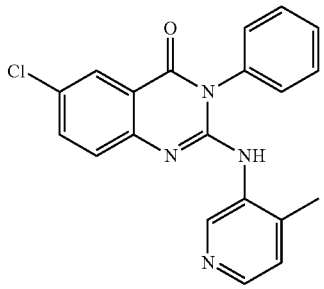 [SMILES: Cc1ccncc1Nc1nc2ccc(Cl)cc2c(=O)n1-c1ccccc1] | ¹H NMR (400 MHz, CDCl₃) δ: 1.95 (3H, s), 5.72 (1H, s), 7.08 (1H, d, J = 4.9 Hz), 7.38 (1H, d, J = 8.6 Hz), 7.42-7.45 (2H, m), 7.55-7.70 (4H, m), 8.12 (1H, d, J = 2.4 Hz), 8.28 (1H, d, J = 4.9 Hz), 9.15 (1H, s). |

TABLE 1-23-continued

| Example | Structure | ¹H NMR |
|---|---|---|
| 148 | 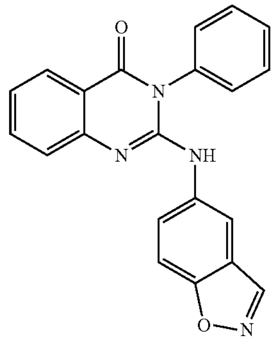 [SMILES: O=c1c2ccccc2nc(Nc2ccc3oncc3c2)n1-c1ccccc1] | ¹H NMR (300 MHz, DMSO-d6) δ: 5.64 (2H, m), 6.83-6.96 (2H, m), 7.13-7.23 (1H, m), 7.38-7.65 (7H, m), 7.75-7.81 (1H, m), 8.11 (1H, dd, J = 8.1, 1.5 Hz). |

TABLE 1-24

| Example | Structure | ¹H NMR, LC-MS |
|---|---|---|
| 149 | 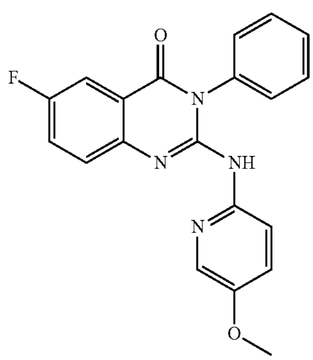 [SMILES: COc1ccc(Nc2nc3ccc(F)cc3c(=O)n2-c2ccccc2)nc1] | ¹H NMR (500 MHz, CDCl₃) δ: 3.86 (3H, s), 6.67 (1H, s), 7.35 (1H, dd, J = 9.0, 3.0 Hz), 7.42-7.46 (3H, m), 7.57 (1H, dd, J = 8.5, 5.0 Hz), 7.64 (1H, d, J = 8.0 Hz), 7.67-7.70 (2H, m), 7.85 (1H, dd, J = 8.3, 2.7 Hz), 7.89 (1H, d, J = 3.0 Hz), 8.55 (1H, d, J = 9.5 Hz). |
| 150 | 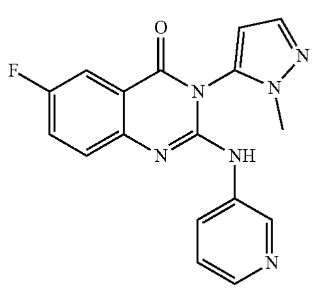 [SMILES: Cn1nccc1-n1c(Nc2cccnc2)nc2ccc(F)cc2c1=O] | ¹H NMR (400 MHz, DMSO-d6) δ: 3.70 (3H, s), 6.52 (1H, d, J = 2.0 Hz), 7.36-7.43 (2H, m), 7.62 (1H, td, J = 8.7, 3.1 Hz), 7.66 (1H, d, J = 2.0 Hz), 7.69 (1H, dd, J = 8.6, 3.0 Hz), 7.97-8.00 (1H, m), 8.29 (1H, dd, J = 4.6, 1.2 Hz), 8.42 (1H, s), 8.72 (1H, d, J = 2.3 Hz). |
| 151 | 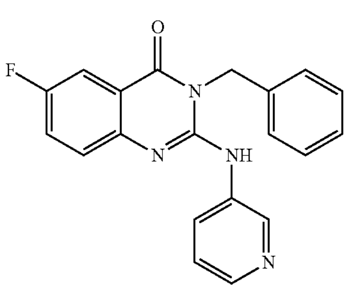 [SMILES: O=c1c2cc(F)ccc2nc(Nc2cccnc2)n1Cc1ccccc1] | ¹H NMR (400 MHz, DMSO-d6) δ: 5.53 (2H, s), 7.23-7.26 (1H, m), 7.31-7.36 (6H, m), 7.50-7.55 (1H, m), 7.65 (1H, dd, J = 8.8, 2.8 Hz), 7.90 (1H, d, J = 7.6 Hz), 8.22 (1H, d, J = 4.0 Hz), 8.60 (1H, s). |

TABLE 1-24-continued

| Example | Structure | ¹H NMR, LC-MS |
| --- | --- | --- |
| 152 | 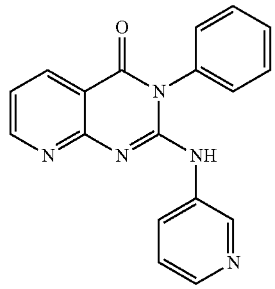 [SMILES: O=c1c2cccnc2nc(Nc2cccnc2)n1-c1ccccc1] | ¹H NMR (400 MHz, DMSO-d6) δ: 7.25 (1H, dd, J = 7.8, 4.6 Hz), 7.38 (1H, dd, J = 7.9, 4.7 Hz), 7.54-7.56 (2H, m), 7.58-7.65 (3H, m), 7.92 (1H, d, J = 7.4 Hz), 8.08 (1H, s), 8.30-8.33 (2H, m), 8.64 (1H, s), 8.74 (1H, d, J = 2.4 Hz). |
| 153 | 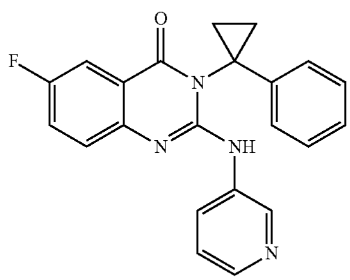 [SMILES: O=c1c2cc(F)ccc2nc(Nc2cccnc2)n1C1(c2ccccc2)CC1] | ¹H NMR (400 MHz, DMSO-d6) δ: 1.62-1.67 (1H, m), 1.76-1.85 (2H, m), 2.05-2.09 (1H, m), 7.05 (2H, d, J = 7.6 Hz), 7.22 (1H, t, J = 7.2 Hz), 7.31-7.35 (3H, m), 7.39 (1H, dd, J = 8.4, 4.8 Hz), 7.51-7.56 (1H, m), 7.64 (1H, dd, J = 8.6, 3.2 Hz), 7.99 (1H, d, J = 8.0 Hz), 8.32-8.33 (2H, m), 8.69 (1H, d, J = 2.4 Hz). |
| 154 | 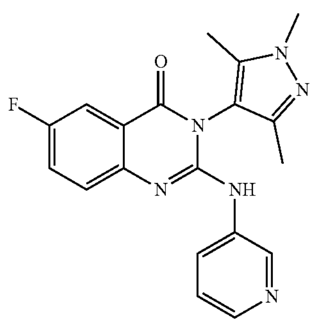 [SMILES: Cc1nn(C)c(C)c1-n1c(Nc2cccnc2)nc2ccc(F)cc2c1=O] | ¹H NMR (400 MHz, DMSO-d6) δ: 1.96 (3H, s), 2.08 (3H, s), 3.75 (3H, s), 7.36-7.40 (2H, m), 7.57 (1H, td, J = 8.7, 3.1 Hz), 7.65 (1H, dd, J = 8.7, 3.0 Hz), 7.98-8.01 (1H, m), 8.28-8.34 (2H, m), 8.71 (1H, d, J = 2.0 Hz). |
| 155 | 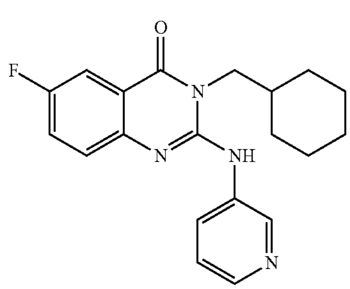 [SMILES: O=c1c2cc(F)ccc2nc(Nc2cccnc2)n1CC1CCCCC1] | LC-MS(measurement condition C), m/z; 353 (M + H) + ESI, Rt; 1.66. |

TABLE 1-25

| Example | Structure | ¹H NMR, LC-MS |
|---|---|---|
| 156 | (structure with HCOOH) | ¹H NMR (400 MHz, DMSO-d6) δ: 1.38 (2H, q, J = 10.8 Hz), 1.61 (2H, d, J = 12.0 Hz), 1.86 (1H, s), 2.01 (2H, s), 2.23 (3H, s), 2.87 (2H, d, J = 10.0 Hz), 4.21 (2H, s), 7.33 (1H, dd, J = 9.0, 5.2 Hz), 7.41 (1H, dd, J = 8.0, 4.8 Hz), 7.49-7.54 (1H, m), 7.65 (1H, dd, J = 8.8, 2.8 Hz), 8.02 (1H, brs), 8.27-8.32 (3H, m), 8.77 (1H, brs), 8.87 (1H, brs). |
| 157 | (structure) | ¹H NMR (400 MHz, DMSO-d6) δ: 5.58 (2H, s), 7.34-7.44 (3H, m), 7.52 (1H, d, J = 7.6 Hz), 7.55-7.60 (1H, m), 7.66 (1H, dd, J = 8.8, 3.2 Hz), 7.83-7.88 (1H, m), 8.06 (1H, d, J = 8.0 Hz), 8.28 (1H, d, J = 3.6 Hz), 8.57 (1H, d, J = 4.4 Hz), 8.75 (1H, d, J = 2.8 Hz), 9.57 (1H, s). |
| 158 | (structure) | LC-MS(measurement condition C), m/z; 361 (M + H) + ESI, Rt; 1.60. |
| 159 | (structure) | ¹H NMR (400 MHz, DMSO-d6) δ: 1.79 (4H, s), 2.73 (4H, m), 2.94 (2H, s), 4.33 (2H, s), 7.37-7.43 (2H, m), 7.51-7.56 (1H, m), 7.66 (1H, dd, J = 8.8, 2.8 Hz), 8.02 (1H, d, J = 8.0 Hz), 8.27 (1H, dd, J = 4.6, 1.2 Hz), 8.65 (1H, s), 11.49 (1H, s). |
| 160 | (structure) | ¹H NMR (400 MHz, DMSO-d6) δ: 7.38-7.40 (2H, m), 7.56-7.60 (1H, m), 7.66 (1H, dd, J = 8.6, 3.0 Hz), 7.96 (1H, d, J = 8.2 Hz), 8.11 (1H, s), 8.30 (1H, d, J = 4.6 Hz), 8.42 (1H, s), 8.70 (1H, d, J = 2.4 Hz), 9.35 (1H, s). |

TABLE 1-25-continued

| Example | Structure | ¹H NMR, LC-MS |
|---|---|---|
| 161 | 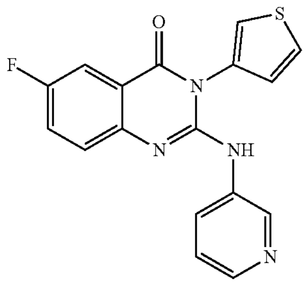 [SMILES: O=c1c2cc(F)ccc2nc(Nc2cccnc2)n1-c1ccsc1] | ¹H NMR (400 MHz, DMSO-d6) δ: 7.22 (1H, dd, J = 5.1, 1.1 Hz), 7.37-7.41 (2H, m), 7.54-7.60 (1H, m), 7.64 (1H, dd, J = 8.7, 3.0 Hz), 7.78 (1H, dd, J = 5.1, 3.2 Hz), 7.88-7.90 (1H, m), 7.96-7.99 (2H, m), 8.35 (1H, brs), 8.74 (1H, brs). |
| 162 | 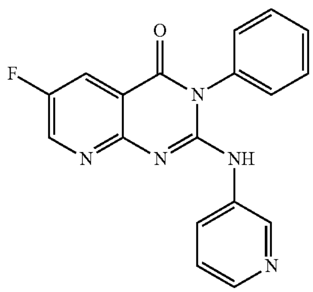 [SMILES: O=c1c2cc(F)cnc2nc(Nc2cccnc2)n1-c1ccccc1] | ¹H NMR (400 MHz, DMSO-d6) δ: 7.38 (1H, dd, J = 8.2, 4.7 Hz), 7.54-7.56 (2H, m), 7.58-7.69 (3H, m), 7.91 (1H, d, J = 8.5 Hz), 8.09 (1H, brs), 8.13 (1H, dd, J = 7.8, 3.2 Hz), 8.32 (1H, d, J = 4.2 Hz), 8.63 (1H, s), 8.78 (1H, d, J = 3.1 Hz). |

TABLE 1-26

| Example | Structure | ¹H NMR |
|---|---|---|
| 163 | 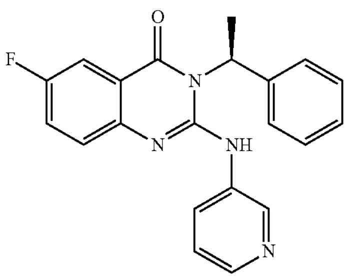 [SMILES: C[C@@H](c1ccccc1)n1c(Nc2cccnc2)nc2ccc(F)cc2c1=O] | ¹H NMR (400 MHz, CDCl₃,) δ: 1.93 (3H, d, J = 7.2 Hz), 6.34 (1H, s), 7.11-7.18 (1H, m), 7.20 (1H, dd, J = 8.2, 4.4 Hz), 7.38-7.44 (2H, m), 7.47-7.55 (5H, m), 7.82 (1H, d, J = 8.4 Hz), 7.90 (1H, dd, J = 8.2, 2.8 Hz), 8.05 (1H, s), 8.25 (1H, d, J = 4.8 Hz). |
| 164 | 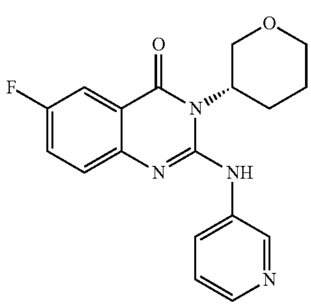 [SMILES: O=c1c2cc(F)ccc2nc(Nc2cccnc2)n1[C@H]1CCCOC1] | ¹H NMR (400 MHz, CD,OD) δ: 1.80-1.93 (2.5H, m), 2.01-2.05 (0.5H, m), 2.75-2.88 (1H, m), 3.41-3.65 (1H, m), 3.86-4.04 (2H, m), 4.48-4.57 (1H, m), 4.74-4.83 (0.5H, m), 5.37-5.46 (0.5H, m), 7.13 (0.5H, dd, J = 9.0, 4.0 Hz), 7.27-7.35 (1H, m), 7.39-7.46 (2H, m), 7.59-7.68 (1H, m), 8.06 (0.5H, d, J = 8.4 Hz), 8.16 (0.5H, s), 8.22-8.28 (1H, m), 8.72 (0.5H, d, J = 2.0 Hz). |
| 165 | 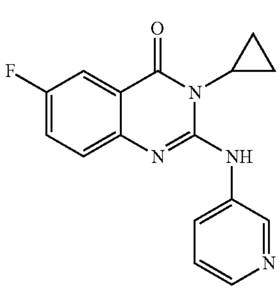 [SMILES: O=c1c2cc(F)ccc2nc(Nc2cccnc2)n1C1CC1] | ¹H NMR (400 MHz, DMSO-d6) δ: 0.87-0.91 (2H, m), 1.30-1.35 (2H, m), 2.94-3.00 (1H, m), 7.34-7.42 (2H, m), 7.48-7.53 (1H, m), 7.63 (1H, dd, J = 8.8, 3.2 Hz), 8.19-8.22 (1H, m), 8.30 (1H, dd, J = 4.4, 1.2 Hz), 8.89-8.91 (2H, m). |

TABLE 1-26-continued

| Example | Structure | ¹H NMR |
|---|---|---|
| 166 | 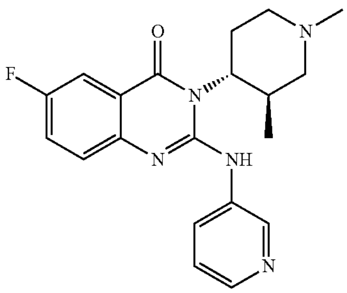 [SMILES: C[C@@H]1CN(C)CC[C@H]1n1c(Nc2cccnc2)nc2ccc(F)cc2c1=O] | ¹H NMR (400 MHz, DMSO-d6) δ: 0.68-0.76 (3H, m), 1.54-1.81 (2H, m), 1.97 (1H, brs), 2.21 (3H, s), 2.82-3.02 (4H, m), 4.03 (0.5H, s), 4.67-4.91 (0.5H, m), 7.28-7.49 (3.5H, m), 7.60-7.65 (1H, m), 7.85 (0.5H, d, J = 7.6 Hz), 8.13 (0.5H, s), 8.25-8.30 (1H, m), 8.63 (0.5H, s), 8.91 (0.5H, s), 9.82 (0.5H, s). |
| 167 | 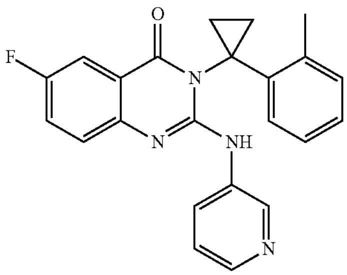 [SMILES: Cc1ccccc1C1(n2c(Nc3cccnc3)nc3ccc(F)cc3c2=O)CC1] | ¹H NMR (400 MHz, CD₃OD) δ: 1.58 (1H, brs), 1.83 (1H, brs), 2.24 (2H, brs), 2.34 (3H, s), 7.09-7.24 (3H, m), 7.34-7.45 (4H, m), 7.73 (1H, dd, J = 8.8, 2.8 Hz), 8.10 (1H, d, J = 8.4 Hz), 8.28 (1H, d, J = 4.0 Hz), 8.70 (1H, d, J = 2.4 Hz). |
| 168 | 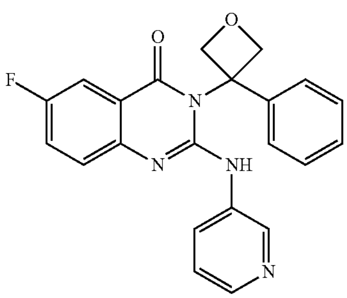 [SMILES: O=c1c2cc(F)ccc2nc(Nc2cccnc2)n1C1(c2ccccc2)COC1] | ¹H NMR (400 MHz, CD₃OD) δ: 4.13 (1H, d, J = 9.6 Hz), 4.39 (1H, d, J = 11.6 Hz), 4.59 (1H, d, J = 9.2 Hz), 4.90 (1H, d, J = 11.2 Hz), 7.23-7.35 (3H, m), 7.38-7.42 (2H, m), 7.47-7.52 (2H, m), 7.58 (1H, dd, J = 9.0, 4.4 Hz), 7.68 (1H, dd, J = 8.6, 2.8 Hz), 8.32 (1H, d, J = 4.8 Hz), 8.42-8.45 (1H, m), 9.21 (1H, d, J = 2.4 Hz). |
| 169 | 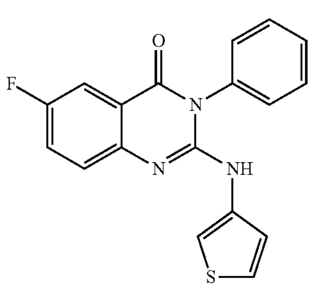 [SMILES: O=c1c2cc(F)ccc2nc(Nc2ccsc2)n1-c1ccccc1] | ¹H NMR (400 MHz, DMSO-d6) δ: 7.06 (1H, dd, J = 5.0, 1.2 Hz), 7.27 (1H, dd, J = 5.2, 3.2 Hz), 7.43-7.46 (2H, m), 7.49 (1H, dd, J = 8.2, 3.0 Hz), 7.54 (1H, dd, J = 9.0, 5.0 Hz), 7.60-7.70 (5H, m). |

TABLE 1-27

| Example | Structure | ¹H NMR, LC-MS |
|---------|-----------|---------------|
| 170 | 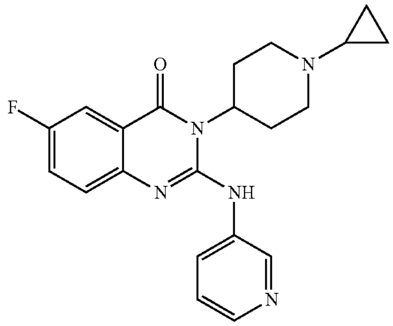 [SMILES: O=c1c2cc(F)ccc2nc(Nc2cccnc2)n1C1CCN(C2CC2)CC1] | LC-MS(measurement condition C), m/z; 380 (M + H) + ESI, Rt; 1.40. |
| 171 | 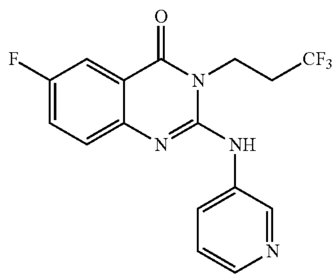 [SMILES: O=c1c2cc(F)ccc2nc(Nc2cccnc2)n1CCC(F)(F)F] | LC-MS(measurement condition C), m/z; 353 (M + H) + ESI, Rt; 1.48. |
| 172 | 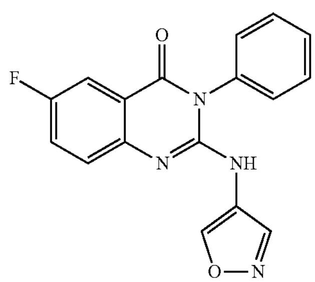 [SMILES: O=c1c2cc(F)ccc2nc(Nc2cnoc2)n1-c1ccccc1] | ¹H NMR (400 MHz, CD₃OD) δ: 7.43-7.45 (2H, m), 7.53 (1H, td, J = 8.6, 2.8 Hz), 7.64-7.73 (5H, m), 8.54 (1H, s), 9.32 (1H, s). |
| 173 | 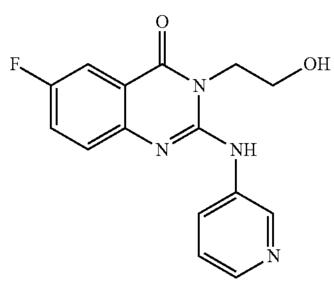 | ¹H NMR (400 MHz, DMSO-d6) δ: 3.81 (2H, t, J = 4.2 Hz), 4.35 (2H, t, J = 4.6 Hz), 5.76 (1H, s), 7.39-7.42 (2H, m), 7.54 (1H, td, J = 8.7, 2.8 Hz), 7.67 (1H, dd, J = 8.4, 2.8 Hz), 8.07 (1H, d, J = 7.6 Hz), 8.28 (1H, s), 8.74 (1H, s), 9.20 (1H, s). |
| 174 | 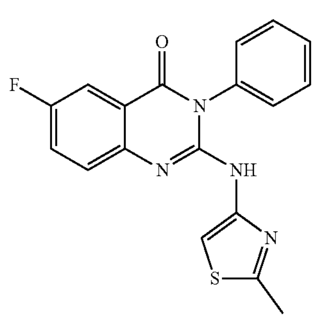 [SMILES: Cc1nc(Nc2nc3ccc(F)cc3c(=O)n2-c2ccccc2)cs1] | ¹H NMR (400 MHz, CD₃OD) δ: 2.56 (3H, s), 7.48 (2H, d, J = 6.8 Hz), 7.52 (1H, d, J = 8.0, 2.8 Hz), 7.70-7.71 (1H, m), 7.73-7.76 (4H, m), 7.84 (1H, s). |

TABLE 1-27-continued

| Example | Structure | ¹H NMR, LC-MS |
|---|---|---|
| 175 | 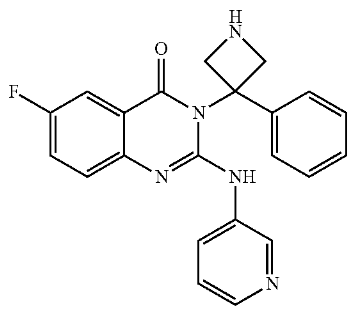 [SMILES: O=c1c2cc(F)ccc2nc(Nc2cccnc2)n1C1(c2ccccc2)CNC1] | LC-MS(measurement condition C), m/z; 388 (M + H) + ESI, Rt; 1.43. |
| 176 | 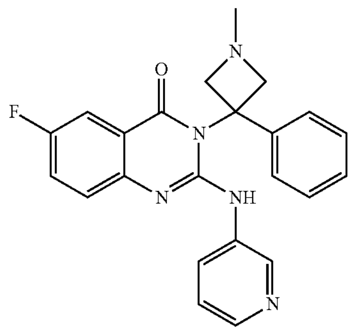 [SMILES: CN1CC(c2ccccc2)(n2c(Nc3cccnc3)nc3ccc(F)cc3c2=O)C1] | ¹H NMR (400 MHz, CD₃OD) δ: 2.47 (3H, s), 3.46-3.51 (1H, m), 4.08-4.11 (2H, m), 4.58 (1H, d, J = 9.2 Hz), 7.30-7.33 (3H, m), 7.37-7.41 (2H, m), 7.47-7.52 (2H, m), 7.58 (1H, dd, J = 9.2, 4.9 Hz), 7.68 (1H, dd, J = 8.6, 3.1 Hz), 8.31 (1H, dd, J = 4.9, 1.2 Hz), 8.40-8.44 (1H, m), 9.18 (1H, d, J = 3.1 Hz). |

TABLE 1-28

| Example | Structure | ¹H NMR, LC-MS |
|---|---|---|
| 177 | 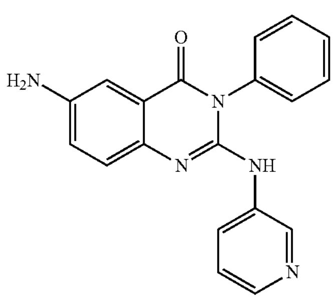 [SMILES: Nc1ccc2nc(Nc3cccnc3)n(-c3ccccc3)c(=O)c2c1] | LC-MS(measurement condition C), m/z; 330 (M + H) + ESI, Rt; 1.35. |
| 178 | 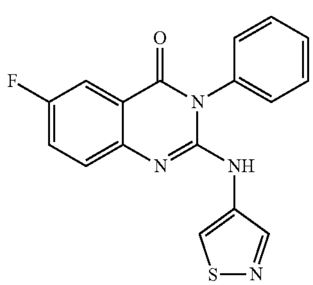 [SMILES: O=c1c2cc(F)ccc2nc(Nc2cnsc2)n1-c1ccccc1] | ¹H NMR (400 MHz, DMSO-d6) δ: 7.47-7.54 (2H, m), 7.55-7.65 (6H, m), 8.29 (1H, s), 8.74 (1H, s), 9.13 (1H, s). |

TABLE 1-28-continued

| Example | Structure | ¹H NMR, LC-MS |
|---|---|---|
| 179 | 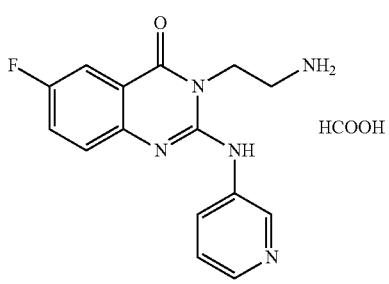 [SMILES: NCCn1c(Nc2cccnc2)nc2ccc(F)cc2c1=O ; "HCOOH"] | ¹H NMR (400 MHz, DMSO-d6) δ: 3.07 (2H, t, J = 4.4 Hz), 4.30 (2H, t, J = 5.0 Hz), 7.37-7.41 (2H, m), 7.54 (1H, td, J = 8.7, 2.8 Hz), 7.66 (1H, dd, J = 8.6, 2.8 Hz), 8.06 (1H, d, J = 8.4 Hz), 8.25 (1H, d, J = 4.0 Hz), 8.28 (1H, s), 8.75 (1H, d, J = 2.4 Hz). |
| 180 | 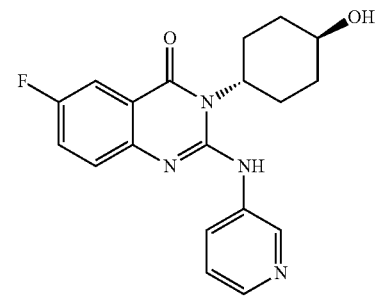 [SMILES: O=c1c2cc(F)ccc2nc(Nc2cccnc2)n1[C@H]1CC[C@H](O)CC1] | ¹H NMR (400 MHz, CD₃OD) δ: 1.29-1.57 (2H, m), 1.75-1.87 (2H, m), 2.03-2.06 (2H, m), 2.72-2.91 (2H, m), 3.59-3.73 (1H, m), 4.44-4.50 (0.6H, m), 5.17-5.25 (0.4H, m), 7.12 (0.4H, dd, J = 9.0, 4.2 Hz), 7.25-7.32 (1H, m), 7.37-7.46 (2H, m), 7.60 (0.4H, dd, J = 8.4, 2.4 Hz), 7.65 (0.6H, dd, J = 8.6, 2.8 Hz), 7.99 (0.6H, d, J = 8.0 Hz), 8.15 (0.4H, s), 8.22 (0.4H, s), 8.28 (0.6H, d, J = 4.0 Hz), 8.67 (0.6H, s). |
| 181 | 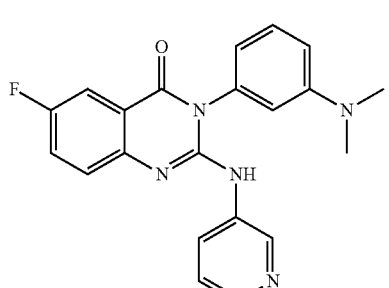 | ¹H NMR (400 MHz, DMSO-d6) δ: 2.95 (6H, s), 6.72 (1H, d, J = 7.6 Hz), 6.84 (1H, t, J = 2.0 Hz), 6.89 (1H, dd, J = 8.6, 2.8 Hz), 7.32-7.41 (3H, m), 7.58 (1H, td, J = 8.7, 2.8 Hz), 7.64 (1H, dd, J = 8.8, 3.2 Hz), 7.68 (1H, s), 7.94-7.97 (1H, m), 8.27 (1H, dd, J = 4.6, 0.8 Hz), 8.66 (1H, d, J = 2.4 Hz). |
| 182 | 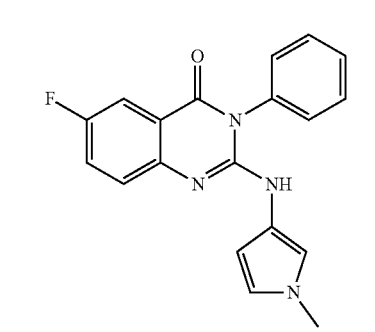 [SMILES: Cn1ccc(Nc2nc3ccc(F)cc3c(=O)n2-c2ccccc2)c1] | ¹H NMR (400 MHz, DMSO-d6) δ: 3.58 (3H, s), 6.01 (1H, s), 6.07 (1H, s), 6.50 (1H, s), 7.24 (1H, s), 7.42 (2H, d, J = 7.2 Hz), 7.46-7.49 (1H, m), 7.53-7.63 (5H, m). |
| 183 | 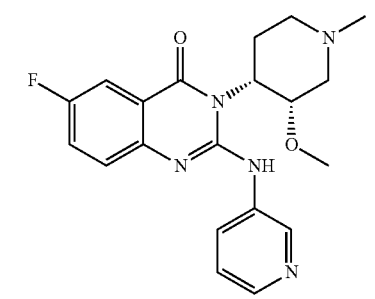 [SMILES: CO[C@H]1CN(C)CC[C@H]1n1c(Nc2cccnc2)nc2ccc(F)cc2c1=O] | ¹H NMR (400 MHz, DMSO-d6) δ: 1.58 (1H, d, J = 9.6 Hz), 2.07-2.15 (2H, m) 2.24 (3H, 2), 2.63-2.71 (1H, m), 2.91 (1H, d, J = 11.2 Hz), 3.29 (1H, d, J = 12.8 Hz), 3.54 (3H, s), 3.83 (1H, s), 5.29 (1H, dt, J = 12.8, 3.0 Hz), 7.39-7.45 (2H, m), 7.58 (1H, td, J = 8.6, 2.8 Hz), 7.68 (1H, dd, J = 8.8, 3.2 Hz), 8.08 (1H, dt, J = 8.4, 1.8 Hz), 8.27 (1H, dd, J = 4.4, 0.8 Hz), 8.71 (1H, d, J = 2.4 Hz), 10.03 (1H, s). |

TABLE 1-29

| Example | Structure | ¹H NMR |
|---|---|---|
| 184 | 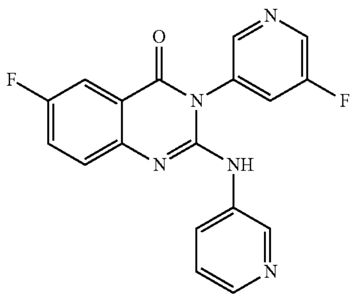 [SMILES: O=c1c2cc(F)ccc2nc(Nc2cccnc2)n1-c1cncc(F)c1] | ¹H NMR (400 MHz, DMSO-d6) δ: 7.36-7.43 (2H, m), 7.59 (1H, td, J = 8.7, 2.8 Hz), 7.67 (1H, dd, J = 8.4, 2.8 Hz), 7.93 (1H, d, J = 8.4 Hz), 8.15 (2H, d, J = 10.4 Hz), 8.30 (1H, s), 8.67 (2H, s), 8.82 (1H, d, J = 2.8 Hz). |
| 185 | 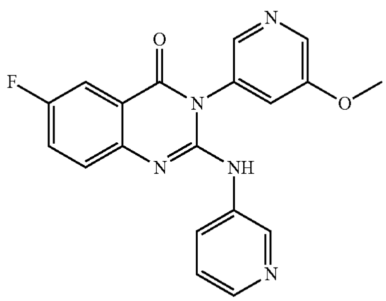 [SMILES: COc1cncc(-n2c(Nc3cccnc3)nc3ccc(F)cc3c2=O)c1] | ¹H NMR (400 MHz, DMSO-d6) δ: 3.88 (3H, s), 7.35-7.42 (2H, m), 7.60 (1H, td, J = 8.7, 2.8 Hz), 7.66 (1H, dd, J = 8.6, 3.2 Hz), 7.72 (1H, t, J = 2.2 Hz), 7.94 (1H, d, J = 8.0 Hz), 8.08 (1H, s), 8.29 (1H, d, J = 4.0 Hz), 8.33 (1H, d, J = 1.6 Hz), 8.49 (1H, d, J = 2.6 Hz), 8.68 (1H, s). |
| 186 | 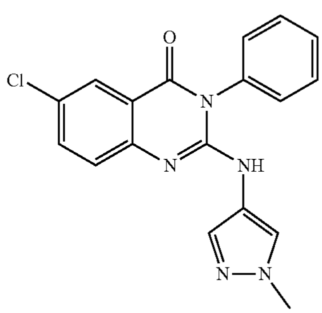 [SMILES: Cn1cc(Nc2nc3ccc(Cl)cc3c(=O)n2-c2ccccc2)cn1] | ¹H NMR (400 MHz, DMSO-d6) δ: 3.79 (3H, s), 7.41-7.43 (2H, m), 7.48-7.52 (2H, m), 7.54-7.62 (3H, m), 7.68 (1H, dd, J = 8.5, 2.4 Hz), 7.80-7.84 (2H, m), 8.11 (1H, s). |
| 187 | 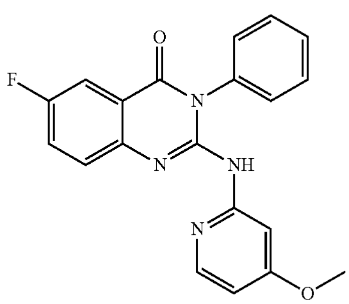 [SMILES: COc1ccnc(Nc2nc3ccc(F)cc3c(=O)n2-c2ccccc2)c1] | ¹H NMR (400 MHz, CDCl₃) δ: 3.94 (3H, s), 6.54 (1H, s), 6.79 (1H, s), 7.40 (2H, d, J = 5.6 Hz), 7.43-7.47 (1H, m), 7.55-7.57 (1H, m), 7.61-7.66 (3H, m), 7.84 (1H, dd, J = 6.8, 2.4 Hz), 7.97 (1H, d, J = 4.4 Hz), 8.33 (1H, s). |
| 188 | 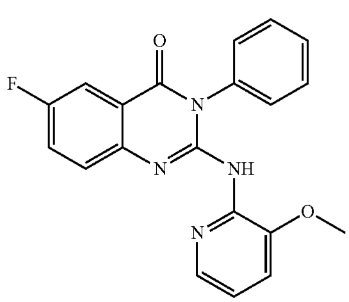 [SMILES: COc1cccnc1Nc1nc2ccc(F)cc2c(=O)n1-c1ccccc1] | ¹H NMR (400 MHz, DMSO-d6) δ: 3.55 (3H, s), 6.08 (1H, s), 6.99 (1H, dd, J = 7.9, 5.1 Hz), 7.27 (1H, dd, J = 8.0, 1.3 Hz), 7.33-7.39 (2H, m), 7.42-7.46 (1H, m), 7.49-7.53 (2H, m), 7.55 (1H, dd, J = 8.9, 4.9 Hz), 7.60 (1H, dd, J = 8.5, 3.0 Hz), 7.67 (1H, dd, J = 8.7, 2.9 Hz), 7.88 (1H, dd, J = 5.1, 1.4 Hz). |

TABLE 1-29-continued
| Example | Structure | ¹H NMR |
|---|---|---|
| 189 | 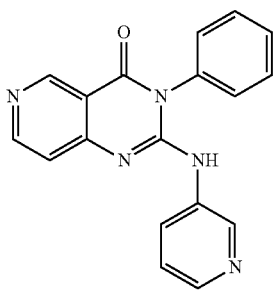 [SMILES: O=c1c2cnccc2nc(Nc2cccnc2)n1-c1ccccc1] | ¹H NMR (400 MHz, DMSO-d6) δ: 7.17 (1H, d, J = 5.6 Hz), 7.38 (1H, dd, J = 8.1, 4.7 Hz), 7.54-7.56 (2H, m), 7.61-7.63 (3H, m), 7.86-7.87 (1H, m), 8.24 (1H, s), 8.33 (1H, d, J = 4.1 Hz), 8.57 (1H, d, J = 5.8 Hz), 8.59 (1H, s), 9.03 (1H, s). |
| 190 | 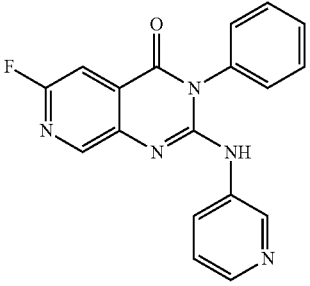 [SMILES: O=c1c2cc(F)ncc2nc(Nc2cccnc2)n1-c1ccccc1] | ¹H NMR (400 MHz, DMSO-d6) δ: 7.43 (1H, brs), 7.53-7.56 (4H, m), 7.59-7.66 (4H, m), 7.92 (1H, d, J = 7.9 Hz), 8.02 (1H, s), 8.41 (1H, s). |
TABLE 1-30
| Example | Structure | ¹H NMR |
|---|---|---|
| 191 | 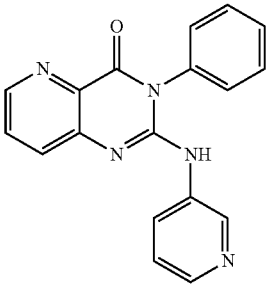 [SMILES: O=c1c2ncccc2nc(Nc2cccnc2)n1-c1ccccc1] | ¹H NMR (400 MHz, DMSO-d6) δ: 7.35 (1H, dd, J = 8.3, 4.7 Hz), 7.54 (2H, d, J = 7.1 Hz), 7.57-7.68 (4H, m), 7.73 (1H, d, J = 8.3 Hz), 7.90-7.94 (2H, m), 8.29 (1H, d, J = 4.2 Hz), 8.52 (1H, d, J = 3.2 Hz), 8.64 (1H, m). |
| 192 | 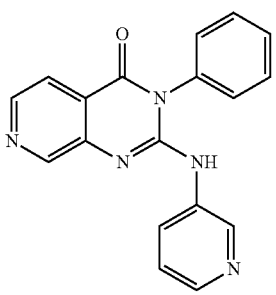 [SMILES: O=c1c2ccncc2nc(Nc2cccnc2)n1-c1ccccc1] | ¹H NMR (400 MHz, DMSO-d6) δ: 7.37 (1H, dd, J = 8.2, 4.7 Hz), 7.52-7.57 (2H, m), 7.57-7.66 (3H, m), 7.80 (1H, d, J = 5.1 Hz), 7.91-7.94 (1H, m), 8.03 (1H, s), 8.31 (1H, dd, J = 3.6, 1.0 Hz), 8.40 (1H, d, J = 5.1 Hz), 8.65 (1H, d, J = 2.4 Hz), 8.71 (1H, s). |

TABLE 1-30-continued

| Example | Structure | ¹H NMR |
|---|---|---|
| 193 | 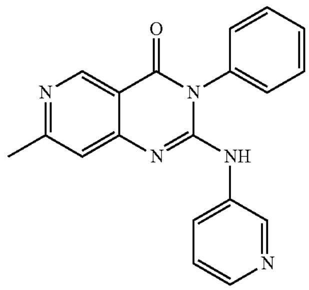 [SMILES: Cc1cc2nc(Nc3cccnc3)n(-c3ccccc3)c(=O)c2cn1] | ¹H NMR (400 MHz, CD₃OD) δ: 2.59 (3H, s), 7.17 (1H, s), 7.45 (1H, dd, J = 8.2, 4.8 Hz), 7.53 (2H, d, J = 7.1 Hz), 7.63-7.73 (3H, m), 8.04 (1H, d, J = 8.0 Hz), 8.35 (1H, d, J = 4.4 Hz), 8.65 (1H, s), 9.03 (1H, s). |
| 194 | 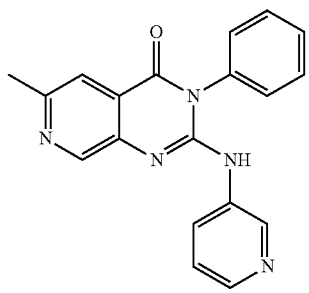 [SMILES: Cc1cc2c(=O)n(-c3ccccc3)c(Nc3cccnc3)nc2cn1] | ¹H NMR (400 MHz, CD₃OD) δ: 2.62 (3H, s), 7.45 (1H, dd, J = 8.3, 4.8 Hz), 7.51-7.53 (2H, m), 7.65-7.72 (3H, m), 7.81 (1H, s), 8.09-8.12 (1H, m), 8.31 (1H, dd, J = 4.8, 1.3 Hz), 8.66 (1H, d, J = 2.3 Hz), 8.67 (1H, s). |
| 195 | 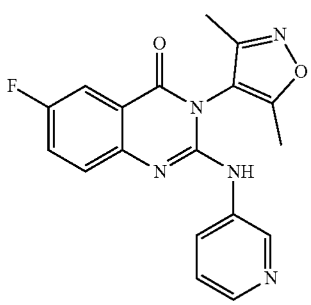 [SMILES: Cc1noc(C)c1-n1c(Nc2cccnc2)nc2ccc(F)cc2c1=O] | ¹H NMR (400 MHz, DMSO-d6) δ: 2.11 (3H, s), 2.35 (3H, s), 7.36-7.43 (2H, m), 7.59 (1H, dt, J = 8.7, 4.4 Hz), 7.68 (1H, dd, J = 8.6, 3.0 Hz), 8.00 (1H, d, J = 8.3 Hz), 8.31 (1H, d, J = 3.6 Hz), 8.66 (1H, s), 8.74 (1H, d, J = 2.2 Hz). |
| 196 | 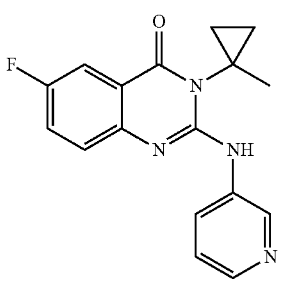 [SMILES: CC1(n2c(Nc3cccnc3)nc3ccc(F)cc3c2=O)CC1] | ¹H NMR (400 MHz, DMSO-d6) δ: 1.00-1.08 (1H, m), 1.15-1.21 (2H, m), 1.31-1.36 (1H, m), 1.57 (3H, s), 7.27 (1H, dd, J = 8.8, 4.8 Hz), 7.42-7.51 (2H, m), 7.62 (1H, dd, J = 8.6, 2.8 Hz), 8.12 (1H, d, J = 8.0 Hz), 8.35 (1H, d, J = 4.4 Hz), 8.43 (1H, s), 8.84 (1H, d, J = 2.0 Hz). |
| 197 | 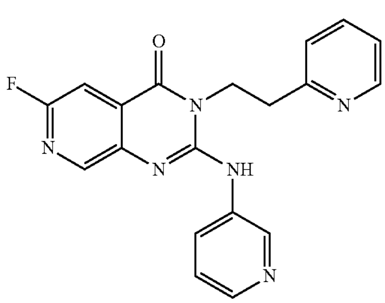 [SMILES: O=c1c2cc(F)ncc2nc(Nc2cccnc2)n1CCc1ccccn1] | ¹H NMR (400 MHz, CDCl₃) δ: 3.52 (2H, t, J = 5.8 Hz), 4.71 (2H, t, J = 5.6 Hz), 7.28-7.30 (1H, m), 7.32-7.37 (2H, m), 7.41 (1H, dd, J = 9.2, 4.8 Hz), 7.72 (1H, td, J = 7.6, 2.8 Hz), 7.81 (1H, dd, J = 8.6, 3.2 Hz), 8.30-8.36 (2H, m), 8.69 (1H, dd, J = 5.2, 1.6 Hz), 8.89 (1H, s), 10.72 (1H, s). |

TABLE 1-31

| Example | Structure | ¹H NMR, LC-MS |
|---|---|---|
| 198 | 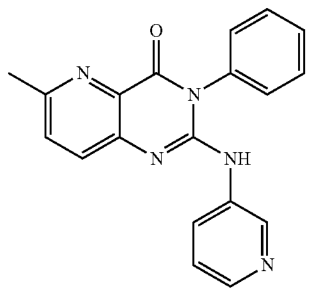 [SMILES: Cc1ccc2nc(Nc3cccnc3)n(-c3ccccc3)c(=O)c2n1] | ¹H NMR (400 MHz, CD₃OD) δ: 2.64 (3H, s), 7.41-7.46 (1H, m), 7.54 (2H, d, J = 7.0 Hz), 7.60 (1H, d, J = 8.6 Hz), 7.64-7.71 (3H, m), 7.77 (1H, d, J = 8.5 Hz), 8.08 (1H, d, J = 9.4 Hz), 8.31 (1H, s), 8.68 (1H, s). |
| 199 | 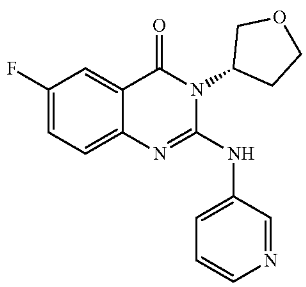 [SMILES: O=c1c2cc(F)ccc2nc(Nc2cccnc2)n1[C@H]1CCOC1] | ¹H NMR (400 MHz, CDCl₃) δ: 2.21-2.30 (1H, m), 2.62-2.70 (1H, m), 3.73-3.80 (1H, m), 3.98 (1H, dd, J = 11.8, 8.0 Hz), 4.31 (1H, d, J = 11.6 Hz), 4.56 (1H, t, J = 9.4 Hz), 6.55-6.60 (1H, m), 7.31-7.35 (1H, m), 7.38 (1H, dd, J = 8.2, 2.8 Hz), 7.43 (1H, dd, J = 9.2, 4.8 Hz), 7.79 (1H, dd, J = 8.8, 2.8 Hz), 8.32-8.35 (2H, m), 8.87 (1H, brs), 9.00 (1H, s). |
| 200 | 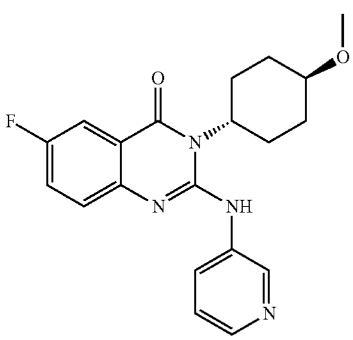 [SMILES: CO[C@H]1CC[C@H](n2c(Nc3cccnc3)nc3ccc(F)cc3c2=O)CC1] | ¹H NMR (400 MHz, CD₃OD) δ: 1.29-1.48 (2H, m), 1.84 (2H, dd, J = 33.2, 10.4 Hz), 2.17-2.23 (2H, m), 2.70-2.90 (2H, m), 3.36-3.39 (4H, m), 4.44-4.50 (0.6H, m), 5.23 (0.4H, t, J = 12.0 Hz), 7.12 (0.4H, dd, J = 9.2, 4.4 Hz), 7.27-7.32 (1H, m), 7.37-7.46 (2H, m), 7.60 (0.4H, dd, J = 9.0, 2.0 Hz), 7.66 (0.6H, dd, J = 8.6, 2.4 Hz), 7.99 (0.6H, d, J = 8.0 Hz), 8.15 (0.4H, s), 8.22-8.28 (1H, m), 8.67 (0.6H, s). |
| 201 | 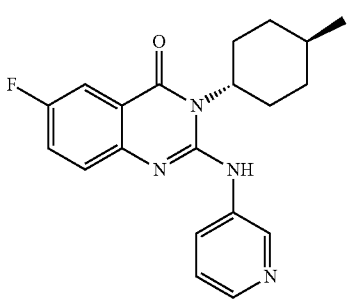 [SMILES: C[C@H]1CC[C@H](n2c(Nc3cccnc3)nc3ccc(F)cc3c2=O)CC1] | LC-MS(measurement condition C), m/z; 353 (M + H) + ESI, Rt; 1.69. |
| 202 | 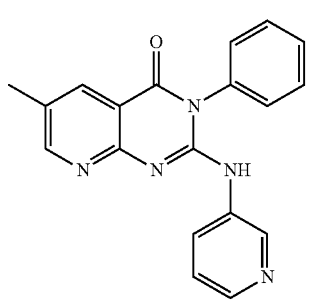 [SMILES: Cc1cnc2nc(Nc3cccnc3)n(-c3ccccc3)c(=O)c2c1] | ¹H NMR (400 MHz, CD₃OD) δ: 2.45 (3H, s), 7.44 (1H, dd, J = 8.3, 4.8 Hz), 7.52-7.54 (2H, m), 7.64-7.71 (3H, m), 8.23 (1H, d, J = 8.1 Hz), 8.30-8.31 (2H, m), 8.59-8.62 (2H, m). |

TABLE 1-31-continued

| Example | Structure | ¹H NMR, LC-MS |
|---|---|---|
| 203 | 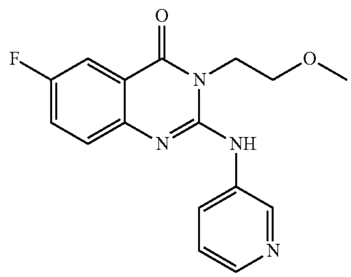 [SMILES: COCCn1c(Nc2cccnc2)nc2ccc(F)cc2c1=O] | ¹H NMR (400 MHz, DMSO-d6) δ: 3.35 (3H, s), 3.70 (2H, t, J = 5.4 Hz), 4.45 (2H, t, J = 5.2 Hz), 7.35-7.42 (2H, m), 7.54 (1H, td, J = 8.8, 2.8 Hz), 7.66 (1H, dd, J = 8.8, 2.8 Hz), 8.00-8.01 (1H, m), 8.29 (1H, dd, J = 4.8, 1.2 Hz), 8.47 (1H, brs), 8.70 (1H, s). |
| 204 | 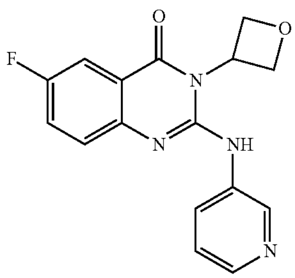 [SMILES: O=c1c2cc(F)ccc2nc(Nc2cccnc2)n1C1COC1] | ¹H NMR (400 MHz, DMSO-d6) δ: 3.67 (1H, dd, J = 11.8, 2.4 Hz), 4.03 (1H, dd, J = 11.6, 3.6 Hz), 4.09 (1H, dd, J = 9.2, 3.6 Hz), 4.31 (1H, t, J = 9.6 Hz), 4.78-4.82 (1H, m), 5.16 (0.5H, s), 6.06 (0.5H, s), 7.48 (1H, dd, J = 8.4, 4.4 Hz), 7.52-7.61 (2H, m), 7.71 (1H, dd, J = 8.8, 2.8 Hz), 8.34 (1H, dd, J = 4.6, 1.2 Hz), 8.41-8.44 (1H, m), 9.16 (1H, d, J = 2.8 Hz). |

TABLE 1-32

| Example | Structure | ¹H NMR, LC-MS |
|---|---|---|
| 205 | 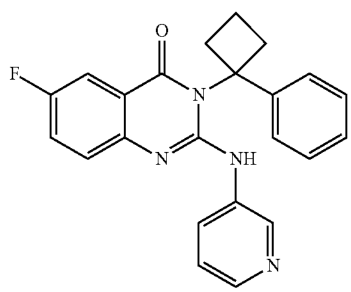 [SMILES: O=c1c2cc(F)ccc2nc(Nc2cccnc2)n1C1(c2ccccc2)CCC1] | LC-MS(measurement condition C), m/z; 387 (M + H) + ESI, Rt; 1.62. |
| 206 | 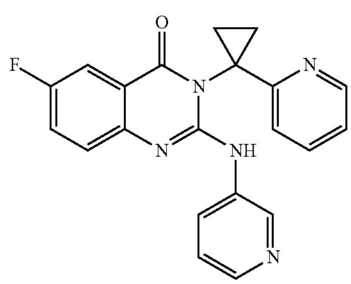 [SMILES: O=c1c2cc(F)ccc2nc(Nc2cccnc2)n1C1(c2ccccn2)CC1] | ¹H NMR (400 MHz, DMSO-d6) δ: 1.52-1.57 (1H, m), 1.73-1.78 (1H, m), 2.00-2.10 (2H, m), 7.27-7.41 (4H, m), 7.54 (1H, td, J = 8.7, 2.8 Hz), 7.62 (1H, dd, J = 8.8, 2.8 Hz), 7.75 (1H, td, J = 7.8, 2.8 Hz), 8.04-8.07 (1H, m), 8.31 (1H, dd, J = 4.8, 1.2 Hz), 8.56 (1H, d, J = 4.8 Hz), 8.76 (1H, d, J = 2.0 Hz), 8.95 (1H, s). |
| 207 | 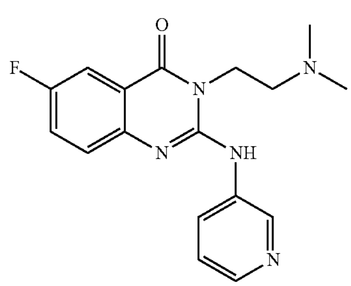 [SMILES: CN(C)CCn1c(Nc2cccnc2)nc2ccc(F)cc2c1=O] | ¹H NMR (400 MHz, DMSO-d6) δ: 2.41 (6H, s), 2.77-2.79 (2H, m), 4.30-4.32 (2H, m), 7.39-7.44 (2H, m), 7.53-7.58 (1H, m), 7.67 (1H, dd, J = 8.8, 2.8 Hz), 8.09 (1H, d, J = 8.4 Hz), 8.26 (1H, d, J = 4.0 Hz), 8.70 (1H, s), 11.91 (1H, s). |

TABLE 1-32-continued

| Example | Structure | ¹H NMR, LC-MS |
|---|---|---|
| 208 | 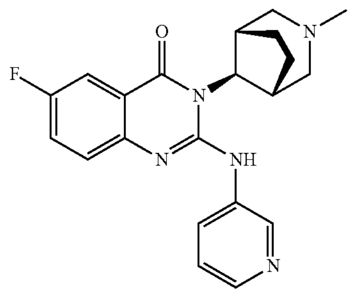 | ¹H NMR (400 MHz, CD₃OD) δ: 1.60 (2H, s), 1.80 (2H, d, J = 4.8 Hz), 2.27 (3H, s), 2.43 (2H, d, J = 10.8 Hz), 2.85 (2H, d, J = 8.0 Hz), 3.21 (2H, brs), 4.52 (1H, s), 7.36 (2H, brs), 7.43 (1H, t, J = 6.4 Hz), 7.62 (1H, d, J = 8.0 Hz), 8.13 (1H, s), 8.24 (1H, s), 8.74 (1H, s). |
| 209 | 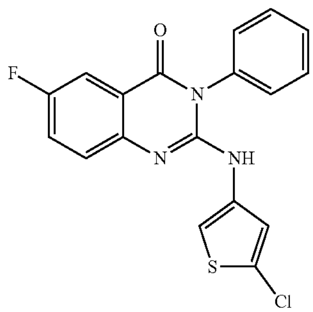 [SMILES: O=c1c2cc(F)ccc2nc(Nc2csc(Cl)c2)n1-c1ccccc1] | ¹H NMR (400 MHz, DMSO-d6) δ: 7.28 (1H, d, J = 1.6 Hz), 7.44-7.46 (2H, m), 7.54-7.65 (6H, m), 7.67 (1H, d, J = 2.0 Hz), 7.93 (1H, s). |
| 210 | 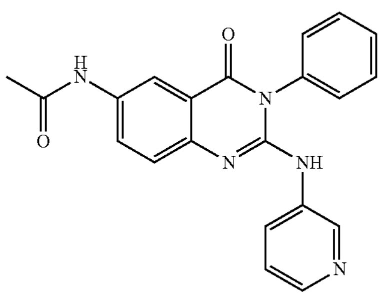 [SMILES: CC(=O)Nc1ccc2nc(Nc3cccnc3)n(-c3ccccc3)c(=O)c2c1] | ¹H NMR (400 MHz, DMSO-d6) δ: 2.06 (3H, s), 7.29-7.34 (2H, m), 7.49-7.51 (2H, m), 7.54-7.64 (4H, m), 7.88 (1H, dd, J = 8.8, 2.0 Hz), 7.92-7.95 (1H, m), 8.24-8.26 (2H, m), 8.65 (1H, d, J = 2.4 Hz), 10.11 (1H, s). |
| 211 | 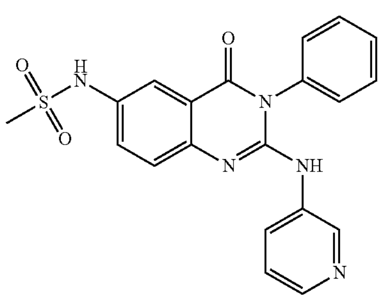 [SMILES: CS(=O)(=O)Nc1ccc2nc(Nc3cccnc3)n(-c3ccccc3)c(=O)c2c1] | LC-MS(measurement condition C), m/z; 408 (M + H) + ESI, Rt; 1.42. |

TABLE 1-33

| Example | Structure | ¹H NMR, LC-MS |
|---|---|---|
| 212 | 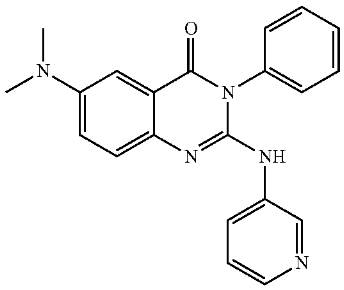 [SMILES: CN(C)c1ccc2nc(Nc3cccnc3)n(-c3ccccc3)c(=O)c2c1] | ¹H NMR (400 MHz, DMSO-d6) δ: 2.94 (6H, s), 7.14 (1H, s), 7.29-7.32 (3H, m), 7.43-7.47 (3H, m), 7.53-7.62 (3H, m), 7.93 (1H, dt, J = 8.4, 1.8 Hz), 8.21 (1H, d, J = 4.0 Hz), 8.65 (1H, d, J = 1.6 Hz). |
| 213 | 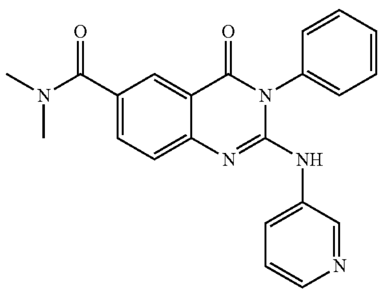 [SMILES: CN(C)C(=O)c1ccc2nc(Nc3cccnc3)n(-c3ccccc3)c(=O)c2c1] | ¹H NMR (400 MHz, DMSO-d6) δ: 2.98 (6H, s), 7.34 (1H, d, J = 8.8 Hz), 7.40 (1H, brs), 7.51 (1H, s), 7.53 (1H, s), 7.57-7.64 (3H, m), 7.70 (1H, dd, J = 8.4, 1.6 Hz), 7.91-7.94 (2H, m), 7.97 (1H, d, J = 2.4 Hz), 8.34 (1H, brs), 8.68 (1H, brs). |
| 214 | 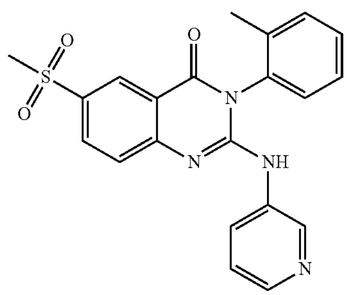 [SMILES: Cc1ccccc1-n1c(Nc2cccnc2)nc2ccc(S(C)(=O)=O)cc2c1=O] | LC-MS(measurement condition C), m/z; 407 (M + H) + ESI, Rt; 1.32. |
| 215 | 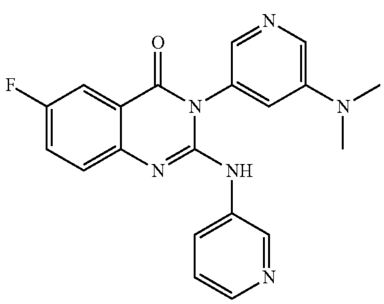 | ¹H NMR (400 MHz, DMSO-d6) δ: 2.99 (6H, s), 7.31 (1H, t, J = 2.4 Hz), 7.34-7.41 (2H, m), 7.58 (1H, dt, J = 8.8, 2.8 Hz), 7.65 (1H, dd, J = 8.6, 3.2 Hz), 7.93-7.96 (2H, m), 8.02 (1H, s), 8.25 (1H, d, J = 2.4 Hz), 8.28 (1H, d, J = 4.4 Hz), 8.68 (1H, d, J = 2.0 Hz). |
| 216 | 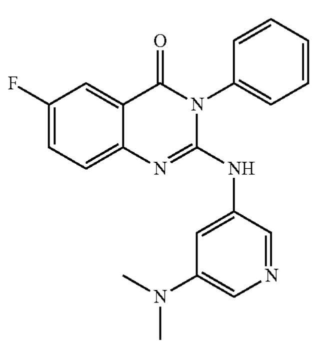 [SMILES: CN(C)c1cncc(Nc2nc3ccc(F)cc3c(=O)n2-c2ccccc2)c1] | ¹H NMR (400 MHz, DMSO-d6) δ: 2.92 (6H, s), 7.35 (1H, s), 7.40 (1H, dd, J = 9.0, 4.8 Hz), 7.50-7.66 (8H, m), 7.83 (1H, s), 8.02 (1H, s). |

TABLE 1-33-continued

| Example | Structure | ¹H NMR, LC-MS |
|---|---|---|
| 217 | 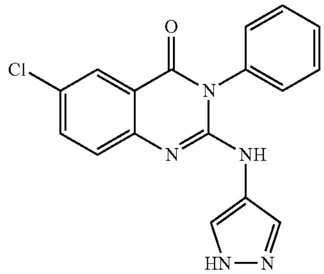 [SMILES: O=c1c2cc(Cl)ccc2nc(Nc2cn[nH]c2)n1-c1ccccc1] | ¹H NMR (400 MHz, DMSO-d6) δ: 7.42-7.48 (3H, m), 7.55-7.69 (5H, m), 7.77 (1H, s), 7.84 (1H, d, J = 2.4 Hz), 8.07 (1H, brs), 12.52 (1H, s). |
| 218 | 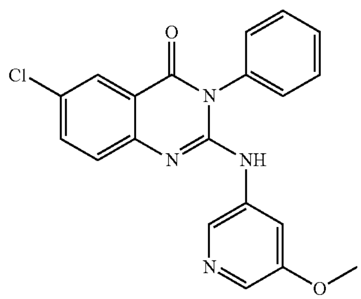 [SMILES: COc1cncc(Nc2nc3ccc(Cl)cc3c(=O)n2-c2ccccc2)c1] | ¹H NMR (400 MHz, CDCl₃) δ: 3.89 (3H, s), 6.00 (1H, s), 7.39-7.41 (2H, m), 7.44 (1H, d, J = 8.7 Hz), 7.58-7.70 (4H, m), 7.93 (1H, d, J = 2.3 Hz), 8.00 (1H, t, J = 2.3 Hz), 8.03 (1H, d, J = 2.7 Hz), 8.12 (1H, d, J = 2.3 Hz). |

TABLE 1-34

| Example | Structure | ¹H NMR, LC-MS |
|---|---|---|
| 219 | 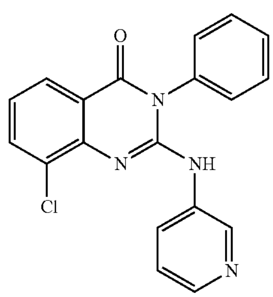 | ¹H NMR (400 MHz, CDCl₃) δ: 6.15 (1H, s), 7.22-7.25 (1H, m), 7.33-7.36 (1H, m), 7.41-7.45 (2H, m), 7.65-7.75 (3H, m), 7.81 (1H, d, J = 9.6 Hz), 8.13 (1H, d, J = 12.4 Hz), 8.34 (1H, d, J = 6.0 Hz), 8.47 (1H, d, J = 2.8 Hz), 8.63-8.66 (1H, m). |
| 220 | 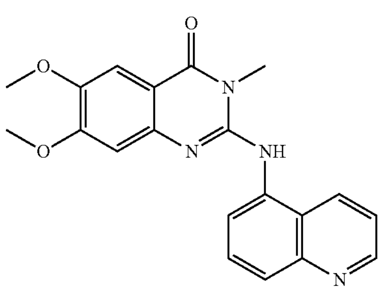 [SMILES: COc1cc2nc(Nc3cccc4ncccc34)n(C)c(=O)c2cc1OC] | LC-MS(measurement condition A), m/z; 363 (M + H) + ESI, Rt; 0.50. |

TABLE 1-34-continued

| Example | Structure | ¹H NMR, LC-MS |
|---|---|---|
| 221 | 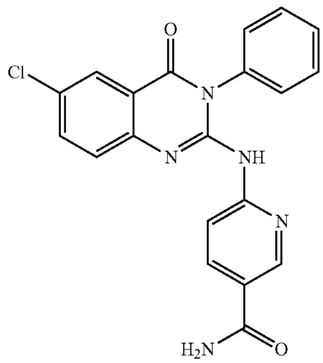 [SMILES: NC(=O)c1ccc(Nc2nc3ccc(Cl)cc3c(=O)n2-c2ccccc2)nc1] | ¹H NMR (400 MHz, DMSO-d6) δ: 6.29 (1H, d, J = 9.1 Hz), 6.64 (2H, s), 7.21 (2H, d, J = 7.9 Hz), 7.25-7.29 (1H, m), 7.35-7.39 (2H, m), 7.43-7.49 (2H, m), 7.76 (1H, dd, J = 8.5, 2.4 Hz), 8.03 (1H, d, J = 2.4 Hz), 8.09 (1H, d, J = 2.4 Hz), 13.03 (1H, s). |
| 222 | 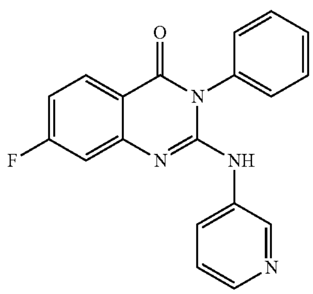 [SMILES: O=c1c2ccc(F)cc2nc(Nc2cccnc2)n1-c1ccccc1] | ¹H NMR (400 MHz, DMSO-d6) δ: 7.07-7.12 (2H, m), 7.35 (1H, dd, J = 8.3, 4.7 Hz), 7.52 (2H, d, J = 6.9 Hz), 7.57-7.64 (3H, m), 7.90-7.93 (2H, m), 8.00-8.04 (1H, m), 8.29 (1H, d, J = 4.4 Hz), 8.63 (1H, d, J = 2.4 Hz). |
| 223 | 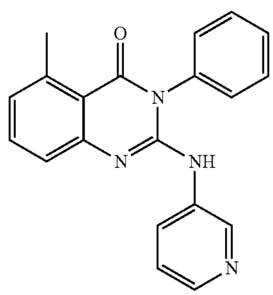 [SMILES: Cc1cccc2nc(Nc3cccnc3)n(-c3ccccc3)c(=O)c12] | ¹H NMR (400 MHz, DMSO-d6) δ: 2.66 (3H, s), 7.07 (1H, d, J = 7.2 Hz), 7.15 (1H, d, J = 8.3 Hz), 7.33 (1H, dd, J = 8.1, 4.6 Hz), 7.47-7.53 (3H, m), 7.54-7.63 (3H, m), 7.68 (1H, s), 7.94 (1H, d, J = 9.5 Hz), 8.26 (1H, d, J = 3.6 Hz), 8.65 (1H, s). |
| 224 | 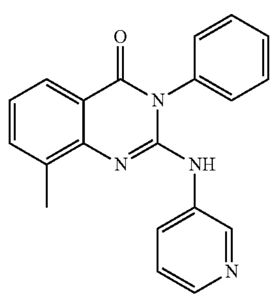 | ¹H NMR (400 MHz, DMSO-d6) δ: 2.39 (3H, s), 7.16 (1H, t, J = 7.6 Hz), 7.35 (1H, dd, J = 8.3, 4.6 Hz), 7.50 (2H, d, J = 7.0 Hz), 7.57-7.64 (4H, m), 7.76 (1H, s), 7.82 (1H, d, J = 7.6 Hz), 8.07 (1H, d, J = 8.4 Hz), 8.25 (1H, d, J = 4.0 Hz), 8.77 (1H, d, J = 2.0 Hz). |
| 225 | 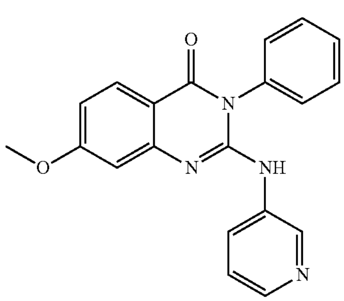 [SMILES: COc1ccc2c(=O)n(-c3ccccc3)c(Nc3cccnc3)nc2c1] | ¹H NMR (400 MHz, DMSO-d6) δ: 3.84 (3H, s), 6.76 (1H, d, J = 2.0 Hz), 6.81-6.83 (1H, m), 7.32-7.35 (1H, m), 7.47 (2H, d, J = 7.2 Hz), 7.54-7.61 (3H, m), 7.84-7.86 (2H, m), 8.26 (1H, d, J = 4.0 Hz), 8.61 (1H, s). |

TABLE 1-35

| Example | Structure | ¹H NMR, LC-MS |
|---|---|---|
| 226 | 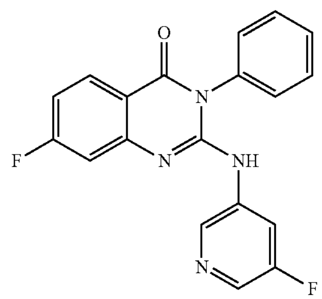 [SMILES: O=c1c2ccc(F)cc2nc(Nc2cncc(F)c2)n1-c1ccccc1] | ¹H NMR (400 MHz, DMSO-d6) δ: 7.13-7.20 (2H, m), 7.51 (2H, d, J = 7.5 Hz), 7.56-7.63 (3H, m), 8.01-8.06 (2H, m), 8.20 (1H, s), 8.28 (1H, s), 8.55 (1H, s). |
| 227 | 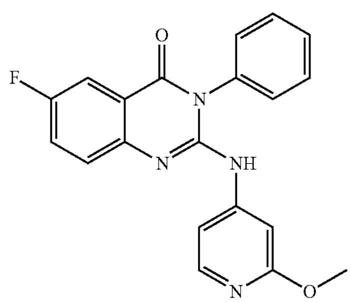 [SMILES: COc1cc(Nc2nc3ccc(F)cc3c(=O)n2-c2ccccc2)ccn1] | ¹H NMR (400 MHz, DMSO-d6) δ: 3.81 (3H, s), 7.16 (1H, dd, J = 5.7, 1.8 Hz), 7.21 (1H, d, J = 1.4 Hz), 7.47-7.50 (2H, m), 7.54-7.58 (3H, m), 7.60 (1H, s), 7.62-7.67 (1H, m), 7.67-7.70 (1H, m), 7.83 (1H, s), 7.95 (1H, d, J = 5.8 Hz). |
| 228 | 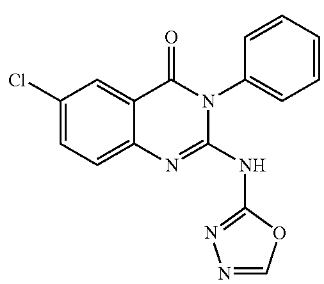 [SMILES: O=c1c2cc(Cl)ccc2nc(Nc2nnco2)n1-c1ccccc1] | ¹H NMR (400 MHz, DMSO-d6) δ: 7.36-7.38 (2H, m), 7.44-7.54 (3H, m), 7.80-7.87 (2H, m), 7.96 (1H, d, J = 2.4 Hz), 8.78 (1H, s), 12.15 (1H, s). |
| 229 | 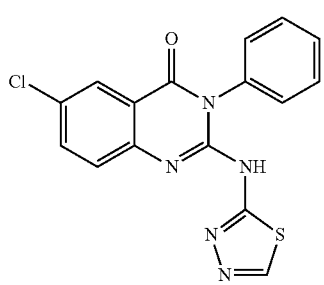 [SMILES: O=c1c2cc(Cl)ccc2nc(Nc2nncs2)n1-c1ccccc1] | ¹H NMR (400 MHz, DMSO-d6) δ: 7.32 (2H, d, J = 7.3 Hz), 7.42-7.53 (3H, m), 7.59 (1H, d, J = 9.2 Hz), 7.78 (1H, dd, J = 8.5, 2.4 Hz), 7.94 (1H, d, J = 2.4 Hz), 8.82 (1H, s), 14.18 (1H, s). |
| 230 | 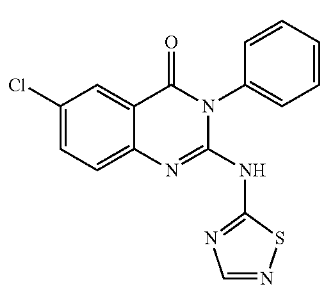 [SMILES: O=c1c2cc(Cl)ccc2nc(Nc2ncns2)n1-c1ccccc1] | ¹H NMR (400 MHz, DMSO-d6) δ: 7.36 (2H, d, J = 7.3 Hz), 7.44-7.55 (3H, m), 7.72 (1H, d, J = 9.2 Hz), 7.80 (1H, dd, J = 8.5, 2.4 Hz), 7.95 (1H, d, J = 2.4 Hz), 8.41 (1H, s), 13.94 (1H, brs). |

TABLE 1-35-continued

| Example | Structure | ¹H NMR, LC-MS |
|---|---|---|
| 231 | 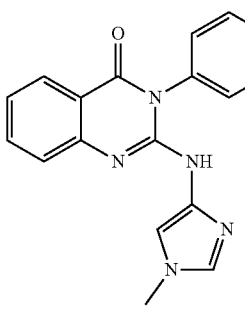 HCOOH | ¹H NMR (400 MHz, CD$_3$OD) δ: 3.74 (3H, s), 7.28 (1H, t, J = 8.0 Hz), 7.36 (1H, s), 7.37-7.45 (2H, m), 7.54-7.56 (2H, m), 7.64-7.74 (4H, m), 8.06-8.09 (1H, m). |
| 232 | 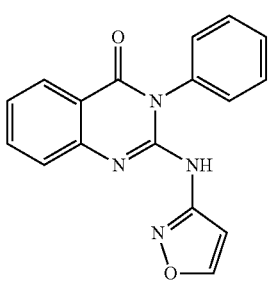 [SMILES: O=c1c2ccccc2nc(Nc2ccon2)n1-c1ccccc1] | ¹H NMR (400 MHz, DMSO-d6) δ: 7.28-7.39 (4H, m), 7.50-7.57 (4H, m), 7.70-7.74 (1H, m), 7.96-7.98 (1H, m), 8.73 (1H, brs). |

Example 233

6-fluoro-2-((5-fluoropyridin-3-yl)amino)-3-phenylquinazolin-4(3H)-one

[Chemical Formula 60]

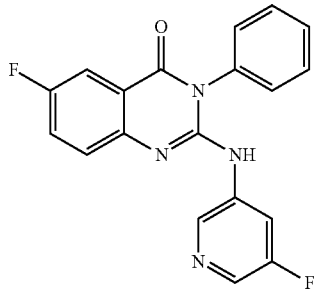

Aniline (0.5 ml) and Reference Example 4 (1.5 g) were added to a THF (15 ml) solution of potassium t-butoxide (587 mg). The mixture was stirred for 2.5 hours at room temperature. Potassium t-butoxide (588 mg) was added, and the mixture was stirred for 1.5 hours at room temperature. Water was added to the reaction solution. The resulting solid was filtered out and washed with water. The solid was dried under reduced pressure at room temperature to obtain the title compound (964 mg).

¹H-NMR (400 MHz, DMSO-d6) δ: 7.53-7.59 (3H, m), 7.65-7.75 (5H, m), 8.07-8.11 (2H, m), 8.32 (1H, d, J=2.4 Hz), 8.62 (1H, brs).

Example 234

6-fluoro-3-phenyl-2-(pyridin-3-ylamino)quinazolin-4(3H)-one

[Chemical Formula 61]

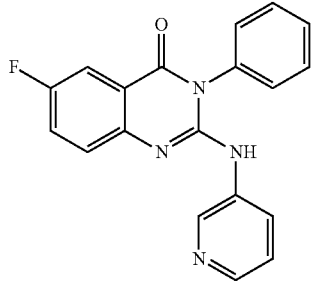

Example 12 (3.79 g) was recrystallized from acetonitrile to obtain the title compound (3.25 g) as a crystal (type II crystal).

Figure 2:
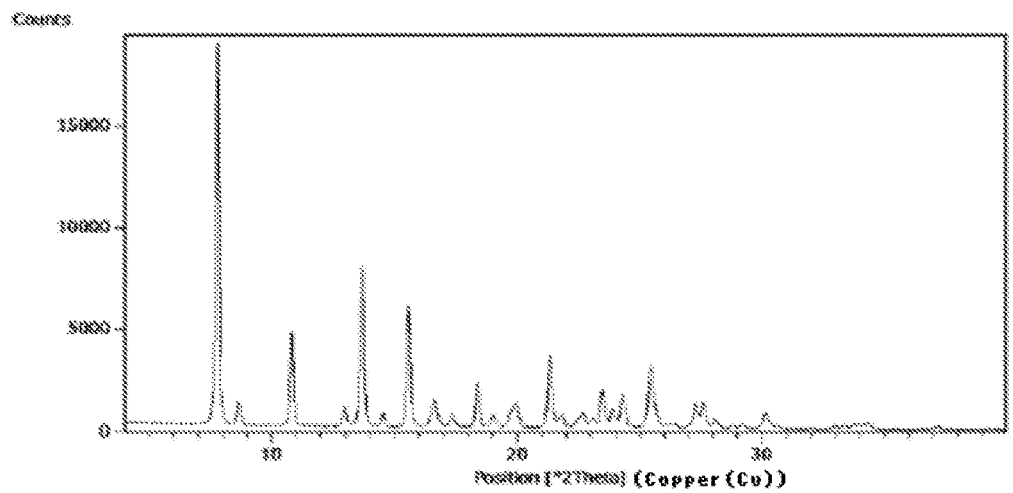
FIG. 2 shows an X-ray powder diffraction pattern of a type II crystal of the compound of Example 234.

[Type II crystal] The X-ray powder diffraction pattern is shown in FIG. 2.

Major diffraction peaks: 2θ(°)=7.80, 10.82, 13.67, 15.59, 16.62, 18.41, 21.32, 23.47, 24.33, 25.46

Characteristic diffraction peaks: 2θ(°)=7.80, 10.82, 13.67, 15.59

Example 235

6-fluoro-2-((5-fluoropyridin-3-yl)amino)-3-phenylquinazolin-4(3H)-one

[Chemical Formula 62]

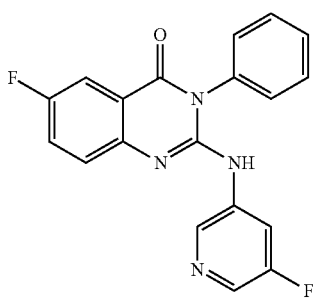

Example 233 (12.0 g) was recrystallized from ethanol to obtain the title compound (11.6 g) as a crystal (type III crystal).

Figure 3:
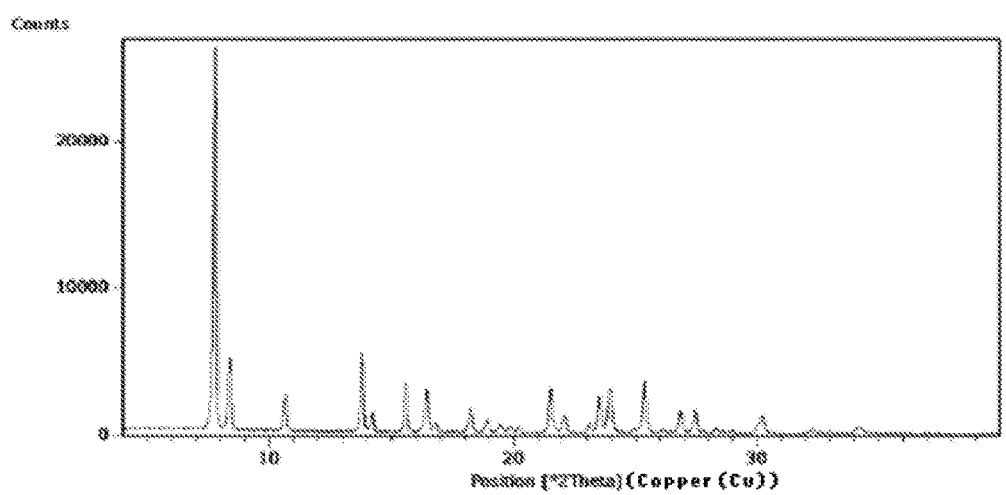
FIG. 3 shows an X-ray powder diffraction pattern of a type III crystal of the compound of Example 235.

[Type III crystal] The X-ray powder diffraction pattern is shown in FIG. 3.

Major diffraction peaks: $2\theta(°)$=7.79, 8.40, 10.66, 13.80, 15.62, 16.46, 21.52, 23.53, 23.95, 25.38

Characteristic diffraction peaks: $2\theta(°)$=7.79, 8.40, 13.80, 25.38

Example 236

4-oxo-2-(pyridin-3-ylamino)-3-(o-tolyl)-3,4-dihydroquinazoline-6-carbonitrile

[Chemical Formula 63]

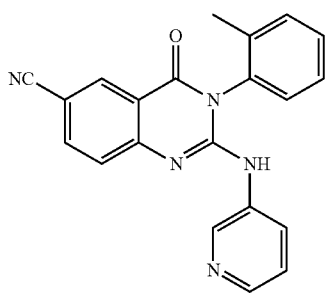

N,N-diisopropylethylamine (2.4 ml), 3-isothiocyanatopyridine (1.3 ml), and copper bromide (1.6 g) were added to a DMF (10 ml) solution of Reference Example 5 (2.4 g). The mixture was stirred for 3 hours at 85° C. Ammonium water was added to the reaction solution. The mixture was filtered through Celite. The filtrate was extracted with chloroform, and then washed with an aqueous saturated ammonium chloride solution, water, and saturated saline. The organic layer was dried with anhydrous sodium sulfate, filtered, and concentrated under reduced pressure. The resulting crude product was purified by silica gel column chromatography (eluent; hexane:ethyl acetate). The resulting crude product was recrystallized from ethanol to obtain the title compound (1.3 g) as a crystal (type IV crystal).

Figure 4:
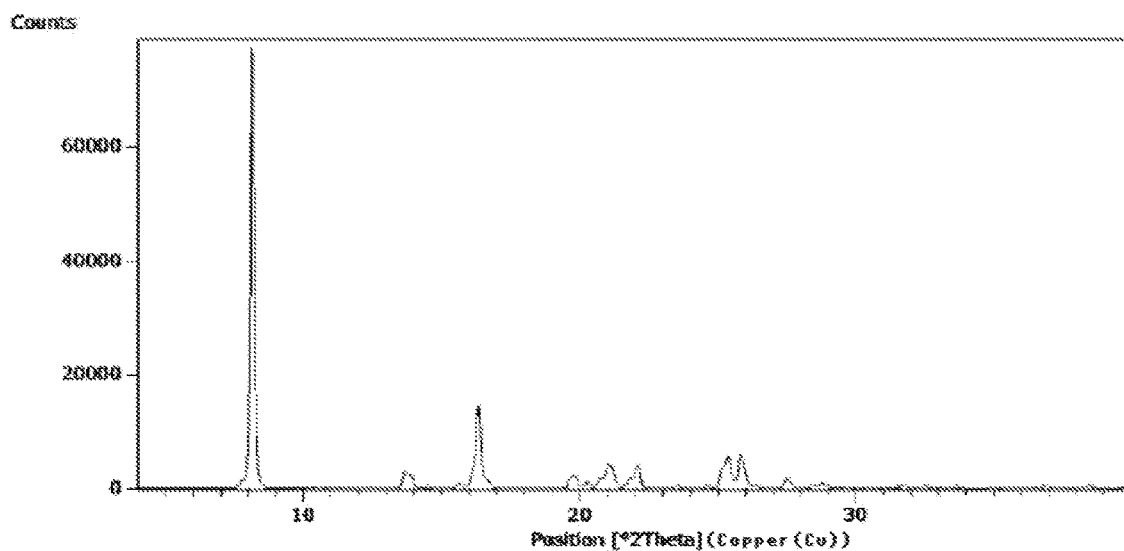
FIG. 4 shows an X-ray powder diffraction pattern of a type IV crystal of the compound of Example 236.

[Type IV crystal] The X-ray powder diffraction pattern is shown in FIG. 4.

Major diffraction peaks: $2\theta(°)$=8.15, 13.66, 13.92, 16.32, 21.04, 21.22, 22.10, 25.12, 25.37, 25.83

Characteristic diffraction peaks: $2\theta(°)$=8.15, 16.32, 25.37, 25.83

Example 237

2-((5-fluoropyridin-3-yl)amino)-4-oxo-3-(o-tolyl)-3,4-dihydroquinazoline-6-carbonitrile

[Chemical Formula 64]

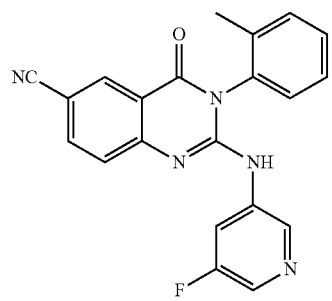

Example 114 (5.4 g) was recrystallized from ethanol to obtain the title compound (2.3 g) as a crystal (type V crystal).

Figure 5:
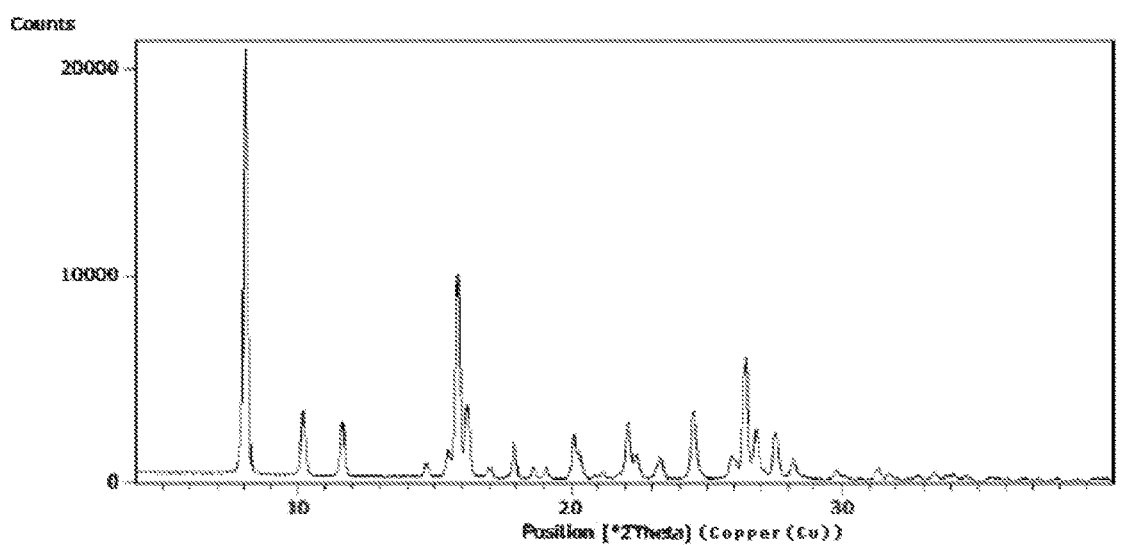
FIG. 5 shows an X-ray powder diffraction pattern of a type V crystal of the compound of Example 237.

[Type V crystal] The X-ray powder diffraction pattern is shown in FIG. 5.

Major diffraction peaks: $2\theta(°)$=8.07, 10.19, 11.62, 15.86, 16.18, 22.13, 24.51, 26.43, 26.83, 27.54

Characteristic diffraction peaks: $29(°)$=8.07, 15.86, 16.18, 26.43

X-ray powder diffraction was measured under the following conditions in the Examples described above. The resulting diffraction patterns (XRD spectra) are shown in FIGS. 1 to 5.

The crystalline form can be identified based on the characteristic diffraction peaks of each crystal shown in the diffraction diagrams of FIGS. 1 to 5.

The major diffraction peaks and characteristic diffraction peaks identified from the diffraction patterns in FIGS. 1 to 5 are shown in Example 3, 234, 235, 236, and 237. The diffraction peak values at the diffraction angle $2\theta(°)$ described in the Examples can have some measurement errors depending on the measurement equipment, measurement condition, or the like. Specifically, measurement errors can be within the range of ±0.2, and preferably ±0.1.

X-ray powder diffraction measurement method:
Detector: Spectris Power X-ray diffraction system Empyrean
X-ray tube: CuKα (wavelength: 1.54 angstroms)
Tube voltage: 45 kV
Tube current: 40 mA
Measurement range: 4 to 40° ($2\theta$)
Step width: 0.013 degrees
Integration time: 100 seconds/step

Test Examples

While pharmacological test results for the representative compounds of the present disclosure are shown below to explain the pharmacological effect of the compounds, the present disclosure is not limited to the Test Examples.

Test Example 1

Test for Measuring Hyperexcitation Suppression Activity Using Neurons Induced to Differentiate from SCN1A Gene Deficient Human iPS Cells (1) Induction of Differentiation from Human iPS cells to Neurons SCN1A gene mutated cells established from iPS cell strain derived from a healthy individual (clone name: 201B7, obtained from the Center for iPS Cell Research and Application, Kyoto University) were induced to differentiate into glutamatergic excitatory neurons or γ-aminobutyric acid (GABA)-ergic inhibitory neurons, and the neurons were maintained using a BrainPhys Neuronal Medium (STEM-CELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. At 7 days after inducing differentiation, the glutamatergic excitatory neurons and GABAergic inhibitory neurons were mixed at a ratio of 4:1 and seeded on a 384-well plate (Corning, Cat #353962) coated with poly-L-lysine (Sigma-Aldrich, cat #P4707) and iMatrix-511 silk (Matrixome, cat #892021). Half of the culture solution was exchanged once every 3 to 4 days.

(2) Fluorescent Calcium Probe Treatment, Addition of Compound, and Evaluation of Intracellular Calcium Concentration Half of the culture solution was removed on day 60 from induction of differentiation or thereafter. A medium for measurement comprising a fluorescent calcium probe (Molecular Device, product name: FLIPR Calcium 6 Assay Bulk Kit, cat #R8191) was added at an amount equal to the remaining medium. The culture was left standing for 30 minutes and subjected to measurement. As the medium for measurement, 20 mM Hepes (Thermo Fisher Scientific, cat #15630-080) and 0.1% bovine serum albumin (Sigma-Aldrich, cat #A9576)-containing Hank's buffer (Thermo Fisher Scientific, cat #14065-056) was used.

The test compounds were serially diluted with a dimethyl sulfoxide (DMSO) solution so that the final concentration would be 0.1 to 100 μM to prepare a concentrate with a concentration that is 6-fold of the final concentration.

The intensity of fluorescence of a calcium probe was measured over time with FDSS7000EX (Hamamatsu Photonics) to evaluate the change in intracellular calcium concentrations. First, the intensity of fluorescence was measured for 2 minutes. The compound solutions were then added using FDSS7000EX for an additional 8 minute measurement of fluorescence intensity. The frequency of spontaneous calcium oscillation was quantified as an indicator of nerve excitation. With the frequency for 2 minutes before the addition of the compound solutions as 100%, the ratio of frequency for the last 2 minutes after addition of the compound solutions was calculated. The inhibitory activity (%) at each serial dilution concentration was determined, and the 50% inhibitory concentration (IC50) or the inhibition ratio (%) at a certain concentration (the concentration described after @ in Tables 2-1 and 2-2) was determined for each test compound. Tables 2-1 and 2-2 show inhibitory activity data for representative compounds.

TABLE 2-1

| Example | IC50 or inhibition rate |
|---|---|
| 1 | 31% @1 μM |
| 2 | 57% @10 μM |
| 3 | 97% @1 μM |
| 4 | 88% @0.1 μM |
| 5 | IC50 = 6.1 μM |
| 6 | IC50 = 0.4 μM |
| 7 | IC50 = 6.5 μM |
| 8 | IC50 = 1.0 μM |
| 9 | IC50 = 0.6 μM |
| 10 | IC50 = 0.3 μM |
| 11 | IC50 = 5.8 μM |
| 12 | IC50 = 0.2 μM |
| 13 | 20% @100 μM |
| 14 | IC50 = 1.8 μM |
| 15 | 99% @1 μM |
| 16 | 42% @10 μM |
| 17 | 17% @100 μM |
| 18 | IC50 = 0.8 μM |
| 19 | IC50 = 2.2 μM |
| 20 | IC50 = 4.9 μM |
| 21 | 27% @10 μM |
| 22 | 70% @10 μM |
| 23 | 61% @1 μM |
| 24 | 54% @10 μM |
| 25 | 82% @10 μM |
| 26 | 23% @1 μM |
| 27 | 37% @1 μM |
| 28 | 32% @1 μM |
| 29 | 82% @10 μM |
| 30 | 67% @1 μM |
| 31 | 93% @1 μM |
| 32 | 80% @1 μM |
| 33 | 100% @10 μM |
| 34 | 57% @10 μM |
| 35 | 88% @1 μM |
| 36 | 32% @10 μM |
| 37 | 68% @10 μM |
| 38 | 88% @1 μM |
| 39 | 100% @1 μM |
| 40 | 100% @1 μM |
| 41 | 95% @1 μM |
| 42 | 98% @1 μM |
| 43 | 17% @10 μM |
| 44 | 81% @10 μM |
| 45 | 100% @1 μM |
| 46 | 34% @100 μM |
| 47 | 89% @10 μM |
| 48 | 55% @1 μM |
| 49 | 34% @10 μM |
| 50 | 100% @10 μM |
| 51 | 100% @1 μM |
| 52 | 63% @1 μM |
| 53 | 79% @10 μM |
| 54 | 95% @1 μM |
| 55 | 88% @10 μM |
| 56 | 100% @10 μM |
| 57 | 21% @1 μM |
| 58 | 100% @10 μM |
| 59 | 39% @1 μM |
| 60 | 100% @10 μM |
| 61 | 79% @10 μM |
| 62 | 43% @1 μM |
| 63 | 23% @1 μM |
| 64 | 24% @1 μM |
| 65 | 100% @10 μM |
| 66 | 62% @10 μM |
| 67 | 100% @10 μM |
| 68 | 100% @10 μM |
| 69 | 39% @0.1 μM |
| 70 | 58% @1 μM |
| 71 | 51% @1 μM |
| 72 | 100% @10 μM |
| 73 | 86% @1 μM |
| 74 | 100% @10 μM |
| 75 | 100% @10 μM |
| 76 | 35% @1 μM |
| 77 | 26% @10 μM |

TABLE 2-1-continued

| Example | IC50 or inhibition rate |
|---|---|
| 78 | 100% @10 μM |
| 79 | 47% @1 μM |
| 80 | 49% @10 μM |
| 81 | 35% @10 μM |
| 82 | 17% @10 μM |
| 83 | 96% @10 μM |
| 84 | 96% @10 μM |
| 85 | 59% @10 μM |
| 86 | 31% @100 μM |
| 87 | 26% @1 μM |
| 88 | 95% @10 μM |
| 89 | 20% @1 μM |
| 90 | 51% @10 μM |
| 91 | 37% @100 μM |
| 92 | 38% @100 μM |
| 93 | 53% @10 μM |
| 94 | 27% @1 μM |
| 95 | 98% @10 μM |
| 96 | 100% @100 μM |
| 97 | 100% @100 μM |
| 98 | 51% @1 μM |
| 99 | 94% @10 μM |
| 100 | 100% @10 μM |
| 101 | 6% @10 μM |
| 102 | 92% @10 μM |
| 103 | 84% @1 μM |
| 104 | 29% @0.1 μM |
| 105 | 100% @1 μM |
| 106 | 17% @0.1 μM |
| 107 | 89% @0.1 μM |
| 108 | 62% @0.1 μM |
| 109 | 59% @0.1 μM |
| 110 | 66% @1 μM |
| 111 | 35% @0.1 μM |
| 112 | 32% @0.1 μM |
| 113 | 91% @1 μM |
| 114 | 55% @0.1 μM |
| 115 | 81% @1 μM |
| 116 | 59% @100 μM |
| 117 | 71% @100 μM |
| 118 | 47% @1 μM |
| 119 | 20% @1 μM |
| 120 | 69% @1 μM |
| 121 | 28% @1 μM |
| 122 | 61% @1 μM |
| 123 | 56% @1 μM |
| 124 | 32% @1 μM |
| 125 | 29% @1 μM |
| 126 | 80% @10 μM |
| 127 | 96% @1 μM |
| 128 | 69% @1 μM |
| 129 | 50% @1 μM |
| 130 | 44% @1 μM |
| 131 | 100% @10 μM |
| 132 | 38% @1 μM |
| 133 | 51% @1 μM |
| 134 | 56% @1 μM |
| 135 | 24% @1 μM |
| 136 | 5% @100 μM |
| 137 | 85% @1 μM |
| 138 | 70% @1 μM |
| 139 | 100% @10 μM |
| 140 | 46% @1 μM |
| 141 | 97% @1 μM |
| 142 | 86% @1 μM |
| 143 | 45% @1 μM |
| 144 | 16% @100 μM |
| 145 | 100% @1 μM |
| 146 | 11% @10 μM |
| 147 | IC50 = 2.7 μM |
| 148 | 10% @100 μM |

TABLE 2-2

| Example | Inhibition rate |
|---|---|
| 149 | 32% @10 μM |
| 150 | 26% @1 μM |
| 151 | 2% @10 μM |
| 152 | 15% @10 μM |
| 153 | 99% @1 μM |
| 154 | 98% @10 μM |
| 155 | 81% @10 μM |
| 156 | 95% @10 μM |
| 157 | 90% @10 μM |
| 158 | 100% @10 μM |
| 159 | 56% @10 μM |
| 160 | 58% @10 μM |
| 161 | 35% @1 μM |
| 162 | 39% @10 μM |
| 163 | 70% @1 μM |
| 164 | 92% @10 μM |
| 165 | 100% @10 μM |
| 166 | 36% @10 μM |
| 167 | 100% @10 μM |
| 168 | 58% @1 μM |
| 169 | 100% @10 μM |
| 170 | 100% @100 μM |
| 171 | 100% @100 μM |
| 172 | 100% @100 μM |
| 173 | 6% @100 μM |
| 174 | 78% @1 μM |
| 175 | 25% @10 μM |
| 176 | 88% @10 μM |
| 177 | 100% @100 μM |
| 178 | 76% @10 μM |
| 179 | 98% @10 μM |
| 180 | 35% @1 μM |
| 181 | 73% @1 μM |
| 182 | 72% @10 μM |
| 183 | 13% @100 μM |
| 184 | 54% @100 μM |
| 185 | 31% @10 μM |
| 186 | 100% @10 μM |
| 187 | IC50 > 10 μM |
| 188 | IC50 > 10 μM |
| 189 | IC50 > 10 μM |
| 190 | IC50 > 10 μM |
| 191 | IC50 > 10 μM |
| 192 | IC50 > 10 μM |
| 193 | IC50 > 10 μM |
| 194 | IC50 > 10 μM |
| 195 | IC50 > 10 μM |
| 196 | IC50 > 10 μM |
| 197 | IC50 > 10 μM |
| 198 | IC50 > 10 μM |
| 199 | IC50 > 10 μM |
| 200 | IC50 > 10 μM |
| 201 | IC50 > 10 μM |
| 202 | IC50 > 10 μM |
| 203 | IC50 > 10 μM |
| 204 | IC50 > 10 μM |
| 205 | IC50 > 10 μM |
| 206 | IC50 > 100 μM |
| 207 | IC50 > 10 μM |
| 208 | IC50 > 100 μM |
| 209 | IC50 > 100 μM |
| 210 | IC50 > 100 μM |
| 211 | IC50 > 100 μM |
| 212 | IC50 > 10 μM |
| 213 | IC50 > 100 μM |
| 214 | IC50 > 100 μM |
| 215 | IC50 > 10 μM |
| 216 | IC50 > 100 μM |
| 217 | IC50 > 10 μM |
| 218 | IC50 > 10 μM |
| 219 | IC50 > 100 μM |
| 220 | IC50 > 10 μM |
| 221 | IC50 > 10 μM |
| 222 | IC50 > 100 μM |
| 223 | IC50 > 100 μM |
| 224 | IC50 > 100 μM |
| 225 | IC50 > 100 μM |
| 226 | IC50 > 100 μM |

TABLE 2-2-continued

| Example | Inhibition rate |
|---|---|
| 227 | IC50 > 100 μM |
| 228 | IC50 > 10 μM |
| 229 | 5% @10 μM |
| 230 | 2% @10 μM |
| 231 | IC50 > 10 μM |
| 232 | 73% @10 μM |

As shown in these tables, the compounds of the present disclosure exhibited inhibitory activity in a test for measuring the activity for suppressing hyperexcitation using the neurons induced to differentiate from SCN1A gene deficient human iPS cells.

Test Example 2

Evaluation of Epileptic Spike Using SCN1A-Mutated Animal

This test evaluates the inhibitory effect of a medicament on epileptic spike expressed with an SCN1A loss-of-function genetic mutation. The animal model used in this test is F1 generated by interbreeding a BALB/c-Scn1a <+/−> mouse (catalog number: RBRC06422; this mouse model can be provided by the RIKEN BioResource Research Center (RIKEN BRC) through the National BioResource Project directed by the Ministry of Education, Culture, Sports, Science and Technology, Japan. The mouse has a genetic mutation that is a deletion in the SCN1A gene in a similar manner as Dravet syndrome patients and can be used as a spontaneous Dravet syndrome animal model with a phenotype of Dravet syndrome exhibiting febrile seizure accompanying increase in body temperature (reference: Annual report of the Japan Epilepsy Research Foundation 2015: 26: 69-76)) with a C57BL/6J mouse.

Febrile seizure was induced in the SCN1A-mutated mice (6 to 10 week old) described above from increasing the body temperature by placing and continuously incubating the mice in a plastic chamber whose internal temperature was increased by incubation using a warm bath of about 43° C. After two weeks from inducing febrile seizure, a head mount (cat #8201-SS, Pinnacle Technology) was mounted on the head of the mice. Two weeks after mounting the head mount, the F1 SCN1A loss-of-function genetic mutation mice (25 to 32 g) were connected to a seizure EEG recording system (Pinnacle Technology), and the test compound was administered. The epileptic spike frequency over 3 hours before and after administration of the compound was measured, and the dose at which epileptic spike frequency is suppressed to 50% after the administration (ED50) was calculated. The results are shown in the following Table 3.

TABLE 3

| Example | ED50 (mg/kg, p.o.) |
|---|---|
| 3 | 0.66 |
| 12 | 0.18 |
| 14 | 5.83 |
| 32 | 1.48 |
| 40 | 0.12 |
| 109 | 0.19 |
| 114 | 0.044 |

Test Example 3

Evaluation of Model Subcutaneously Injected with Pentetrazol (Minimum Seizure Model, scPTZ)

This test evaluates the antiseizure effect of a medicament. The animal model used in this test is a phenotype of generalized absence seizure or myoclonic seizure. The test compound was orally administered to male Slc:ddY mice (group of five, body weight: 20 to 30 g), and 85 mg of pentetrazol/kg was subcutaneously administered 1 hour later. The presence/absence of expression of clonic seizure during 30 minutes was then observed. The dose at which 50% of animals expressed clonic seizure (ED50) was calculated. 0.5% methylcellulose solution was administered for the control. The following Table 4 shows the results.

TABLE 4

| Example | ED50 (mg/kg, p.o.) |
|---|---|
| 3 | 0.74 |
| 12 | 0.25 |
| 14 | 4.17 |
| 32 | 4.17 |
| 40 | 0.27 |
| 109 | 0.25 |
| 114 | 0.065 |

Test Example 4

Evaluation of Maximal Electroshock Seizure (MES) Model

This test evaluates the antiseizure effect of a medicament in the same manner as Test Example 3. The animal model used in this test is a phenotype of generalized tonic-clonic seizure and secondary generalized partial seizure. The test compound was orally administered to male Slc:ddY mice (group of five, body weight: 20 to 30 g), and electrical stimulation (60 Hz, 50 mA, 0.2 seconds) was applied through the cornea 1 hour later. Suppression of induced expression of tonic extensor seizure of the rear limb was observed. The dose at which 50% of animals expressed clonic extensor seizure (ED50) was calculated. 0.5% methylcellulose solution was administered for the control. The following Table 5 shows the results.

TABLE 5

| Example | ED50 (mg/kg, p.o.) |
|---|---|
| 12 | 0.56 |
| 40 | 0.56 |

As shown in this table, the compound of the present disclosure exhibited antiseizure effects in evaluation of epileptic spike and/or evaluation of model subcutaneously injected with pentetrazol (minimum seizure model, scPTZ) and/or evaluation of maximal electroshock seizure (MES) model using SCN1A mutant animals with oral administration.

Test Example 5

Rotarod Evaluation

The test evaluates the effect of suppressing the ability of motor coordination of a medicament. Male Slc:ddy mice (body weight: 20 to 30 g) were trained to walk for 5 minutes with a rotarod apparatus (apparatus for rotating a cylindrical bar with a 4 cm diameter, 12 rpm) on the day of the test. A test compound was orally administered to a group of 5 mice. The mice were placed on the rotarod apparatus (15 rpm) after 50 minutes, and the walking was observed for 180 seconds. Animals that fell off within 180 seconds due to incoordination were counted. The dosage at which 50% of animals fall off (TD50) was calculated. 0.5% methylcellulose solution was administered for the control. Table 6 shows the results.

TABLE 6

| Example | TD50 (mg/kg, p.o.) |
| --- | --- |
| 3 | 2.0 |
| 12 | 1.8 |
| 14 | 7.38 |
| 32 | 8.83 |
| 40 | 1.8 |
| 109 | 2.0 |
| 114 | 0.2 |

Test Example 6

Three-Chambered Test Evaluation

This test evaluates the effect of improving reduced sociability, which is a core symptom of autism spectrum disorder, of a medicament. The animal model used in this test is F1 generated by interbreeding a BALB/c-Scn1a <+/−> mouse with a C57BL/6J mouse in the same manner as Test Example 2.

Febrile seizure is induced in the SCN1A mutated mice (6 to 10 week old) described above from increasing the body temperature by placing and continuously incubating the mice in a plastic chamber whose internal temperature is increased by incubating using a warm bath of about 43° C. After two weeks from inducing febrile seizure, a three-chambered test is conducted. A cage with a decoy mouse is placed on one side of a room of a three-chamber test apparatus, and a cage with an object is placed in the other room. Test compounds are orally administered to the F1 SCN1A loss-of-function genetic mutation mice (25 to 32 g). After 1 hour, the mice are allowed to freely explore within the apparatus for 10 minutes. The time of sniffing the decoy mouse and object is measured.

Test Example 7

Evaluation of Cognitive Function by Novel Object Recognition Test (Hereinafter, also Referred to as "NORT")

This test evaluates the effect of improving the cognitive function of a compound. Decease in memory of known objects is observed, with a correlation with the interval between the first trial (training) and the second trial (test) in NORT using AD (Alzheimer's disease) mouse models, i.e., APP-Tg mice or rTg4510 mice. For example, if the second trial is performed 3 hours after the first trial, significant memory loss is observed in APP-Tg mice or rTg4510 mice compared to healthy mice, with no difference in the time for exploring new objects and known objects.

The APP-Tg mice used in this test are generated by constructing an expression cassette linked with a human APP751 isoform introduced with Swedish (K670N/M671L) and Indiana (V717F) mutations downstream of a mouse Thy-1 promotor, and then injecting the cassette into a fertilized mouse ovum, and transplanting this to a foster parent. Since the generated mice exhibit early Aβ accumulation and cognitive function disorder in the brain, such mice can be used in evaluation of cognitive function or the like.

The rTg4510 mice used in this test are generated by interbreeding a Tg(tauP301L)4510 mouse (Stock No. 015815) with a CaMKII-tTA mouse (Stock No. 007004) purchased from The Jackson Laboratory, and breeding the mice. Since the generated mice overexpress human FTDP-17 tau mutation in the forebrain, and exhibits age dependent intracranial tau aggregate accumulation and cognitive function disorder, the mice can be used in the evaluation cognitive function or the like.

Test compounds are administered to the generated APP-Tg mice or rTg4510 mice. The first trial is conducted after 30 to 60 minutes after administration or after 1 month of administration of the compound mixed with feed. The second trial is conducted three hours after the first trial. Times exploring a new object and a known object in the second trial are each evaluated. Identification index is calculated from the time exploring a new object and a known objective in the second trial. The effect of improving cognitive function of the test compound is studied by comparison with a test compound unadministered group, with the index as an indicator of cognitive function. The identification index is calculated by the following numerical formula.

Identification index={(time exploring a new object)−(time exploring a known object)}/{(time exploring a new object)+(time exploring a known object)}

As described above, the compounds of the present disclosure exhibited activity to suppress hyperexcitation of the neural circuit, which is understood to be in the background of various epileptic conditions, and exhibited a potent antiseizure activity in epilepsy models using human cells and multiple seizure animal models. Thus, the compound is useful as an antiepileptic medicament exhibiting a broad spectrum of therapeutic effect (therapeutic medicament and/or prophylactic medicament for epileptic seizures (generalized seizures including tonic, clonic, absence, myoclonic, and atonic seizures, focal seizure, epileptic spasms, and unknown seizures), status epilepticus, epilepsy syndromes (Dravet syndrome, Ohtahara syndrome, West syndrome, Lennox-Gastaut syndrome, autosomal dominant nocturnal frontal lobe epilepsy, mesial temporal lobe epilepsy with hippocampal sclerosis, Rasmussen syndrome, etc.), epilepsy attributed to structural/metabolic etiology (cortical dysplasia, neurocutaneous syndrome (tuberous sclerosis complex, Sturge-Weber syndrome, etc.), etc.), etc., developmental disorder, mental disorder, or cognitive disorder manifested as a complication thereof, and the like). The compound is also expected to have an effect of improving the pathological condition for a disorder or disease with a background in the imbalance between excitation signals and inhibition signals in the neural circuit (developmental disorders (autism spectrum disorder, Rett syndrome, Angelman syndrome, fragile X syndrome, attention deficit hyperactivity disorder, etc.), mental disorders (schizophrenia, bipolar disorder, depression, anxiety, obsessive-compulsive disorder, etc.), and cognitive disorders (Alzheimer's disease, other dementia, Parkinson's disease, etc.)).

As disclosed above, the present disclosure is exemplified by the use of its preferred embodiments. However, it is understood that the scope of the present disclosure should be interpreted solely based on the Claims. The present application claims priority to Japanese Patent Application No. 2020-77487 (filed on Apr. 24, 2020). The entire content thereof is incorporated herein by reference. It is also understood that any patent, any patent application, and any references cited herein should be incorporated herein by reference in the same manner as the contents are specifically described herein.

INDUSTRIAL APPLICABILITY

Since the compound of the present disclosure exhibits activity to suppress hyperexcitation of the neural circuit, the compound is useful as a therapeutic medicament and/or prophylactic medicament for a disorder or disease associated with an abnormal nerve excitation such as epilepsy.

The invention claimed is:
1. A compound represented by formula (1):

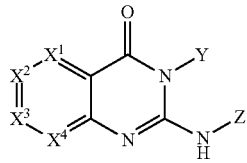

or a pharmaceutically acceptable salt thereof,
wherein
$X^1$ represents $CR^1$ or N,
$X^2$ represents $CR^2$ or N,
$X^3$ represents $CR^3$ or N,
$X^4$ represents $CR^4$ or N,
wherein (1) if $X^1$ is N, $X^2$ is $CR^2$, $X^3$ is $CR^3$, and $X^4$ is $CR^4$, (2) if $X^2$ is N, $X^1$ is $CR^1$, $X^3$ is $CR^3$, and $X^4$ is $CR^4$, (3) if $X^3$ is N, $X^1$ is $CR^1$, $X^2$ is $CR^2$, and $X^4$ is $CR^4$, and (4) if $X^4$ is N, $X^1$ is $CR^1$, $X^2$ is $CR^2$, and $X^3$ is $CR^3$,
Y represents optionally substituted $C_{1-6}$ alkyl, an optionally substituted $C_{3-10}$ alicyclic group, an optionally substituted 4- to 10-membered non-aryl heterocycle, optionally substituted $C_{6-10}$ aryl, or optionally substituted 5- to 10-membered heteroaryl,
Z represents optionally substituted 5- to 10-membered heteroaryl, wherein when Z is substituted, it is substituted with 1 to 3 of the same or different substituents selected from the group consisting of halogen, cyano, dimethylamino, $C_{1-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy),
wherein Z does not attach to a nitrogen atom to which the heteroaryl attaches at a nitrogen atom on a ring of the heteroaryl group $R^1$, $R^2$, $R^3$, and $R^4$ each independently represent a hydrogen atom, halogen, cyano, $C_{1-6}$ alkylsulfonyl, —$SO_2$—$NR^5R^6$, —$NR^7R^8$, —$NR^9$—C(=O)$R^{10}$, —$NR^{11}$—$SO_2$—$R^{12}$, —C(=O)$NR^{13}R^{14}$, —C(=O)$OR^{15}$, optionally substituted $C_{1-6}$ alkyl, or optionally substituted $C_{1-6}$ alkoxy, $R^5$, $R^6$, $R^7$, $R^8$, $R^9$, $R^{10}$, $R^{11}$, $R^{12}$, $R^{13}$, $R^{14}$, and $R^{15}$ are the same or different, each independently, and if there are multiple instances, they each independently represent a hydrogen atom, a $C_{3-6}$ alicyclic group, or $C_{1-6}$ alkyl (wherein the alicyclic group and the alkyl are each independently optionally substituted with 1 to 3 of the same or different substituents selected from the group consisting of halogen, a hydroxyl group, a $C_{3-10}$ alicyclic group, $C_{1-6}$ alkoxy, and a 4- to 6-membered non-aryl heterocyclic group), wherein $R^5$ and $R^6$, $R^7$ and $R^8$, and $R^{13}$ and $R^{14}$, together with the nitrogen atom to which they are attached, may form a 4- to 10-membered nitrogen-containing non-aryl heterocyclic group (wherein the ring is optionally substituted with 1 to 5 of the same or different substituents selected from the group consisting of halogen, hydroxy, $C_{1-6}$ alkyl, and $C_{1-6}$ alkoxy), provided that the compound is not:
a compound represented by formula (W-1):

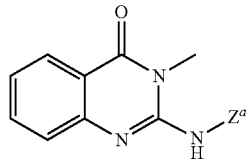

wherein
$Z^a$ is optionally substituted 5- to 10-membered heteroaryl;
a compound represented by formula (W-2):

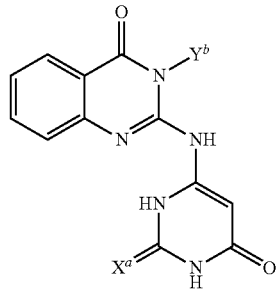

wherein
X$^a$ is O or S, and Y$^b$ is ethyl, unsubstituted phenyl, 4-chlorophenyl, or 4-methoxyphenyl;
a compound represented by formula (W-3):

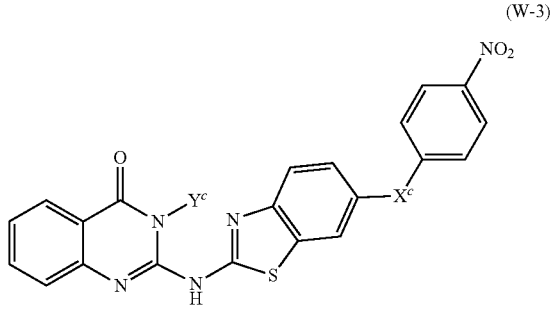

(W-3)

wherein
X$^c$ is —S— or —SO$_2$—, and Y$^c$ is unsubstituted phenyl, 4-chlorophenyl, or 4-methoxyphenyl;
a compound represented by formula (W-4):

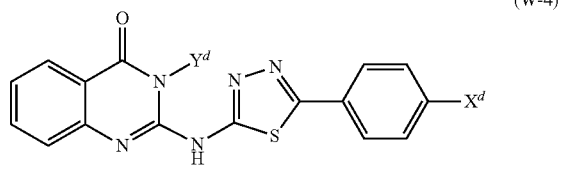

(W-4)

wherein
X$^d$ is methoxy, chloro, or dimethylamino, and Y$^d$ is ethyl, unsubstituted phenyl, 4-chlorophenyl, or 4-methoxyphenyl;
2-{(4,6-dimethylpyrimidin-2-yl)amino}-3-isopentylquinazolin-4 (3H)-one;
3-(pyridin-2-yl)-2-(pyridin-2-ylamino) quinazolin-4 (3H)-one;
3-methyl-2-{[2-((1-methylpiperidin-4-yl) methoxy) pyridin-3-yl]amino}pyrido[3,4-d]pyrimidin-4 (3H)-one; or
3-methyl-2-{[2-((1-methylpiperidin-4-yl) methoxy) pyridin-3-yl]amino}pyrido[2,3-d]pyrimidin-4 (3H)-one.

2. The compound or the pharmaceutically acceptable salt thereof according to claim 1, wherein X$^1$ is CR$^1$.

3. The compound or the pharmaceutically acceptable salt thereof according to claim 1, wherein X$^2$ is CR$^2$.

4. The compound or the pharmaceutically acceptable salt thereof according to claim 1, wherein X$^3$ is CR$^3$.

5. The compound or the pharmaceutically acceptable salt thereof according to claim 1, wherein X$^4$ is CR$^4$.

6. The compound or the pharmaceutically acceptable salt thereof according to claim 1, wherein R$^1$, R$^2$, R$^3$, and R$^4$ are each independently a hydrogen atom, halogen, cyano, C$_{1-6}$ alkoxy, or C$_{1-6}$ alkyl (wherein the alkoxy and the alkyl are each independently optionally substituted with 1 to 3 of the same or different substituents selected from the group consisting of halogen, hydroxy, and C$_{1-6}$ alkoxy).

7. The compound or the pharmaceutically acceptable salt thereof according to claim 1, wherein R$^1$, R$^3$, and R$^4$ are all hydrogen atoms, and R$^2$ is a hydrogen atom, halogen, cyano, C$_{1-6}$ alkyl (wherein the alkyl is optionally substituted with 1 to 3 fluorine or a methoxy group), or C$_{1-6}$ alkoxy.

8. The compound or the pharmaceutically acceptable salt thereof according to claim 1, wherein R$^1$, R$^3$, and R$^4$ are all hydrogen atoms, and R$^2$ is a hydrogen atom, fluorine, chloro, cyano, or C$_{1-6}$ alkyl (wherein the alkyl is optionally substituted with 1 to 3 fluorine or a methoxy group).

9. The compound or the pharmaceutically acceptable salt thereof according to claim 1, wherein R$^1$, R$^3$, and R$^4$ are all hydrogen atoms, and R$^2$ is fluorine or cyano.

10. The compound or the pharmaceutically acceptable salt thereof according to claim 1, wherein Y is
(1) C$_{1-6}$ alkyl optionally substituted with 1 to 3 of the same or different substituents selected from the group consisting of halogen, hydroxy, amino, dimethylamino, a C$_{3-6}$ alicyclic group, a 4- to 10-membered nitrogen-containing non-aryl heterocyclic group, C$_{1-6}$ alkoxy, C$_{6-10}$ aryl (wherein the alicyclic group, the nitrogen-containing non-aryl heterocyclic group, the alkoxy, and the aryl group are each independently optionally substituted with 1 to 3 of the same or different substituents selected from the group consisting of halogen, cyano, a C$_{3-6}$ alicyclic group, C$_{1-6}$ alkyl optionally substituted with 1 to 5 fluorine, and C$_{1-6}$ alkoxy), and 5- to 10-membered heteroaryl (wherein the heteroaryl group is optionally substituted with 1 to 3 of the same or different substituents selected from the group consisting of halogen, cyano, a C$_{3-6}$ alicyclic group, C$_{1-6}$ alkyl optionally substituted with 1 to 5 fluorine, and C$_{1-6}$ alkoxy),
(2) a C$_{3-10}$ alicyclic group optionally substituted with 1 to 3 of the same or different substituents selected from the group consisting of halogen, hydroxy, amino, dimethylamino, C$_{1-6}$ alkyl optionally substituted with 1 to 5 fluorine, a C$_{3-6}$ alicyclic group, a 4- to 10-membered nitrogen-containing non-aryl heterocyclic group, C$_{1-6}$ alkoxy, C$_{6-10}$ aryl (wherein the alicyclic group, the nitrogen-containing non-aryl heterocyclic group, the alkoxy, and the aryl group are each independently optionally substituted with 1 to 3 of the same or different substituents selected from the group consisting of halogen, cyano, a C$_{3-6}$ alicyclic group, C$_{1-6}$ alkyl optionally substituted with 1 to 5 fluorine, and C$_{1-6}$ alkoxy), and 5- to 10-membered heteroaryl (wherein the heteroaryl group is optionally substituted with 1 to 3 of the same or different substituents selected from the group consisting of halogen, cyano, a C$_{3-6}$ alicyclic group, C$_{1-6}$ alkyl optionally substituted with 1 to 5 fluorine, and C$_{1-6}$ alkoxy),
(3) a 4- to 10-membered non-aryl heterocyclic group optionally substituted with 1 to 3 of the same or different substituents selected from the group consisting of halogen, hydroxy, amino, dimethylamino, C$_{1-6}$ alkyl optionally substituted with 1 to 5 fluorine, a C$_{3-6}$ alicyclic group, C$_{1-6}$ alkoxy, and C$_{6-10}$ aryl (wherein the alicyclic group, the alkoxy, and the aryl group are each independently optionally substituted with 1 to 3 of the same or different substituents selected from the group consisting of halogen, cyano, a C$_{3-6}$ alicyclic group, C$_{1-6}$ alkyl optionally substituted with 1 to 5 fluorine, and C$_{1-6}$ alkoxy),
(4) C$_{6-10}$ aryl optionally substituted with 1 to 3 of the same or different substituents selected from the group consisting of halogen, cyano, dimethylamino, C$_{1-6}$ alkoxy, and C$_{1-6}$ alkyl (wherein the alkoxy and the alkyl are each independently optionally substituted with 1 to 3 of the same or different substituents selected from the group consisting of halogen, hydroxy, and $C_{1-6}$ alkoxy), or (5) 5- to 10-membered heteroaryl optionally substituted with 1 to 3 of the same or different substituents selected from the group consisting of halogen, cyano, dimethylamino, $C_1$-6 alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

11. The compound or the pharmaceutically acceptable salt thereof according to claim 1, wherein Y is (1) $C_{1-3}$ alkyl optionally substituted with 1 to 3 of the same or different substituents selected from the group consisting of fluorine, a $C_{3-6}$ alicyclic group, a 5- or 6-membered nitrogen-containing non-aryl heterocyclic group, phenyl (wherein the alicyclic group, the nitrogen-containing non-aryl heterocycle, and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy), (2) a $C_{3-6}$ alicyclic group optionally substituted with 1 to 3 of the same or different substituents selected from the group consisting of fluorine, amino, dimethylamino, $C_{1-3}$ alkyl optionally substituted with 1 to 3 fluorine, a 5- to 6-membered nitrogen-containing non-aryl heterocyclic group, phenyl (wherein the phenyl group is optionally substituted with 1 to 3 of the same or different substituents consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents consisting of fluorine, cyano, $C_{1-3}$ alkyl optionally substituted with 1 to 3 fluorine, and methoxy), (3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine, (4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or (5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine.

12. The compound or the pharmaceutically acceptable salt thereof according to claim 1, wherein Y is (1) $C_{1-3}$ alkyl optionally substituted with 1 to 3 of the same or different substituents selected from the group consisting of fluorine, a $C_{3-6}$ alicyclic group, a 5- or 6-membered nitrogen-containing non-aryl heterocyclic group, phenyl (wherein the alicyclic group, the nitrogen-containing non-aryl heterocycle, and the phenyl group are each independently optionally substituted with 1 to 3 of the same or different substituents selected from the group consisting of fluorine, cyano, $C_{1-3}$ alkyl optionally substituted with 1 to 3 fluorine, and methoxy), and 5-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy), (2) a $C_{5-6}$ alicyclic group or phenylcyclopropyl wherein the $C_{5-6}$ alicyclic group or phenylcyclopropyl is optionally substituted with 1 to 3 of the same or different substituents selected from the group consisting of fluorine, amino, dimethylamino, $C_{2-3}$ alkyl optionally substituted with 1 to 3 fluorine, a 5- to 6-membered nitrogen-containing non-aryl heterocyclic group, phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy), and 5- to 6-membered heteroaryl (wherein the heteroaryl group is optionally substituted with 1 to 3 of the same or different substituents selected from the group consisting of fluorine, cyano, $C_{1-3}$ alkyl optionally substituted with 1 to 3 fluorine, and methoxy), (3) a 4- to 6-membered nitrogen-containing non-aryl heterocyclic group, phenyloxetanyl, or tetrahydropyranyl wherein the 4- to 6-membered nitrogen-containing non-aryl heterocyclic group, phenyloxetanyl, or tetrahydropyranyl is optionally substituted with 1 to 3 of the same or different substituents selected from the group consisting of fluorine, amino, dimethylamino, $C_{2-3}$ alkyl optionally substituted with 1 to 3 fluorine, and phenyl (wherein the phenyl group is optionally substituted with 1 to 3 of the same or different substituents selected from the group consisting of fluorine, cyano, $C_{1-3}$ alkyl optionally substituted with 1 to 3 fluorine, and methoxy), (4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or (5) 6-membered heteroaryl optionally substituted with 1 to 3 of the same or different substituents selected from the group consisting of halogen, cyano, $C_{1-3}$ alkoxy, and $C_{1-3}$ alkyl optionally substituted with 1 to 3 fluorine.

13. The compound or the pharmaceutically acceptable salt thereof according to claim 1, wherein Y is (1) $C_{1-3}$ alkyl optionally substituted with 1 to 3 fluorine, (2) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine, (3) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine, (4) phenyl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine, or (5) 5- or 6-membered heteroaryl optionally substituted with 1 to 3 of the same or different substituents selected from the group consisting of halogen, cyano, dimethylamino, $C_{1-3}$ alkoxy, and $C_{1-3}$ alkyl optionally substituted with 1 to 3 fluorine.

14. The compound or the pharmaceutically acceptable salt thereof according to claim 1, wherein Y is
   (1) a $C_{5-6}$ alicyclic group optionally substituted with 1 to 3 of the same or different substituents selected from the group consisting of fluorine, amino, dimethylamino, and $C_{1-3}$ alkyl optionally substituted with 1 to 3 fluorine,
   (2) a 5- or 6-membered nitrogen-containing non-aryl heterocyclic group optionally substituted with 1 to 3 of the same or different substituents selected from the group consisting of fluorine, amino, dimethylamino, and $C_{1-3}$ alkyl optionally substituted with 1 to 3 fluorine,
   (3) phenyl optionally substituted with 1 to 3 of the same or different substituents selected from the group consisting of halogen, cyano, methoxy, and $C_{1-3}$ alkyl optionally substituted with 1 to 3 fluorine, or
   (4) 5- or 6-membered heteroaryl optionally substituted with 1 to 3 of the same or different substituents selected from the group consisting of halogen, cyano, methoxy, and $C_{1-3}$ alkyl optionally substituted with 1 to 3 fluorine.

15. The compound or the pharmaceutically acceptable salt thereof according to claim 1, wherein Y is
   (1) phenyl optionally substituted with 1 to 2 of the same or different substituents selected from the group consisting of fluorine, cyano, methoxy, and methyl, or
   (2) 5- or 6-membered heteroaryl optionally substituted with 1 to 2 of the same or different substituents selected from the group consisting of fluorine, cyano, methoxy, and methyl.

16. The compound or the pharmaceutically acceptable salt thereof according to claim 1, wherein Y is
   (1) phenyl optionally substituted with 1 to 2 of the same or different substituents selected from the group consisting of fluorine, cyano, methoxy, and methyl, or
   (2) 6-membered heteroaryl optionally substituted with 1 to 2 of the same or different substituents selected from the group consisting of fluorine, cyano, methoxy, and methyl.

17. The compound or the pharmaceutically acceptable salt thereof according to claim 1, wherein Z is 6- to 10-membered heteroaryl optionally substituted with 1 to 3 of the same or different substituents selected from the group consisting of halogen, cyano, $C_{2-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

18. The compound or the pharmaceutically acceptable salt thereof according to claim 1, wherein Z is 6- to 10-membered heteroaryl, thienyl, pyrrolyl, thiazolyl, isothiazolyl, isoxazolyl, or thiadiazolyl wherein the 6- to 10-membered heteroaryl, thienyl, pyrrolyl, thiazolyl, isothiazolyl, isoxazolyl, or thiadiazolyl is optionally substituted with 1 to 3 of the same or different substituents selected from the group consisting of fluorine, cyano, $C_{2-6}$ alkoxy, and $C_{1-6}$ alkyl (wherein the alkoxy and the alkyl are each independently optionally substituted with 1 to 3 of the same or different substituents selected from the group consisting of halogen, hydroxy, and $C_{1-6}$ alkoxy).

19. The compound or the pharmaceutically acceptable salt thereof according to claim 1, wherein Z is 6- to 10-membered heteroaryl optionally substituted with 1 to 3 of the same or different substituents selected from the group consisting of fluorine, chloro, cyano, $C_{1-6}$ alkoxy, and $C_{1-3}$ alkyl optionally substituted with 1 to 3 fluorine.

20. The compound or the pharmaceutically acceptable salt thereof according to claim 1, wherein Z is pyridyl, pyrimidinyl, indazolyl, or imidazopyridyl wherein the pyridyl, pyrimidinyl, indazolyl, or imidazopyridyl is optionally substituted with 1 to 3 of the same or different substituents selected from the group consisting of fluorine, chloro, cyano, methoxy, and $C_{1-3}$ alkyl optionally substituted with 1 to 3 fluorine.

21. The compound or the pharmaceutically acceptable salt thereof according to claim 1, wherein Z is pyridyl optionally substituted with 1 to 3 of the same or different substituents selected from the group consisting of fluorine, chloro, cyano, and $C_{1-3}$ alkyl optionally substituted with 1 to 3 fluorine.

22. The compound or the pharmaceutically acceptable salt thereof according to claim 1, selected from the following compounds:
   4-oxo-3-phenyl-2-(pyridin-3-ylamino)-3,4-dihydroquinazoline-6-carbonitrile,
   6-fluoro-2-((5-fluoropyridin-3-yl)amino)-3-(o-tolyl) quinazolin-4 (3H)-one,
   6-chloro-2-((2-methoxypyridin-3-yl)amino)-3-phenylquinazolin-4 (3H)-one,
   6-fluoro-3-phenyl-2-(pyridin-3-ylamino) quinazolin-4 (3H)-one,
   3-phenyl-2-(pyridin-3-ylamino) quinazolin-4 (3H)-one,
   6-chloro-3-(2-chlorophenyl)-2-(pyridin-3-ylamino) quinazolin-4 (3H)-one,
   6-chloro-3-phenyl-2-(pyridin-3-ylamino) quinazolin-4 (3H)-one,
   6,8-difluoro-3-phenyl-2-(pyridin-3-ylamino) quinazolin-4 (3H)-one,
   6-fluoro-3-(pyridin-3-yl)-2-(pyridin-3-ylamino) quinazolin-4 (3H)-one,
   6-chloro-3-phenyl-2-(pyrazin-2-ylamino) quinazolin-4 (3H)-one,
   6-fluoro-3-phenyl-2-(pyrazin-2-ylamino) quinazolin-4 (3H)-one,
   6-fluoro-2-((5-fluoropyridin-3-yl)amino)-3-phenylquinazolin-4 (3H)-one,
   5-((6-chloro-4-oxo-3-phenyl-3,4-dihydroquinazolin-2-yl) amino) nicotinonitrile,
   6-methyl-3-phenyl-2-(pyridin-3-ylamino) quinazolin-4 (3H)-one,
   2-((5-chloropyridin-3-yl)amino)-6-fluoro-3-phenylquinazolin-4 (3H)-one,
   6-chloro-3-(2-fluorophenyl)-2-(pyridin-3-ylamino) quinazolin-4 (3H)-one,
   2-((1-methyl-1H-indazol-6-yl)amino)-3-phenylquinazolin-4 (3H)-one,
   2-(imidazo [1,5-a]pyridin-8-ylamino)-3-phenylquinazolin-4 (3H)-one,
   3-(4-methoxy-2-methylphenyl)-4-oxo-2-(pyridin-3-ylamino)-3,4-dihydroquinazoline-6-carbonitrile,
   3-(5-fluoro-2-methylphenyl)-4-oxo-2-(pyridin-3-ylamino)-3,4-dihydroquinazoline-6-carbonitrile,
   6-fluoro-2-(pyridin-3-ylamino)-3-(p-tolyl) quinazolin-4 (3H)-one,
   6-fluoro-2-(pyridin-3-ylamino)-3-(o-tolyl) quinazolin-4 (3H)-one, 6-fluoro-3-(2-fluorophenyl)-2-(pyridin-3-ylamino) quinazolin-4 (3H)-one, 4-oxo-2-(pyridin-3-ylamino)-3-(o-tolyl)-3,4-dihydroquinazoline-6-carbonitrile, 6-fluoro-3-(2-fluorophenyl)-2-((5-fluoropyridin-3-yl)amino) quinazolin-4 (3H)-one, 2-((5-fluoropyridin-3-yl)amino)-4-oxo-3-phenyl-3,4-dihydroquinazoline-6-carbonitrile, 3-(2-fluorophenyl)-2-((5-fluoropyridin-3-yl)amino)-4-oxo-3,4-dihydroquinazoline-6-carbonitrile, 2-((5-fluoropyridin-3-yl)amino)-4-oxo-3-(o-tolyl)-3,4-dihydroquinazoline-6-carbonitrile, 6-fluoro-2-((4-fluoropyridin-2-yl)amino)-3-phenylquinazolin-4 (3H)-one, 6-fluoro-2-((5-methylpyridin-2-yl)amino)-3-phenylquinazolin-4 (3H)-one, 6-fluoro-2-((2-fluoropyridin-4-yl)amino)-3-phenylquinazolin-4 (3H)-one, 6-fluoro-3-(2-methoxyphenyl)-2-(pyridin-3-ylamino) quinazolin-4 (3H)-one, and 3-(2-chlorophenyl)-6-fluoro-2-(pyridin-3-ylamino) quinazolin-4 (3H)-one.

23. A medicament comprising the compound or the pharmaceutically acceptable salt thereof according to claim 1 as an active ingredient and at least one pharmaceutically acceptable excipient.

24. A pharmaceutical composition comprising the compound or the pharmaceutically acceptable salt thereof according to claim 1.

25. A method for treating or preventing a disorder or disease associated with an abnormal nerve excitation, comprising administering a therapeutically or prophylactically effective amount of the compound or the pharmaceutically acceptable salt thereof according to claim 1 to a patient in need thereof.

26. A pharmaceutical composition comprised of the compound or the pharmaceutically acceptable salt thereof according to claim 1 in combination with at least one agent selected from agents classified as an antiepileptic medicament, an antidepressant, an anxiolytic, or an antipsychotic medicament.

27. A pharmaceutical kit comprising the compound or the pharmaceutically acceptable salt thereof according to claim 1 and at least one agent selected from agents classified as an antiepileptic medicament, an antidepressant, an anxiolytic, or an antipsychotic medicament.

* * * * *